(12) United States Patent
Flotte et al.

(10) Patent No.: US 10,077,452 B2
(45) Date of Patent: *Sep. 18, 2018

(54) RAAV-BASED COMPOSITIONS AND METHODS

(71) Applicant: University of Massachusetts, Boston, MA (US)

(72) Inventors: Terence Flotte, Holden, MA (US); Christian Mueller, Concord, MA (US); Phillip D. Zamore, Northborough, MA (US)

(73) Assignee: University of Massachusetts, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/098,833

(22) Filed: Apr. 14, 2016

(65) Prior Publication Data

US 2016/0326524 A1 Nov. 10, 2016
US 2017/0369874 A9 Dec. 28, 2017

Related U.S. Application Data

(63) Continuation of application No. 14/952,217, filed on Nov. 25, 2015, now Pat. No. 9,885,057, which is a continuation of application No. 14/113,118, filed as application No. PCT/US2012/034446 on Apr. 20, 2012, now Pat. No. 9,226,976.

(60) Provisional application No. 61/477,671, filed on Apr. 21, 2011.

(51) Int. Cl.
| | |
|---|---|
| *C07H 21/02* | (2006.01) |
| *C07H 21/04* | (2006.01) |
| *A61K 48/00* | (2006.01) |
| *A61K 35/00* | (2006.01) |
| *C12N 15/86* | (2006.01) |
| *C12N 15/67* | (2006.01) |
| *A61K 35/12* | (2015.01) |
| *C12N 7/00* | (2006.01) |
| *C12N 15/113* | (2010.01) |
| *A61K 31/713* | (2006.01) |
| *A61K 38/57* | (2006.01) |
| *C07K 14/81* | (2006.01) |
| *C12N 15/11* | (2006.01) |

(52) U.S. Cl.
CPC ............ *C12N 15/86* (2013.01); *A61K 31/713* (2013.01); *A61K 35/12* (2013.01); *A61K 38/57* (2013.01); *A61K 48/005* (2013.01); *A61K 48/0058* (2013.01); *C07K 14/8125* (2013.01); *C12N 7/00* (2013.01); *C12N 15/113* (2013.01); *C12N 15/67* (2013.01); *C12N 15/111* (2013.01); *C12N 2310/141* (2013.01); *C12N 2310/3519* (2013.01); *C12N 2320/31* (2013.01); *C12N 2750/14121* (2013.01); *C12N 2750/14132* (2013.01); *C12N 2750/14143* (2013.01)

(58) Field of Classification Search
CPC .. C12N 2310/14; C12N 15/111; C12N 15/113
See application file for complete search history.

(56) References Cited

U.S. PATENT DOCUMENTS

| | | | |
|---|---|---|---|
| 5,478,745 | A | 12/1995 | Samulski et al. |
| 5,871,982 | A | 2/1999 | Wilson et al. |
| 6,177,403 | B1 | 1/2001 | Stedman |
| 6,251,677 | B1 | 6/2001 | Wilson et al. |
| 6,485,966 | B2 | 11/2002 | Gao et al. |
| 6,544,786 | B1 | 4/2003 | Xiao et al. |
| 7,022,519 | B2 | 4/2006 | Gao et al. |
| 7,198,951 | B2 | 4/2007 | Gao et al. |
| 7,235,393 | B2 | 6/2007 | Gao et al. |
| 7,427,396 | B2 | 9/2008 | Arbetman et al. |
| 7,456,015 | B2 | 11/2008 | Bohn et al. |
| 7,906,111 | B2 | 3/2011 | Wilson et al. |
| 8,222,221 | B2 | 7/2012 | Corey et al. |
| 8,524,446 | B2 | 9/2013 | Gao et al. |
| 8,734,809 | B2 | 5/2014 | Gao et al. |
| 9,102,949 | B2 | 8/2015 | Gao et al. |
| 9,217,155 | B2 | 12/2015 | Gao et al. |
| 9,226,976 | B2 | 1/2016 | Flotte et al. |
| 9,272,053 | B2 | 3/2016 | Gao et al. |
| 9,284,357 | B2 | 3/2016 | Gao et al. |
| 2001/0016355 | A1 | 8/2001 | Samulski et al. |
| 2002/0192823 | A1 | 12/2002 | Bartlett |
| 2003/0103939 | A1 | 6/2003 | Engelhardt et al. |
| 2003/0110526 | A1 | 6/2003 | Brown et al. |
| 2003/0138772 | A1 | 7/2003 | Gao et al. |
| 2004/0101514 | A1 | 5/2004 | Liu et al. |
| 2005/0037988 | A1 | 2/2005 | Zamore et al. |
| 2005/0137153 | A1 | 6/2005 | McSwiggen et al. |
| 2005/0255086 | A1 | 11/2005 | Davidson et al. |
| 2005/0287122 | A1 | 12/2005 | Bartlett et al. |

(Continued)

FOREIGN PATENT DOCUMENTS

| | | |
|---|---|---|
| EP | 12774597.4 | 2/2015 |
| EP | 17201358.3 | 2/2018 |

(Continued)

OTHER PUBLICATIONS

U.S. Appl. No. 15/516,582, filed Apr. 3, 2017, Esteves et al.

(Continued)

*Primary Examiner* — Amy H Bowman
(74) *Attorney, Agent, or Firm* — Wolf, Greenfield & Sacks, P.C.

(57) ABSTRACT

The invention relates to isolated nucleic acids and rAAV-based compositions, methods and kits useful for treating genetic diseases (e.g., alpha-1 antitrypsin deficiency).

17 Claims, 10 Drawing Sheets
Specification includes a Sequence Listing.

(56) References Cited

U.S. PATENT DOCUMENTS

| | | |
|---|---|---|
| 2006/0063174 A1 | 3/2006 | Turner et al. |
| 2006/0093589 A1 | 5/2006 | Warrington et al. |
| 2006/0189564 A1 | 8/2006 | Burright et al. |
| 2006/0228800 A1 | 10/2006 | Lin et al. |
| 2006/0292117 A1 | 12/2006 | Loiler et al. |
| 2007/0036760 A1 | 2/2007 | Wilson et al. |
| 2007/0243526 A1 | 10/2007 | Kay et al. |
| 2009/0111766 A1 | 4/2009 | Atkinson et al. |
| 2009/0131355 A1 | 5/2009 | Bot et al. |
| 2009/0149409 A1 | 6/2009 | Bohn et al. |
| 2009/0239240 A1 | 9/2009 | Chu |
| 2010/0186103 A1 | 7/2010 | Gao et al. |
| 2010/0323001 A1 | 12/2010 | Pachuk |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2012/0137379 A1 | 5/2012 | Gao et al. |
| 2012/0270930 A1 | 10/2012 | Van Der Maarel et al. |
| 2013/0101558 A1 | 4/2013 | Gao et al. |
| 2013/0109742 A1 | 5/2013 | Hewitt et al. |
| 2013/0195801 A1 | 8/2013 | Gao et al. |
| 2013/0281516 A1 | 10/2013 | Gao et al. |
| 2014/0142161 A1 | 5/2014 | Flotte et al. |
| 2014/0179770 A1 | 6/2014 | Zhang et al. |
| 2014/0201857 A1 | 7/2014 | Fahrenkrug et al. |
| 2014/0296486 A1 | 10/2014 | Gao et al. |
| 2014/0335054 A1 | 11/2014 | Gao et al. |
| 2015/0065560 A1 | 3/2015 | Bjorklund et al. |
| 2016/0017005 A1 | 1/2016 | Asokan et al. |
| 2016/0060624 A1 | 3/2016 | Davidson et al. |
| 2016/0135438 A1 | 5/2016 | Gao et al. |
| 2016/0153005 A1 | 6/2016 | Feng et al. |
| 2016/0186211 A1 | 6/2016 | Flotte et al. |

FOREIGN PATENT DOCUMENTS

| | | |
|---|---|---|
| EP | 17201379.9 | 2/2018 |
| WO | WO 2003/042397 | 5/2003 |
| WO | WO 2003/093460 | 11/2003 |
| WO | WO 2005/033321 | 4/2005 |
| WO | WO 2006/031267 A2 | 3/2006 |
| WO | WO 2006/119432 A2 | 11/2006 |
| WO | WO 2007/000668 A2 | 1/2007 |
| WO | WO 2007/027775 A2 | 3/2007 |
| WO | WO 2007/127264 A2 | 11/2007 |
| WO | WO 2008/091703 | 7/2008 |
| WO | WO 2008/125846 A2 | 10/2008 |
| WO | WO 2008/147839 A1 | 12/2008 |
| WO | WO 2008/150897 A2 | 12/2008 |
| WO | WO 2009/109665 A1 | 9/2009 |
| WO | WO 2009/130208 | 10/2009 |
| WO | WO 2009/146178 A1 | 12/2009 |
| WO | WO 2010/034314 A1 | 4/2010 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | PCT/US2012/034446 | 11/2012 |
| WO | PCT/US2012/034446 | 10/2013 |
| WO | WO 2013/170078 A1 | 11/2013 |
| WO | WO 2013/190059 A1 | 12/2013 |
| WO | WO 2014/197748 A2 | 11/2014 |

OTHER PUBLICATIONS

U.S. Appl. No. 15/516,585, filed Apr. 3, 2017, Esteves et al.
U.S. Appl. No. 15/520,977, filed Apr. 21, 2017, Gao et al.
U.S. Appl. No. 15/613,646, filed Jun. 5, 2017, Gao et al.
U.S. Appl. No. 15/550,452, filed Aug. 11, 2017, Gao et al.
U.S. Appl. No. 15/567,847, filed Oct. 19, 2017, Esteves et al.
U.S. Appl. No. 15/568,650, filed Oct. 23, 2017, Gao et al.
U.S. Appl. No. 15/747,801, filed Jan. 26, 2018, Fitzgerald et al.
U.S. Appl. No. 15/705,909, filed Sep. 15, 2017, Mueller et al.

Adachi et al., Drawing a high-resolution functional map of adeno-associated virus capsid by massively parallel sequencing. Nat Commun. 2014;5:3075. doi: 10.1038/ncomms4075.
Afione et al., In vivo model of adeno-associated virus vector persistence and rescue. J Virol. May 1996;70(5):3235-41.
Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].
Akache et al., The 37/67-kilodalton laminin receptor is a receptor for adeno-associated virus serotypes 8, 2, 3, and 9. J Virol. Oct. 2006;80(19):9831-6.
Alisky et al., Gene therapy for amyotrophic lateral sclerosis and other motor neuron diseases. Hum Gene Ther. Nov. 20, 2000;11(17):2315-29.
Ameres et al., Target RNA-directed tailing and trimming purifies the sorting of endo-siRNAs between the two *Drosophila argonaute* proteins. RNA. Jan. 2011;17(1):54-63. doi: 10.1261/rna.2498411. Epub Nov. 24, 2010.
Ameres et al., Target RNA-directed trimming and tailing of small silencing RNAs. Science. Jun. 18, 2010;328(5985):1534-9. doi: 10.1126/science.1187058.
Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.
Asokan et al., The AAV vector toolkit: poised at the clinical crossroads. Mol Ther. Apr. 2012;20(4):699-708. doi: 10.1038/mt. 2011.287. Epub Jan. 24, 2012.
Azzouz et al., VEGF delivery with retrogradely transported lentivector prolongs survival in a mouse ALS model. Nature. May 27, 2004;429(6990):413-7.
Bals et al., Transduction of well-differentiated airway epithelium by recombinant adeno-associated virus is limited by vector entry. J Virol. Jul. 1999;73(7):6085-8.
Barcia et al., Intraventricular and intracerebral delivery of anti-epileptic drugs in the kindling model. Neurotherapeutics. Apr. 2009;6(2):337-43.
Bernacki et al., Mucin gene expression during differentiation of human airway epithelia in vitro. Muc4 and muc5b are strongly induced. Am J Respir Cell Mol Biol. Apr. 1999;20(4):595-604.
Berns et al., Biology of adeno-associated virus. Curr Top Microbiol Immunol. 1996;218:1-23.
Berns et al., Detection of adeno-associated virus (AAV)-specific nucleotide sequences in DNA isolated from latently infected Detroit 6 cells. Virology. Dec. 1975;68(2):556-60.
Beutler et al., AAV for pain: steps towards clinical translation. Gene Ther. Apr. 2009;16(4):461-9. Epub Mar. 5, 2009.
Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.
Boillée et al., Onset and progression in inherited ALS determined by motor neurons and microglia. Science. Jun. 2, 2006;312(5778):1389-92.
Bolstad et al., A comparison of normalization methods for high density oligonucleotide array data based on variance and bias. Bioinformatics. Jan. 22, 2003;19(2):185-93.
Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.
Bourlais et al., Ophthalmic drug delivery systems—recent advances. Prog Retin Eye Res. Jan. 1998;17(1):33-58.
Brantly et al., Phase I trial of intramuscular injection of a recombinant adeno-associated virus serotype 2 alpha1-antitrypsin (AAT) vector in AAT-deficient adults. Hum Gene Ther. Dec. 2006;17(12):1177-86.
Brown et al., A microRNA-regulated lentiviral vector mediates stable correction of hemophilia B mice. Blood. Dec. 15, 2007;110(13):4144-52. Epub Aug. 28, 2007.

(56) References Cited

OTHER PUBLICATIONS

Brown et al., Endogenous microRNA can be broadly exploited to regulate transgene expression according to tissue, lineage and differentiation state. Nat Biotechnol. Dec. 2007;25(12):1457-67. Epub Nov. 16, 2007.
Brown et al., Endogenous microRNA regulation suppresses transgene expression in hematopoietic lineages and enables stable gene transfer. Nat Med. May 2006;12(5):585-91. Epub Apr. 23, 2006.
Bukh, A critical role for the chimpanzee model in the study of hepatitis C. Hepatology. Jun. 2004;39(6):1469-75.
Buning et al., Receptor targeting of adeno-associated virus vectors. Gene Ther. Jul. 2003;10(14):1142-51.
Büssing et al., let-7 microRNAs in development, stem cells and cancer. Trends Mol Med. Sep. 2008;14(9):400-9. doi: 10.1016/j.molmed.2008.07.001. Epub Jul. 31, 2008.
Calcedo et al., Worldwide epidemiology of neutralizing antibodies to adeno-associated viruses. J Infect Dis. Feb. 1, 2009;199(3):381-90.
Carè et al., MicroRNA-133 controls cardiac hypertrophy. Nat Med. May 2007;13(5):613-8. Epub Apr. 29, 2007.
Carter et al., Adeno-associated virus gene expression and regulation. CRC Handbook of parvoviruses. 1990:227-54.
Carter, in "Handbook of Parvoviruses", ed., P. Tijsser, CRC Press, pp. 155-168 (1990).
Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.
Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.
Chadderton et al., Improved retinal function in a mouse model of dominant retinitis pigmentosa following AAV-delivered gene therapy. Mol Ther. Apr. 2009;17(4):593-9. Epub Jan. 27, 2009.
Chang et al., miR-122, a mammalian liver-specific microRNA, is processed from her mRNA and may downregulate the high affinity cationic amino acid transporter CAT-1. RNA Biol. Jul. 2004;1(2):106-13. Epub Jul. 1, 2004.
Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.
Chen et al., Efficient transduction of vascular endothelial cells with recombinant adeno-associated virus serotype 1 and 5 vectors. Hum Gene Ther. Feb. 2005;16(2):235-47.
Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.
Chen et al., Regulation of immune responses and tolerance: the microRNA perspective. Immunol Rev. May 2013;253(1):112-28. doi:10.1111/imr.12060.
Chirmule et al., Humoral immunity to adeno-associated virus type 2 vectors following administration to murine and nonhuman primate muscle. J Virol. Mar. 2000;74(5):2420-5.
Choi et al., Effects of adeno-associated virus DNA hairpin structure on recombination. J Virol. Jun. 2005;79(11):6801-7.
Choudhury et al., Identification of Novel vectors capable of CNS transduction in adult mice after single round selection using DNA shuffled AAV capsid library. Mol Ther. May 1, 2013;21(1):S1.
Christensen et al., A let-7 microRNA-binding site polymorphism in the KRAS 3' UTR is associated with reduced survival in oral cancers. Carcinogenesis. Jun. 2009;30(6):1003-7. doi: 10.1093/carcin/bgp099. Epub Apr. 20, 2009.
Chu et al., SV40 DNA transfection of cells in suspension: analysis of efficiency of transcription and translation of T-antigen. Gene. Mar. 1981;13(2):197-202.
Cideciyan et al., Human RPE65 gene therapy for Leber congenital amaurosis: persistence of early visual improvements and safety at 1 year. Hum Gene Ther. Sep. 2009;20(9):999-1004.

Conlon et al., Efficient hepatic delivery and expression from a recombinant adeno-associated virus 8 pseudotyped alphal-antitrypsin vector. Mol Ther. Nov. 2005;12(5):867-75. Epub Aug. 8, 2005.
Conlon et al., Ribozyme Approaches towards Down-Regulation of Pi*Z Mutant Human a-1 Anti-Trypsin. Mol. Therapy. 2004;9:S333. Abstract 875.
Conrad et al., Safety of single-dose administration of an adeno-associated virus (AAV)-CFTR vector in the primate lung. Gene Ther. Aug. 1996;3(8):658-68.
Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.
Crowe et al., A comparison in chimpanzees of the immunogenicity and efficacy of live attenuated respiratory syncytial virus (RSV) temperature-sensitive mutant vaccines and vaccinia virus recombinants that express the surface glycoproteins of RSV. Vaccine. Nov. 1993;11(14):1395-404.
Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.
Cruz et al., The promise of gene therapy for the treatment of alpha-1 antitrypsin deficiency. Pharmacogenomics. Sep. 2007;8(9):1191-8.
Curtin et al., Bidirectional promoter interference between two widely used internal heterologous promoters in a late-generation lentiviral construct. Gene Ther. Mar. 2008;15(5):384-90. doi: 10.1038/sj.gt.3303105. Epub Jan. 24, 2008.
Czech, MicroRNAs as therapeutic targets. N Engl J Med. Mar. 16, 2006;354(11):1194-5.
Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.
Davidson et al., A model system for in vivo gene transfer into the central nervous system using an adenoviral vector. Nat Genet. Mar. 1993;3(3):219-23.
Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.
Daya et al., Gene therapy using adeno-associated virus vectors. Clin Microbiol Rev. Oct. 2008;21(4):583-93. doi: 10.1128/CMR.00008-08.
Di Giorgio et al., Non-cell autonomous effect of glia on motor neurons in an embryonic stem cell-based ALS model. Nat Neurosci. May 2007;10(5):608-14. Epub Apr. 15, 2007.
Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.
Eberling et al., Results from a phase I safety trial of hAADC gene therapy for Parkinson disease. Neurology. May 20, 2008;70(21):1980-3. doi: 10.1212/01.wnl.0000312381.29287.ff. Epub Apr. 9, 2008.
Ebert et al., MicroRNA sponges: competitive inhibitors of small RNAs in mammalian cells. Nat Methods. Sep. 2007;4(9):721-6. Epub Aug. 12, 2007.
Ehlert et al., Cellular toxicity following application of adeno-associated viral vector-mediated RNA interference in the nervous system. BMC Neurosci. Feb. 18, 2010;11:20.
Elmén et al., Antagonism of microRNA-122 in mice by systemically administered LNA-antimiR leads to up-regulation of a large set of predicted target mRNAs in the liver. Nucleic Acids Res. Mar. 2008;36(4):1153-62. Epub Dec. 23, 2007.
Elmen et al., LNA-mediated microRNA silencing in non-human primates. Nature. Apr. 17, 2008;452(7189):896-9. Epub Mar. 26, 2008.
Engelhardt et al., Adenovirus-mediated transfer of the CFTR gene to lung of nonhuman primates: biological efficacy study. Hum Gene Ther. Dec. 1993;4(6):759-69.
Esau et al., miR-122 regulation of lipid metabolism revealed by in vivo antisense targeting. Cell Metab. Feb. 2006;3(2):87-98.

(56) References Cited

OTHER PUBLICATIONS

Fabani et al., miR-122 targeting with LNA/2'-O-methyl oligonucleotide mixmers, peptide nucleic acids (PNA), and PNA-peptide conjugates. RNA. Feb. 2008;14(2):336-46. Epub Dec. 11, 2007.
Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.
Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.
Fire et al., Potent and specific genetic interference by double-stranded RNA in Caenorhabditis elegans. Nature. Feb. 19, 1998;391(6669):806-11.
Fischer et al., Successful transgene expression with serial doses of aerosolized rAAV2 vectors in rhesus macaques. Mol Ther. Dec. 2003;8(6):918-26.
Fisher et al., Transduction with recombinant adeno-associated virus for gene therapy is limited by leading-strand synthesis. J Virol. Jan. 1996;70(1):520-32.
Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.
Flotte, Recombinant adeno-associated virus (AAV) gene therapy vectors for, cystic fibrosis (CF), alpha-1-antitrypsin deficiency (AAT) and fatty oxidation disorders (FAO). Umass Medical School. Interdisciplinary Graduate Program. Last accessed at http://www.umassmed.edu/igp/faculty/flotte.cfm?start=0& on Aug. 27, 2009.
Forman et al., A search for conserved sequences in coding regions reveals that the let-7 microRNA targets Dicer within its coding sequence. Proc Natl Acad Sci U S A. Sep. 30, 2008;105(39):14879-84. doi: 10.1073/pnas.0803230105. Epub Sep. 23, 2008.
Foust et al., Intravascular AAV9 preferentially targets neonatal-neurons and adult-astrocytes. Nature Biotechnology, 27; 59-65 2009.
Foust et al., Rescue of the spinal muscular atrophy phenotype in a mouse model by early postnatal delivery of SMN. Nat Biotechnol. Mar. 2010;28(3):271-4. doi: 10.1038/nbt.1610. Epub Feb. 28, 2010.
Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.
Fu et al., Evaluation of cellular immune responses in subjects chronically infected with HIV type 1. AIDS Res Hum Retroviruses. Jan. 2007;23(1):67-76.
Fu et al., Self-complementary adeno-associated virus serotype 2 vector: global distribution and broad dispersion of AAV-mediated transgene expression in mouse brain. Mol Ther. Dec. 2003;8(6):911-7.
Gao et al., Adeno-associated viruses undergo substantial evolution in primates during natural infections. Proc Natl Acad Sci U S A. May 13, 2003;100(10):6081-6. Epub Apr. 25, 2003.
Gao et al., Adeno-associated virus-mediated gene transfer to non-human primate liver can elicit destructive transgene-specific T cell responses. Hum Gene Ther. Sep. 2009;20(9):930-42. doi: 10.1089/hum.2009.060.
Gao et al., Biology of AAV serotype vectors in liver-directed gene transfer to nonhuman primates. Mol Ther. Jan. 2006;13(1):77-87. Epub Oct. 10, 2005.
Gao et al., Clades of Adeno-associated viruses are widely disseminated in human tissues. J Virol. Jun. 2004;78(12):6381-8.
Gao et al., Erythropoietin gene therapy leads to autoimmune anemia in macaques. Blood. May 1, 2004;103(9):3300-2. Epub Dec. 24, 2003.
Gao et al., In situ synthesis of oligonucleotide microarrays. Biopolymers. Apr. 5, 2004;73(5):579-96.
Gao et al., Inadvertent gene transfer of co-packaged rep and cap sequences during the production of AAV vector and its potential impact on vector performance. Molecular Therapy. May 2008;16(Suppl. 1):S105-S106. Abstract 279.
Gao et al., New recombinant serotypes of AAV vectors. Curr Gene Ther. Jun. 2005;5(3):285-97.
Gao et al., Novel adeno-associated viruses from rhesus monkeys as vectors for human gene therapy. Proc Natl Acad Sci U S A. Sep. 3, 2002;99(18):11854-9. Epub Aug. 21, 2002.
Gao et al., Purification of recombinant adeno-associated virus vectors by column chromatography and its performance in vivo. Hum Gene Ther. Oct. 10, 2000;11(15):2079-91.
Gao et al., RAAV-mediated targeting in adult mice and its potential in generating animal models of tissue-specific somatic transgenics or knock down. Molecular Therapy. May 2008;16(1):S118-S119. Abstract 316.
Genbank Submission; Accession No. ADZ26851; Wilson et al.; Jun. 30, 2005.
Genbank Submission; NCBI, Accession No. AAB95450; Rutledge et al.; Jan. 12, 1998.
Genbank Submission; NCBI, Accession No. AAS99264; Gao et al.; Jun. 24, 2004.
Genbank Submission; NCBI, Accession No. ABA71701; Schmidt et al.; May 10, 2006.
Genbank Submission; NCBI, Accession No. ACB55301; Vandenberghe et al.; Jul. 31, 2008.
Genbank Submission; NCBI, Accession No. ACB55310; Vandenberghe et al.; Jul. 31, 2008.
Genbank Submission; NCBI, Accession No. NP_049542; Xiao et al.; Mar. 11, 2010.
Genbank Submission; NCBI, Accession No. YP_680426; Ruffing et al.; Nov. 19, 2010.
Gentner et al., Stable knockdown of microRNA in vivo by lentiviral vectors. Nat Methods. Jan. 2009;6(1):63-6. doi: 10.1038/nmeth.1277. Epub Nov. 30, 2008.
Girard et al., miR-122, a paradigm for the role of microRNAs in the liver. J Hepatol. Apr. 2008;48(4):648-56. doi: 10.1016/j.jhep.2008.01.019. Epub Feb. 12, 2008.
Graham et al., A new technique for the assay of infectivity of human adenovirus 5 DNA. Virology. Apr. 1973;52(2):456-67.
Gramantieri et al., Cyclin G1 is a target of miR-122a, a microRNA frequently down-regulated in human hepatocellular carcinoma. Cancer Res. Jul. 1, 2007;67(13):6092-9.
Griffiths-Jones et al., miRBase: microRNA sequences, targets and gene nomenclature. Nucleic Acids Res. Jan. 1, 2006;34(Database issue):D140-4.
Grimm et al., Fatality in mice due to oversaturation of cellular microRNA/short hairpin RNA pathways. Nature. May 25, 2006;441(7092):537-41.
Grimm et al., Therapeutic application of RNAi: is mRNA targeting finally ready for prime time? J Clin Invest. Dec. 2007;117(12):3633-41.
Grimm, Small silencing RNAs: state-of-the-art. Adv Drug Deliv Rev. Jul. 25, 2009;61(9):672-703. doi: 10.1016/j.addr.2009.05.002. Epub May 7, 2009.
Gruenert et al., Culture and transformation of human airway epithelial cells. Am J Physiol. Mar. 1995;268(3 Pt 1):L347-60.
Haraguchi et al., Vectors expressing efficient RNA decoys achieve the long-term suppression of specific microRNA activity in mammalian cells. Nucleic Acids Res. Apr. 2009;37(6):e43. doi: 10.1093/nar/gkp040. Epub Feb. 17, 2009.
Haussecker et al., miR-122 continues to blaze the trail for microRNA therapeutics. Mol Ther. Feb. 2010;18(2):240-2. doi: 10.1038/mt.2009.313.
Hauswirth et al., Treatment of leber congenital amaurosis due to RPE65 mutations by ocular subretinal injection of adeno-associated virus gene vector: short-term results of a phase I trial. Hum Gene Ther. Oct. 2008;19(10):979-90.
Hernandez et al., Latent adeno-associated virus infection elicits humoral but not cell-mediated immune responses in a nonhuman primate model. J Virol. Oct. 1999;73(10):8549-58.

(56) References Cited

OTHER PUBLICATIONS

Hildinger et al., Hybrid vectors based on adeno-associated virus serotypes 2 and 5 for muscle-directed gene transfer. J Virol. Jul. 2001;75(13):6199-203.

Horwich et al., Design and delivery of antisense oligonucleotides to block microRNA function in cultured Drosophila and human cells. Nat Protoc. 2008;3(10):1537-49. doi: 10.1038/nprot.2008.145.

Hutvágner et al., Sequence-specific inhibition of small RNA function. PLoS Biol. Apr. 2004;2(4):E98. Epub Feb. 24, 2004.

Iida et al., Systemic Delivery of Tyrosine-Mutant AAV Vectors Results in Robust Transduction of Neurons in Adult Mice. BioMed Res Int. 2013;2013.

Jackman et al., Stabilization of the oxy form of tyrosinase by a single conservative amino acid substitution. Biochem J. Mar. 15, 1992;282 ( Pt 3):915-8.

Johnson et al., RAS is regulated by the let-7 microRNA family. Cell. Mar. 11, 2005;120(5):635-47.

Kaspar et al., Retrograde viral delivery of IGF-1 prolongs survival in a mouse ALS model. Science. Aug. 8, 2003;301(5634):839-42.

Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.

Kota et al., Therapeutic microRNA delivery suppresses tumorigenesis in a murine liver cancer model. Cell. Jun. 12, 2009;137(6):1005-17. doi: 10.1016/j.cell.2009.04.021.

Kotin et al., Organization of adeno-associated virus DNA in latently infected Detroit 6 cells. Virology. Jun. 1989;170(2):460-7.

Kotin et al., Site-specific integration by adeno-associated virus. Proc Natl Acad Sci U S A. Mar. 1990;87(6):2211-5.

Krützfeldt et al., Silencing of microRNAs in vivo with 'antagomirs'. Nature. Dec. 1, 2005;438(7068):685-9. Epub Oct. 30, 2005.

Kumar et al., Canavan disease: a white matter disorder. Ment Retard Dev Disabil Res Rev. 2006;12(2):157-65.

Kumar et al., Lack of aspartoacylase activity disrupts survival and differentiation of neural progenitors and oligodendrocytes in a mouse model of Canavan disease. J Neurosci Res. Nov. 15, 2009;87(15):3415-27. doi: 10.1002/jnr.22233.

Kutay et al., Downregulation of miR-122 in the rodent and human hepatocellular carcinomas. J Cell Biochem. Oct. 15, 2006;99(3):671-8.

Kwiatkowski et al., Clinical, genetic, and pharmacogenetic applications of the Invader assay. Mol Diagn. Dec. 1999;4(4):353-64.

Lanford et al., Therapeutic silencing of microRNA-122 in primates with chronic hepatitis C virus infection. Science. Jan. 8, 2010;327(5962):198-201. Epub Dec. 3, 2009.

Lawlor et al., Efficient gene delivery and selective transduction of glial cells in the mammalian brain by AAV serotypes isolated from nonhuman primates. Mol Ther. Oct. 2009;17(10):1692-702. doi:10.1038/mt.2009.170.

Lebherz et al., Gene therapy with novel adeno-associated virus vectors substantially diminishes atherosclerosis in a murine model of familial hypercholesterolemia. J Gene Med. Jun. 2004;6(6):663-72.

Lewis et al., Conserved seed pairing, often flanked by adenosines, indicates that thousands of human genes are microRNA targets. Cell. Jan. 14, 2005;120(1):15-20.

Lewis et al., Prediction of mammalian microRNA targets. Cell. Dec. 26, 2003;115(7):787-98.

Li et al., Ex vivo transduction and transplantation of bone marrow cells for liver gene delivery of alpha1-antitrypsin. Mol Ther. Aug. 2010;18(8):1553-8. Epub Jun. 15, 2010.

Li et al., Intronic microRNA: discovery and biological implications. DNA Cell Biol. Apr. 2007;26(4):195-207.

Lin et al., Impact of preexisting vector immunity on the efficacy of adeno-associated virus-based HIV-1 Gag vaccines. Hum Gene Ther. Jul. 2008;19(7):663-9.

Lin et al., Intronic MicroRNA (miRNA). J Biomed Biotechnol. 2006;2006:26818.

Liu et al., Biological Differences in rAAV Transduction of Airway Epithelia in Humans and in Old World Non-human Primates. Mol Ther. Dec. 2007;15(12):2114-23. Epub Jul. 31, 2007.

Liu et al., Comparative biology of rAAV transduction in ferret, pig and human airway epithelia. Gene Ther. Nov. 2007;14(21):1543-8. Epub Aug. 30, 2007.

Liu et al., Species-specific differences in mouse and human airway epithelial biology of recombinant adeno-associated virus transduction. Am J Respir Cell Mol Biol. Jan. 2006;34(1):56-64. Epub Sep. 29, 2005.

Loiler et al., Targeting recombinant adeno-associated virus vectors to enhance gene transfer to pancreatic islets and liver. Gene Ther. Sep. 2003;10(18):1551-8.

Lomas et al., the mechanism of Z alpha 1-antitrypsin accumulation in the liver. Nature. Jun. 18, 1992;357(6379):605-7.

Lowenstein, Crossing the rubicon. Nat Biotechnol. Jan. 2009;27(1):42-4.

Loya et al., Transgenic microRNA inhibition with spatiotemporal specificity in intact organisms. Nat Methods. Dec. 2009;6(12):897-903. doi: 10.1038/nmeth.1402. Epub Nov. 15, 2009.

Lux et al., Green fluorescent protein-tagged adeno-associated virus particles allow the study of cytosolic and nuclear trafficking. J Virol. Sep. 2005;79(18):11776-87.

Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.

Mandel et al., Recombinant adeno-associated viral vectors as therapeutic agents to treat neurological disorders. Mol Ther. Mar. 2006;13(3):463-83. Epub Jan. 18, 2006.

Manfredsson et al., AAV9: a potential blood-brain barrier buster. Mol Ther. Mar. 2009;17(3):403-5.

Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592. Rasko, John [corrected to Rasko, John JE]; Rustagi, Pradip K [added].

Martin-Duque et al., Direct comparison of the insulating properties of two genetic elements in an adenoviral vector containing two different expression cassettes. Hum Gene Ther. Oct. 2004;15(10):995-1002.

Matalon et al., Adeno-associated virus-mediated aspartoacylase gene transfer to the brain of knockout mouse for canavan disease. Mol Ther. May 2003;7(5 Pt 1):580-7.

Mattan et al., Aspartoacylase deficiency affects early postnatal development of oligodendrocytes and myelination. Neurobiol Dis. Nov. 2010;40(2):432-43. doi: 10.1016/j.nbd.2010.07.003. Epub Jul. 14, 2010.

McBride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.

McCarty et al., Integration of adeno-associated virus (AAV) and recombinant AAV vectors. Annu Rev Genet. 2004;38:819-45.

McCarty et al., Self-complementary recombinant adeno-associated virus (scAAV) vectors promote efficient transduction independently of DNA synthesis. Gene Ther. Aug. 2001;8(16):1248-54.

McCarty, Self-complementary AAV vectors; advances and applications. Mol Ther. Oct. 2008;16(10):1648-56. Epub Aug. 5, 2008.

McGovern, Taking aim at HDL-C. Raising levels to reduce cardiovascular risk. Postgrad Med. Apr. 2005;117(4):29-30, 33-5, 39 passim.

McLean et al., Gene targeted therapeutics for liver disease in alpha-1 antitrypsin deficiency. Biologics. 2009;3:63-75. Epub Jul. 13, 2009.

Meister et al., Sequence-specific inhibition of microRNA- and siRNA-induced RNA silencing. RNA. Mar. 2004;10(3):544-50.

Mingozzi et al., CD8(+) T-cell responses to adeno-associated virus capsid in humans. Nat Med. Apr. 2007;13(4):419-22. Epub Mar. 18, 2007.

Moffett et al., N-Acetylaspartate in the CNS: from neurodiagnostics to neurobiology. Prog Neurobiol. Feb. 2007;81(2):89-131. Epub Jan. 5, 2007.

(56) References Cited

OTHER PUBLICATIONS

Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004;125(2):509-21.
Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.
Mueller et al., In Vivo AAV Delivered Allele Specific shRNA for the Knockdown of Alpha-1 Antitrypsin. Molecular Therapy May 2010;18(1):S22. Abstract 53.
Mueller et al., In Vivo Allele Specific Knockdown of Mutant Alpha-1 Antitrypsin Using Recombinant AAV Delivered shRNA. Molecular Therapy May 2009;17(1):S313. Abstract 817.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.
Mueller et al., The pros and cons of immunomodulatory IL-10 gene therapy with recombinant AAV in a Cftr-/- -dependent allergy mouse model. Gene Ther. Feb. 2009;16(2):172-83. Epub Sep. 25, 2008.
Mueller et al., Using rAAV Delivered miRNAs to Knockdown Misfolded Human Alpha 1 Antitrypsin in a Transgenic Mouse Model. Molecular Therapy May 2010;18(1):S21. Abstract 51.
Nagai et al., Astrocytes expressing ALS-linked mutated SOD1 release factors selectively toxic to motor neurons. Nat Neurosci. May 2007;10(5):615-22.
Nakabayashi et al., Growth of human hepatoma cells lines with differentiated functions in chemically defined medium. Cancer Res. Sep. 1982;42(9):3858-63.
Naldini, Ex vivo gene transfer and correction for cell-based therapies. Nat Rev Genet. May 2011;12(5):301-15. doi: 10.1038/nrg2985. Epub Mar. 29, 2011.
O'Reilly et al., RNA interference-mediated suppression and replacement of human rhodopsin in vivo. Am J Hum Genet. Jul. 2007;81(1):127-35. Epub May 23, 2007.
Papaioannou et al., Efficacy of tribromoethanol anesthesia in mice. Lab Anim Sci. Apr. 1993;43(2):189-92.
Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.
Powell-Braxton et al., A mouse model of human familial hypercholesterolemia: markedly elevated low density lipoprotein cholesterol levels and severe atherosclerosis on a low-fat chow diet. Nat Med. Aug. 1998;4(8):934-8. Erratum in: Nat Med Oct. 1998;4(10):1200.
Propst et al., Prevalence of hepatocellular carcinoma in alpha-1-antitrypsin deficiency. J Hepatol. Dec. 1994;21(6):1006-11.
Ralph et al., Silencing mutant SOD1 using RNAi protects against neurodegeneration and extends survival in an ALS model. Nat Med. Apr. 2005;11(4):429-33. Epub Mar. 13, 2005.
Raoul et al., Lentiviral-mediated silencing of SOD1 through RNA interference retards disease onset and progression in a mouse model of ALS. Nat Med. Apr. 2005;11(4):423-8. Epub Mar. 13, 2005.
Rayner et al., MiR-33 contributes to the regulation of cholesterol homeostasis. Science. Jun. 18, 2010;328(5985):1570-3. doi: 10.1126/science.1189862. Epub May 13, 2010.
Remington's Pharmaceutical Sciences. 1975. Osol et al., Eds. 15th Edition. 1035-1038 and 1570-1580.
Roy et al., Characterization of a family of chimpanzee adenoviruses and development of molecular clones for gene transfer vectors. Hum Gene Ther. May 2004;15(5):519-30.
Sambrook et al, "Molecular Cloning. A Laboratory Manual", 2d ed., Cold Spring Harbor Laboratory, New York (1989).
Scallan et al., Human immunoglobulin inhibits liver transduction by AAV vectors at low AAV2 neutralizing titers in SCID mice. Blood. Mar. 1, 2006;107(5):1810-7. Epub Oct. 25, 2005.
Schnepp et al., Characterization of adeno-associated virus genomes isolated from human tissues. J Virol. Dec. 2005;79(23):14793-803.
Schwarz et al., Designing siRNA that distinguish between genes that differ by a single nucleotide. PLoS Genet. Sep. 8, 2006;2(9):e140, 1307-1318. Epub Jul. 24, 2006.
Seiler et al., Adeno-associated virus types 5 and 6 use distinct receptors for cell entry. Hum Gene Ther. Jan. 2006;17(1):10-9.
Sen et al., Micromanaging vascular biology: tiny microRNAs play big band. J Vasc Res. 2009;46(6):527-40. doi: 10.1159/000226221. Epub Jun. 30, 2009.
Sivasothy et al., Pathogenic alpha 1-antitrypsin polymers are formed by reactive loop-beta-sheet A linkage. J Biol Chem. Oct. 27, 2000;275(43):33663-8.
Sondhi et al., Enhanced survival of the LINCL mouse following CLN2 gene transfer using the rh.10 rhesus macaque-derived adeno-associated virus vector. Mol Ther. Mar. 2007;15(3):481-91. Epub Dec. 19, 2006.
Song et al., Intramuscular administration of recombinant adeno-associated virus 2 alpha-1 antitrypsin (rAAV-SERPINA1) vectors in a nonhuman primate model: safety and immunologic aspects. Mol Ther. Sep. 2002;6(3):329-35.
Soutar et al., Mechanisms of disease: genetic causes of familial hypercholesterolemia. Nat Clin Pract Cardiovasc Med. Apr. 2007;4(4):214-25.
Stein et al., Systemic and central nervous system correction of lysosomal storage in mucopolysaccharidosis type VII mice. J Virol. Apr. 1999;73(4):3424-9.
Storkebaum et al., Treatment of motoneuron degeneration by intracerebroventricular delivery of VEGF in a rat model of ALS. Nat Neurosci. Jan. 2005;8(1):85-92. Epub Nov. 28, 2004.
Tannous, Gaussia luciferase reporter assay for monitoring biological processes in culture and in vivo. Nat Protoc. 2009;4(4):582-91. doi: 10.1038/nprot.2009.28.
Tenenbaum et al., Recombinant AAV-mediated gene delivery to the central nervous system. J Gene Med. Feb. 2004;6 Suppl 1:S212-22.
Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.
Tomar et al., Use of adeno-associated viral vector for delivery of small interfering RNA. Oncogene. Aug. 28, 2003;22(36):5712-5.
Towne et al., Systemic AAV6 delivery mediating RNA interference against SOD1: neuromuscular transduction does not alter disease progression in fALS mice. Mol Ther. Jun. 2008;16(6):1018-25. doi:10.1038/mt.2008.73. Epub Apr. 15, 2008.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Tsai et al., MicroRNA-122, a tumor suppressor microRNA that regulates intrahepatic metastasis of hepatocellular carcinoma. Hepatology. May 2009;49(5):1571-82. doi: 10.1002/hep.22806.
Vandenberghe et al., Heparin binding directs activation of T cells against adeno-associated virus serotype 2 capsid. Nat Med. Aug. 2006;12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vaucheret et al., The action of ARGONAUTE1 in the miRNA pathway and its regulation by the miRNA pathway are crucial for plant development. Genes Dev. May 15, 2004;18(10):1187-97. Epub May 6, 2004.
Veniant et al., Lipoprotein clearance mechanisms in LDL receptor-deficient "Apo-B48-only" and "Apo-B100-only" mice. J Clin Invest. Oct. 15, 1998;102(8):1559-68.
Vermeulen et al., Double-stranded regions are essential design components of potent inhibitors of RISC function. RNA. May 2007;13(5):723-30. Epub Mar. 30, 2007.
Virella-Lowell et al., Enhancing rAAV vector expression in the lung. J Gene Med. Jul. 2005;7(7):842-50.
Waldman et al., Applications of microRNA in cancer: Exploring the advantages of miRNA. Clin Transl Sci. Jun. 2009;2(3):248-9. doi: 10.1111/j.1752-8062.2009.00110.x.
Wang et al., Rescue and replication of adeno-associated virus type 2 as well as vector DNA sequences from recombinant plasmids

(56) References Cited

OTHER PUBLICATIONS containing deletions in the viral inverted terminal repeats: selective encapsidation of viral genomes in progeny virions. J Virol. Mar. 1996;70(3):1668-77.

Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.

Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.

Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.

Wang et al., Vascular endothelial growth factor overexpression delays neurodegeneration and prolongs survival in amyotrophic lateral sclerosis mice. J Neurosci. Jan. 10, 2007;27(2):304-7.

Wu et al., Alpha2,3 and alpha2,6 N-linked sialic acids facilitate efficient binding and transduction by adeno-associated virus types 1 and 6. J Virol. Sep. 2006;80(18):9093-103.

Wu et al., Chronic lumbar catheterization of the spinal subarachnoid space in mice. J Neurosci Methods. Feb. 15, 2004;133(1-2):65-9.

Wu et al., Nerve injection of viral vectors efficiently transfers transgenes into motor neurons and delivers RNAi therapy against ALS. Antioxid Redox Signal. Jul. 2009;11(7):1523-34.

Xia et al., Allele-specific RNAi selectively silences mutant SOD1 and achieves significant therapeutic benefit in vivo. Neurobiol Dis. Sep. 2006;23(3):578-86. Epub Jul. 20, 2006.

Xia et al., Multiple shRNAs expressed by an inducible pol II promoter can knock down the expression of multiple target genes. Biotechniques. Jul. 2006;41(1):64-8.

Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.

Xie et al., Characterization of positioning effect of pol III-shRNA transcription unit in scAAV vector genome on the packaging efficiency and functionality of shRNA silencing. Molecular Therapy. May 2010;18(1): S262. Abstract 671.

Xie et al., MicroRNA regulated tissue specific transduction by rAAV vector. Molecular Therapy. May 2009;17(1): S279. Abstract 732.

Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.

Xie et al., rAAV-mediated delivery of micro RNA scavengers leads to efficient and stable knock-down of cognate micro RNAs, upregulation of their natural target genes and phenotypic changes in mice. Molecular Therapy. May 2010;18(1): S140. Abstract 362.

Yamanaka et al., Astrocytes as determinants of disease progression in inherited amyotrophic lateral sclerosis. Nat Neurosci. Mar. 2008;11(3):251-3. doi: 10.1038/nn2047. Epub Feb. 3, 2008.

Yan et al., Unique biologic properties of recombinant AAV1 transduction in polarized human airway epithelia. J Biol Chem. Oct. 6, 2006;281(40):29684-92. Epub Aug. 9, 2006.

Yang et al., The muscle-specific microRNA miR-1 regulates cardiac arrhythmogenic potential by targeting GJA1 and KCNJ2. Nat Med. Apr. 2007;13(4):486-91. Epub Apr. 1, 2007. Erratum in: Nat Med. Dec. 2011;17(12):1693.

Yu et al., let-7 regulates self renewal and tumorigenicity of breast cancer cells. Cell. Dec. 14, 2007;131(6):1109-23.

Zabner et al., Adeno-associated virus type 5 (AAV5) but not AAV2 binds to the apical surfaces of airway epithelia and facilitates gene transfer. J Virol. Apr. 2000;74(8):3852-8.

Zern et al., A novel SV40-based vector successfully transduces and expresses an alpha 1-antitrypsin ribozyme in a human hepatoma-derived cell line. Gene Ther. Jan. 1999;6(1):114-20.

Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.

Zhong et al., Chimpanzee-derived novel natural variants of aav9: vector development and interrogation of correlations between capsid structure and vector biology. Molecular Therapy. May 2010;18(1): S24. Abstract 58.

Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.

Zolotukhin et al., Production and purification of serotype 1, 2, and 5 recombinant adeno-associated viral vectors. Methods. Oct. 2002;28(2):158-67.

RAAV-BASED COMPOSITIONS AND METHODS

RELATED APPLICATION

This application is a continuation under 35 U.S. C. § 120 of U.S. application Ser. No. 14/952,217, entitled "RAAV-BASED COMPOSITIONS AND METHODS FOR TREATING ALPHA-1 ANTI-TRYPSIN DEFICIENCIES", filed Nov. 25, 2015, which is a continuation under 35 U.S. C. § 120 of U.S. application Ser. No. 14/113,118, entitled "RAAV-BASED COMPOSITIONS AND METHODS FOR TREATING ALPHA-1 ANTI-TRYPSIN DEFICIENCIES" filed Oct. 21, 2013, which is a National Stage filing under 35 U.S.C. § 371 of international application PCT/US2012/034446, filed on Apr. 20, 2012, and entitled "RAAV-BASED COMPOSITIONS AND METHODS FOR TREATING ALPHA-1 ANTI-TRYPSIN DEFICIENCIES," which claims the benefit under 35 U.S.C. § 119(e) to U.S. Provisional Application Ser. No. 61/477,671, entitled "RAAV-BASED COMPOSITIONS AND METHODS FOR TREATING ALPHA-1 ANTI-TRYPSIN DEFICIENCIES" filed on Apr. 21, 2011, the entire content of each application which is incorporated by reference herein.

FEDERALLY SPONSORED RESEARCH

This invention was made with government support under HL069877 and DK032520 awarded by National Institutes of Health. The government has certain rights in the invention.

FIELD OF THE INVENTION

The invention relates to methods and compositions for treating genetic disease using rAAV-based vectors.

BACKGROUND OF THE INVENTION

Numerous diseases are associated with inherited or somatic mutations. In many cases, these mutations are present in the transcript region of genes, the products of which control important physiological functions including, for example, gene expression, cell signaling, tissue structure, and the metabolism and catabolism of various biomolecules. Mutations in these genes, which are often only single nucleotide changes (e.g., non-sense mutations, missense mutations), can have negative effects on the expression, stability and/or function of the gene product resulting in alterations in one or more physiological functions.

A number of different mutations have been identified in the Alpha-1 antitrypsin (AAT) gene. AAT is one of the primary circulating serum anti-proteases in humans. AAT inhibits a variety of serine proteinases, with neutrophil elastase being one of the most physiologically important, as well as inhibiting a number of metalloproteinases and other pro-inflammatory and pro-apoptotic molecules. AAT is normally produced within hepatocytes and macrophages, where hepatocyte-derived AAT forms the bulk of the physiologic reserve of AAT.

Approximately 4% of the North American and Northern European populations possess at least one copy of a mutant allele, known as PI*Z (Z-AAT) which results from a single amino acid substitution of lysine for glutamate at position 342 in the mature protein (position 366 in the precursor protein). In the homozygous state, this mutation leads to severe deficiency of AAT, and can result in two distinct pathologic states: a lung disease which is primarily due to the loss of antiprotease function, and a liver disease (present to a significant degree in approximately 10-15% of patients) due to a toxic gain of function of the Z-AAT mutant protein.

Investigational clinical gene therapy products for gene augmentation of AAT have been developed as potential treatments for lung disease using the recombinant adeno-associated viral (rAAV) vectors. Researchers have also applied genetic technologies in an effort to down-regulate the levels of AAT mRNA. One approach was to utilize hammerhead ribozymes designed to cleave AAT mRNA at a specific site. Another approach involves the use of RNA interference to decrease levels of the mutant mRNA transcript.

SUMMARY OF THE INVENTION

Aspects of the invention relate to improved gene therapy-based methods for treating genetic disease. Some aspects of the invention relate to improved gene therapy compositions and related methodology for treating lung disease and/or liver disease using the recombinant adeno-associated viral vectors. In some embodiments, the methods utilize rAAV (e.g., rAAV9, rAAV2, rAAV1) based vectors for augmenting AAT expression. In some embodiments, compositions and methods are provided for decreasing the expression of Pi*Z mutant AAT protein. In such embodiments, the compositions and methods are useful for halting and/or ameliorating hepatocellular damage and other tissue damage associated with the mutant AAT.

According to some aspects of the invention, the compositions and methods are useful for knocking down PiZ protein while at the same time increasing levels of the M-AAT protein (the wild-type AAT protein). In some embodiments, a non-toxic dual function vector is provided that is capable of knocking-down Z-AAT while augmenting M-AAT. According to some embodiments, methods and compositions for long-term expression of therapeutic miRNAs are provided that utilize the recombinant adeno-associated virus (rAAV) platform. In some embodiments, therapeutic compositions and methods described herein take advantage of the miRNA pathway by altering the seed sequence of natural miRNAs to target the endogenous AAT gene. In some embodiments, the methods are safer and less toxic than shRNA-based approaches.

According to other aspects of the invention, rAAV-based compositions and methods are provided that simultaneously direct silencing agents to the liver to decrease Z-AAT expression and direct gene augmentation to other sites. However, in some embodiments, the liver is an optimal target tissue for augmentation. In some embodiments, a miRNA-based approach is provided to stably down-regulate Z-AAT within hepatocytes. In some embodiments, the approach allows for simultaneous M-AAT gene augmentation from the same rAAV gene delivery vector without serious perturbation of the overall hepatic miRNA profile. In some embodiments, the specific vector used is a systemically delivered rAAV9-capsid derived vector. According to some aspects of the invention, this approach has broad utility in genetic disorders stemming from dominant negative and gain of function mutations as well as for delivering artificial miRNAs to be delivered in conjunction with therapeutic genes.

According to some aspects of the invention, isolated nucleic acids are provided. In some embodiments, the isolated nucleic acids comprise (a) a first region that encodes one or more first miRNAs comprising a nucleic acid having sufficient sequence complementary with an endogenous mRNA of a subject to hybridize with and inhibit expression of the endogenous mRNA, wherein the endogenous mRNA encodes a first protein; and (b) a second region encoding an exogenous mRNA that encodes a second protein, wherein the second protein has an amino acid sequence that is at least 85% identical to the first protein, wherein the one or more first miRNAs do not comprise a nucleic acid having sufficient sequence complementary to hybridize with and inhibit expression of the exogenous mRNA, and wherein the first region is positioned within an untranslated portion of the second region. In some embodiments, the untranslated portion is an intron. In some embodiments, the first region is between the first codon of the exogenous mRNA and 1000 nucleotides upstream of the first codon.

In some embodiments, the isolated nucleic acids comprise (a) a first region encoding one or more first miRNAs comprising a nucleic acid having sufficient sequence complementary with an endogenous mRNA of a subject to hybridize with and inhibit expression of the endogenous mRNA, wherein the endogenous mRNA encodes a first protein; and (b) a second region encoding an exogenous mRNA that encodes a second protein, wherein the second protein has an amino acid sequence that is at least 85% identical to the first protein, wherein the one or more first miRNAs do not comprise a nucleic acid having sufficient sequence complementary to hybridize with and inhibit expression of the exogenous mRNA, and wherein the first region is positioned downstream of a portion of the second region encoding the poly-A tail of the exogenous mRNA.

In some embodiments, the isolated nucleic acids further comprise a third region encoding a one or more second miRNAs comprising a nucleic acid having sufficient sequence complementary to hybridize with and inhibit expression of the endogenous mRNA, wherein the third region is positioned within an untranslated portion of the second region. In some embodiments, the untranslated portion is an intron. In some embodiments, the first region is between the last codon of the exogenous mRNA and a position 1000 nucleotides downstream of the last codon. In some embodiments, the third region is between the first codon of the exogenous mRNA and a position 1000 nucleotides upstream of the first codon.

In some embodiments of the isolated nucleic acids, the first region encodes two first miRNAs. In some embodiments, the first region encodes three first miRNAs. In some embodiments, the third region encodes two second miRNAs. In some embodiments, the third region encodes three second miRNAs. In some embodiments, one or more of the first miRNAs have the same nucleic acid sequence as one or more of the second miRNAs. In some embodiments, each of the first miRNAs has the same nucleic acid sequence as one of the second miRNAs. In some embodiments, the second protein has an amino acid sequence that is at least 90% identical to the first protein. In some embodiments, the second protein has an amino acid sequence that is at least 95% identical to the first protein. In some embodiments, the second protein has an amino acid sequence that is at least 98% identical to the first protein. In some embodiments, the second protein has an amino acid sequence that is at least 99% identical to the first protein. In some embodiments, the second protein has an amino acid sequence that is 100% identical to the first protein.

In some embodiments of the isolated nucleic acids, the first protein is Alpha 1-Antitrypsin (AAT) protein. In some embodiments, the AAT protein is a human AAT protein. In some embodiments, the AAT protein has sequence as set forth in SEQ ID NO: 1 or 2 or one or more mutations thereof as identified in Table 1, e.g. SEQ ID NO: 3 or 4. In some embodiments, the first mRNA comprises a nucleic acid encoded by a sequence as set forth in SEQ ID NOS: 5-16. In some embodiments, the one or more miRNAs have a nucleic acid sequence encoded by a sequence from the group consisting of SEQ ID NOS: 17-19 and 21-23. In some embodiments of the isolated nucleic acids, the exogenous mRNA has one or more silent mutations compared with the endogenous mRNA. In some embodiments, the exogenous mRNA has a nucleic acid sequence encoded by a sequence as set forth in SEQ ID NO: 20.

In some embodiments, the isolated nucleic acids further comprise an inverted terminal repeats (ITR) of an AAV serotypes selected from the group consisting of: AAV1, AAV2, AAV5, AAV6, AAV6.2, AAV7, AAV8, AAV9, AAV10, AAV11 and variants thereof. In some embodiments, the isolated nucleic acids further comprise a promoter operably linked with the region(s) encoding the one or more first miRNAs, the exogenous mRNA, and/or the one or more second miRNAs. In certain embodiments, the promoter is a tissue-specific promoter. In certain embodiments, the promoter is a β-actin promoter.

According to some aspects of the invention, recombinant Adeno-Associated Viruses (AAVs) are provided that comprise any of the isolated nucleic acids disclosed herein. In some embodiments, the recombinant AAVs further comprise one or more capsid proteins of one or more AAV serotypes selected from the group consisting of: AAV1, AAV2, AAV3, AAV4, AAV5, AAV6, AAV7, AAV8, AAV9, AAV10, AAV11 and variants thereof.

According to some aspects of the invention, compositions are provided that comprise any of the isolated nucleic acids disclosed herein. According to some aspects of the invention, compositions are provided that comprise any of the recombinant AAVs disclosed herein. In some embodiments, the compositions further comprise a pharmaceutically acceptable carrier.

According to some aspects of the invention, kits are provided that comprise one or more containers housing a composition, isolated nucleic acid or rAAV of the invention. In some embodiments, the kits further comprise written instructions for administering an rAAV to a subject.

According to some aspects of the invention, methods are provided for expressing Alpha 1-Antitrypsin (AAT) protein in a subject. In some embodiments, the methods comprise administering to a subject an effective amount of any recombinant Adeno-Associated Virus (rAAV) disclosed herein. In some embodiments, the rAAV is administered with a pharmaceutically acceptable carrier.

In some embodiments of the methods, the subject has or suspected of having an Alpha 1-Antitrypsin deficiency. In certain embodiments, the subject has a mutation in an AAT gene. In certain embodiments, the mutation encodes a mutant AAT protein. In some embodiments, the methods further comprise determining that the subject has the mutation. In certain embodiments, the mutation is a mutation listed in Table 1. In certain embodiments, the mutation is a missense mutation. In certain embodiments, the mutation results in a glutamate to lysine substitution at amino acid position 366 according to the amino acid sequence set forth as SEQ ID NO: 3. In certain embodiments, the mutant AAT protein fails to fold properly.

In some embodiments of the methods, the effective amount of rAAV is $10^{10}$, $10^{11}$, $10^{12}$, or $10^{13}$ genome copies. In some embodiments, administering is performed intravascularly, intravenously, intrathecally, intraperatoneally, intramuscularly, subcutaneously or intranasally. In certain embodiments, administering is performed by injection into the hepatic portal vein.

In some embodiments of the methods, administering is performed ex vivo by isolating cells or tissue from a subject, contacting the cell or tissue with an effective amount of an rAAV, thereby producing transfected cells or tissue, and administering the transfected cells or tissue to the subject. In certain embodiments, the tissue is adipose tissue. In certain embodiments, the cells are stem cells derived from adipose tissue. In some embodiments, administering the transfected cells is performed intravascularly, intravenously, intrathecally, intraperatoneally, intramuscularly, subcutaneously or intranasally. In certain embodiments, administering the transfected cells is performed by transplantation of transfected cells into a target tissue. In certain embodiments, the target tissue is lung or liver In some embodiments of the methods, the subject is a mouse, a rat, a rabbit, a dog, a cat, a sheep, a pig, a non-human primate or a human. In certain embodiments, the subject is a human.

In some embodiments of the methods, after administration of the rAAV the level of expression of the first protein is determined in the subject. In some embodiments, after administration of the rAAV the level of expression of the second protein is determined in the subject. In some embodiments, administering is performed on two or more occasions. In certain embodiments, the level of the first protein and/or the level of the second protein in the subject are determined after at least one administration.

In some embodiments of the methods, the serum level of the first protein in the subject is reduced by at least 85% following administration of the rAAV. In some embodiments, the serum level of the first protein in the subject is reduced by at least 90% following administration of the rAAV. In some embodiments, the serum level of the first protein in the subject is reduced by at least 95% following administration of the rAAV. In some embodiments, the serum level of the first protein in the subject is reduced by at least 85% within 2 weeks following administration of the rAAV. In some embodiments, the serum level of the first protein in the subject is reduced by at least 90% within 2 weeks following administration of the rAAV. In some embodiments, the serum level of the first protein in the subject is reduced by at least 85% within 4 weeks of administration of the rAAV. In some embodiments, after 7 weeks of administration of the rAAV, the serum level of the first protein is at a level of at least 50% compared with the serum level of the first protein prior to administration of the rAAV. In some embodiments, after 7 weeks of administration of the rAAV, the serum level of the first protein is at a level of at least 75% compared with the serum level of the first protein prior to administration of the rAAV.

In some embodiments of the methods, after administration of the rAAV at least one clinical outcome parameter associated with the AAT deficiency is evaluated in the subject. In some embodiments, the at least one clinical outcome parameter evaluated after administration of the rAAV is compared with the at least one clinical outcome parameter determined prior to administration of the rAAV to determine effectiveness of the rAAV, wherein an improvement in the clinical outcome parameter after administration of the rAAV indicates effectiveness of the rAAV. In some embodiments, the clinical outcome parameter is selected from the group consisting of: serum levels of the first protein, serum levels of the second protein, presence of intracellular AAT globules, presence of inflammatory foci, breathing capacity, cough frequency, phlegm production, frequency of chest colds or pneumonia, and tolerance for exercise. In some embodiments, the intracellular AAT globules or inflammatory foci are evaluated in lung tissue or liver tissue.

BRIEF DESCRIPTION OF THE DRAWINGS

(FIG. 1A) Culture media was harvested at 24, 48 and 72 hours and was analyzed for the AAT concentration by ELISA. (FIG. 1B) At 72 hours cells were harvested and lysed for AAT concentration by ELISA. *<0.05 as determined by a two-way unpaired student t-test.

(FIG. 3G) Quantitative pixel image analysis of whole liver sections was performed by comparing pixel counts of PASD-positive globules in GFP controls (N=7) to pixel counts of PASD-positive globules in intronic-3×miR (N=7).

(FIG. 6A) Serums from each cohort were collected on a weekly basis and were used to assess Z-AAT concentration by ELISA. (FIG. 6B) ATT from liver lysates of mice was analyzed by immunoblot after monomer and polymer separation. The 52 kDa Z-AAT was from livers processed and separated into a monomer and polymer pool. Densitometric analysis was performed for the (FIG. 6C) monomer and (FIG. 6D) polymer pools using Image J software. Baseline serums and those collected two weeks-post rAAV9 delivery were used to analyze liver function as determined by (FIG. 6E) ALT and (FIG. 6F) AST concentration. Data is expressed as group means+SEM. *<0.05 as determined by a two-way unpaired student ¬t-test comparing rAAV9 cohorts vs. baseline.

Figure 7A:
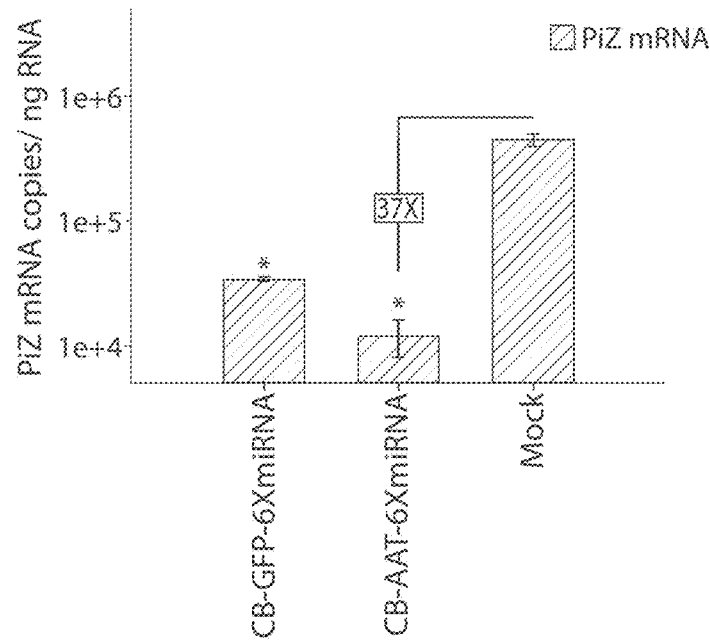
Figure 7B:
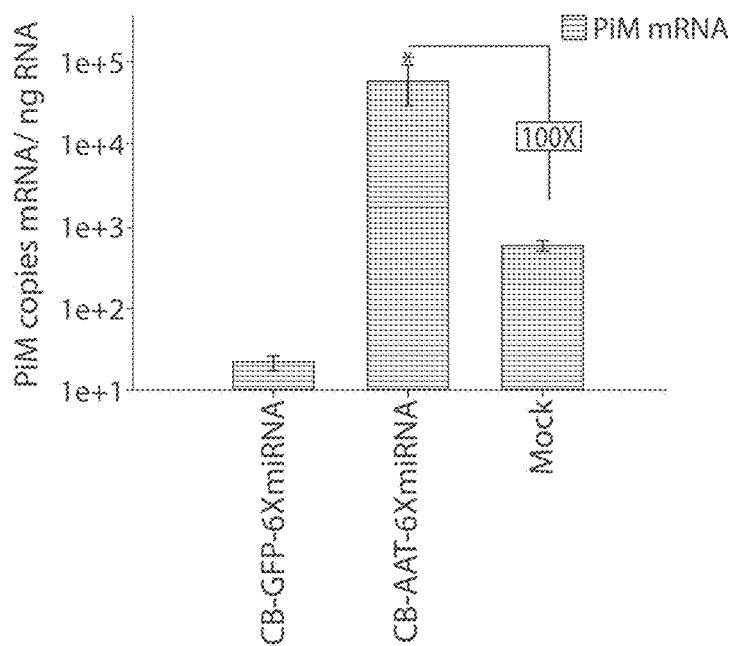

FIGS. 7A-7B In vitro assessment of dual-function proviral plasmid. HEK-293 cells were contrasfected with human Z-AAT plasmid and either the Double-6xmiR-CB-AAT plasmid, a GFP or PBS control. Cells were processed for RNA at 72 hours and were analyzed for (FIG. 7A) PiZ-mRNA or (FIG. 7B) PiM mRNA with qRT-PCR. Data is expressed as group means+SEM (n=6). *<0.05 as determined by a two-way unpaired student t-test.

Figure 8B:
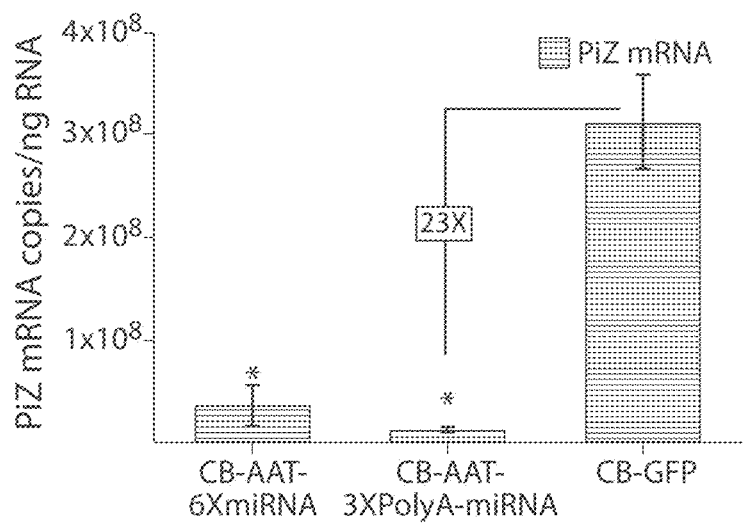
Figure 8C:
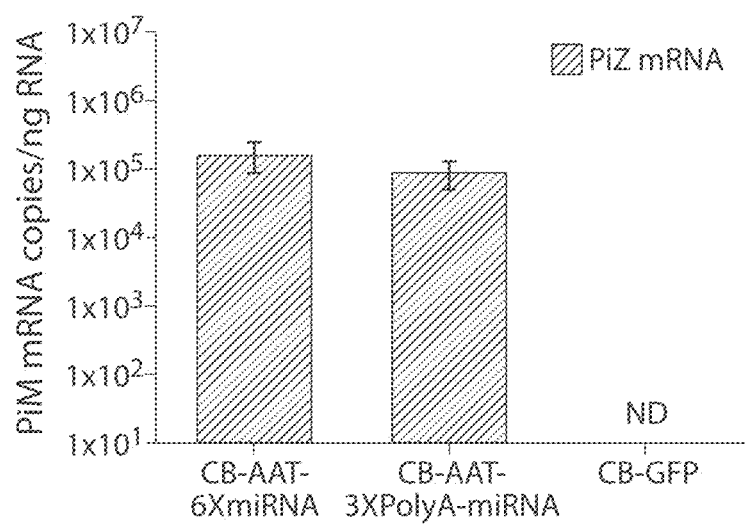

FIGS. 8A-8C In vivo knockdown of Z-AAT with simultaneous augmentation of M-AAT after rAAV9 dual function vector delivery. Transgenic mice expressing the human PiZ allele were injected with $1 \times 10^{12}$ vector particles or rAAV9 expressing miRNAs against AAT and a de-targeted cMyc tagged wiltype M-AAT cDNA under the control of the hybrid chicken beta-actin promoter via the tail vein. (FIG. 8A) Serum from each cohort was collected on a weekly basis and was used to assess Z-AAT concentration by Z-AAT specific ELISA and M-AAT levels by cMyc ELISA. Total RNA from mouse livers was used to assay for the presence of the either (FIG. 8) Z-AAT mRNA or (FIG. 8C) M-AAT mRNA by qRT-PCR. Data is expressed as group means+SEM (n=6). *<0.05 as determined by a two-way unpaired student t-test.

Figure 9:
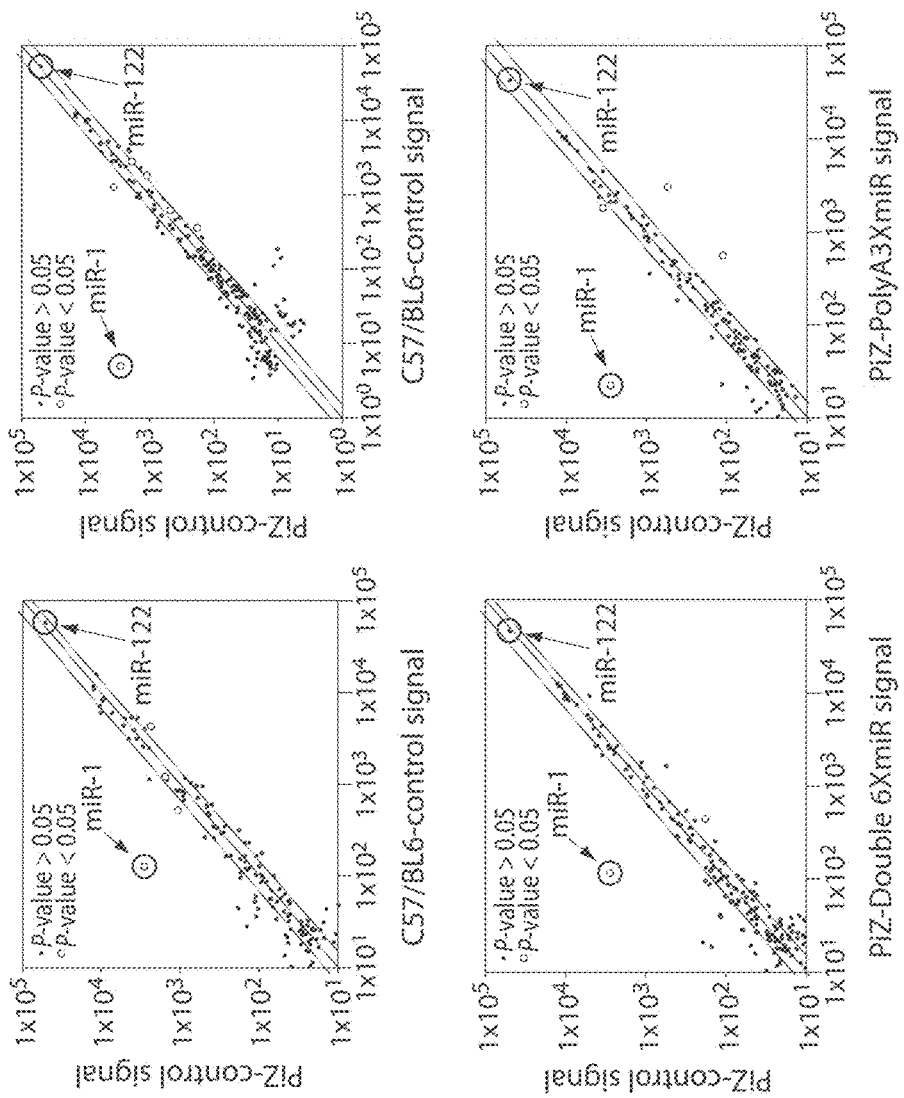

FIG. 9 Artificial miRNA have minimal impact on endogenous miRNA liver profiles. Liver RNA was harvested 3 months post delivery from animals injected with the following vectors: intronic-3xmiR-GFP, PolyA-3xmiR-GFP, Double-6xmiR-GFP, CB-GFP along with RNA form untreated PiZ mice and wiltype C57Bl6 mice was used to run a miRNA microarray. Each group consisted of 5 mouse RNA samples and was run independently with a single color (Cy5) microarray.

DETAILED DESCRIPTION OF CERTAIN EMBODIMENTS OF THE INVENTION

Aspects of the invention relate to improved gene therapy compositions and related methods for treating Alpha-1 Antitrypsin (AAT, also sometimes called SERPINA1) deficiencies using the recombinant adeno-associated viral (rAAV) vectors. In some embodiments, a non-toxic dual function vector is provided that is capable of knocking-down mutant AAT while expressing wild-type AAT. The rAAV-based vectors and related methods provide for long-term expression of therapeutic miRNAs and expression of wild-type protein. According to other aspects, rAAV-based compositions and methods are provided that simultaneously direct silencing agents to the liver to decrease Z-AAT expression and direct gene expression to other sites (e.g., lung tissue). In some embodiments, compositions and methods are provided that are useful for treating the AAT deficiency by knocking down PiZ protein (a mutant AAT protein) while at the same time increasing levels of the M-AAT protein (the wild-type AAT protein). It will be appreciated that the rAAV-based therapeutic approaches disclosed herein can be applied to other gain-of-function or dominant-negative genetic disorders such as Huntington's disease, which previously have not been amiable to a single vector gene therapy approach.

Certain rAAV vectors provided herein incorporate miRNA sequences targeting the AAT gene while driving the expression of hardened wild-type AAT gene (a wild-type AAT gene that is not targeted by the miRNA), thus achieving concomitant mutant AAT knockdown e.g., in the liver, with increased expression of wildtype AAT. In one embodiment, transgenic mice expressing the human PiZ allele were injected with control or dual function rAAV9 vectors expressing both miRNAs and a hardened AAT gene with a cMyc tag. In this embodiment, serum PiZ levels were consistently knocked down by an average of 80% from baseline levels with the knockdown being stable and persistent over a 13 week period. In one embodiment, cohorts receiving dual function vectors exhibited knockdown of PiZ AAT while secreting increased serum levels of wild-type AAT as determined by a PiZ and PiM specific ELISAs. In this embodiment, liver histology revealed significantly decreased globular accumulation of misfolded PiZ AAT in hepatocytes along with a reduction in inflammatory infiltrates when compared to controls.

In one embodiment, global miRNA expression profiles of the liver were minimally affected by artificial miRNAs delivered via rAAV, with only a few miRNAs showing statistically significant differences. In one embodiment, a difference was seen in miR-1 which was reduced in PiZ transgenic mice receiving rAAV vectors to normal levels seen in wild-type B6 mice. In one embodiment, the levels of miR-122 were unaffected in all mice receiving rAAVs expressing miRNA targeting the AAT gene. Accordingly, in some embodiments, dual function rAAV vectors are effective at knocking down PIZ AAT while simultaneously augmenting wild-type AAT without disturbing endogenous miRNA liver profiles.

Alpha-1 Antitrypsin Deficiency

Alpha-1 antitrypsin (AAT), also known in the art as serpin peptidase inhibitor, clade A (SERPINA1), is a protein that functions as proteinase (protease) inhibitor. AAT is mainly produced in the liver, but functions in the lungs and liver, primarily. As used herein the term, "alpha-1 antitrypsin deficiency" refers to a condition resulting from a deficiency of functional AAT in a subject. In some embodiments, a subject having an AAT deficiency produces insufficient amounts of alpha-1 antitrypsin. In some embodiments, a subject having an AAT deficiency produces a mutant AAT. In some embodiments, insufficient amounts of AAT or expression of mutant AAT results in damage to a subject's lung and/or liver. In some embodiments, the AAT deficiency leads to emphysema and/or liver disease. Typically, AAT deficiencies result from one or more genetic defects in the AAT gene. The one or more defects may be present in one or more copies (e.g., alleles) of the AAT gene in a subject. Typically, AAT deficiencies are most common among Europeans and North Americans of European descent. However, AAT deficiencies may be found in subjects of other descents as well.

Subjects (e.g., adult subjects) with severe AAT deficiencies are likely to develop emphysema. Onset of emphysema often occurs before age 40 in human subjects having AAT deficiencies. Smoking can increase the risk of emphysema in subjects having AAT deficiencies. Symptoms of AAT deficiencies include shortness of breath, with and without exertion, and other symptoms commonly associated with chronic obstructive pulmonary disease (COPD). Other symptoms of AAT deficiencies include symptoms of severe liver disease (e.g., cirrhosis), unintentional weight loss, and wheezing. A physical examination may reveal a barrel-shaped chest, wheezing, or decreased breath sounds in a subject who has an AAT deficiency.

The following exemplary tests may assist with diagnosing a subject as having an AAT deficiency: an alpha-1 antitrypsin blood test, examination of arterial blood gases, a chest x-ray, a CT scan of the chest, genetic testing, and lung function test. In some cases, a subject having or suspected of having an AAT deficiency is subjected to genetic testing to detect the presence of one or more mutations in the AAT gene. In some embodiments, one or more of the mutations listed in Table 1 are detected in the subject.

In some cases, a physician may suspect that a subject has an AAT deficiency if the subject has emphysema at an early age (e.g., before the age of 45), emphysema without ever having smoked or without ever having been exposed to toxins, emphysema with a family history of an AAT deficiency, liver disease or hepatitis when no other cause can be found, liver disease or hepatitis and a family history of an AAT deficiency.

In some embodiments, alpha-1 antitrypsin deficiency can result in two distinct pathologic states: a lung disease which is primarily due to the loss of anti-protease function, and a liver disease due to a toxic gain of function of the mutant AAT protein (e.g., mutant PiZ-AAT). For example, since mutant AAT-PiZ exhibits a gain-of-function hepatocellular toxicity accumulating in the endoplasmic reticulum, therapies aimed at decreasing AAT-PiZ mRNA levels may ameliorate or even reverse the liver pathology. In addition, increased secretion of functional AAT protein protects the lungs from neutrophil elastase and associated proteolytic enzymes. Applicants have developed several rAAV vectors that provide for delivery of microRNAs targeted against mutant AAT, within the same proviral cassette as a gene encoding wild-type AAT. In some embodiments, the microRNAs are delivered using rAAV vectors that have previously been used in clinical trials.

Isolated Nucleic Acids

In general, the invention provides isolated nucleic acids, which may be rAAV vectors, useful for treating genetic disease. The isolated nucleic acids typically comprise one or more regions that encode one or more inhibitory RNAs that target an endogenous mRNA of a subject. The isolated nucleic acids also typically comprise one or more regions that encode one or more exogenous mRNAs. The protein(s) encoded by the one or more exogenous mRNAs may or may not be different in sequence composition than the protein(s) encoded by the one or more endogenous mRNAs. For example, the one or more endogenous mRNAs may encode a wild-type and mutant version of a particular protein, such as may be the case when a subject is heterozygous for a particular mutation, and the exogenous mRNA may encode a wild-type mRNA of the same particular protein. In this case, typically the sequence of the exogenous mRNA and endogenous mRNA encoding the wild-type protein are sufficiently different such that the exogenous mRNA is not targeted by the one or more inhibitory RNAs. This may be accomplished, for example, by introducing one or more silent mutations into the exogenous mRNA such that it encodes the same protein as the endogenous mRNA but has a different nucleic acid sequence. In this case, the exogenous mRNA may be referred to as "hardened." Alternatively, the inhibitory RNA (e.g. miRNA) can target the 5' and/or 3' untranslated regions of the endogenous mRNA. These 5' and/or 3' regions can then be removed or replaced in the exogenous mRNA such that the exogenous mRNA is not targeted by the one or more inhibitory RNAs.

In another example, the one or more endogenous mRNAs may encode only mutant versions of a particular protein, such as may be the case when a subject is homozygous for a particular mutation, and the exogenous mRNA may encode a wild-type mRNA of the same particular protein. In this case, the sequence of the exogenous mRNA may be hardened as described above, or the one or more inhibitory RNAs may be designed to discriminate the mutated endogenous mRNA from the exogenous mRNA.

In some cases, the isolated nucleic acids typically comprise a first region that encodes one or more first inhibitory RNAs (e.g., miRNAs) comprising a nucleic acid having sufficient sequence complementary with an endogenous mRNA of a subject to hybridize with and inhibit expression of the endogenous mRNA, in which the endogenous mRNA encodes a first protein. The isolated nucleic acids also typically include a second region encoding an exogenous mRNA that encodes a second protein, in which the second protein has an amino acid sequence that is at least 85% identical to the first protein, in which the one or more first inhibitory RNAs do not comprise a nucleic acid having sufficient sequence complementary to hybridize with and inhibit expression of the exogenous mRNA. For example, the first region may be positioned at any suitable location. The first region may be positioned within an untranslated portion of the second region. The first region may be positioned in any untranslated portion of the nucleic acid, including, for example, an intron, a 5' or 3' untranslated region, etc.

In some cases, it may be desirable to position the first region upstream of the first codon of the exogenous mRNA. For example, the first region may be positioned between the first codon of the exogenous mRNA and 2000 nucleotides upstream of the first codon. The first region may be positioned between the first codon of the exogenous mRNA and 1000 nucleotides upstream of the first codon. The first region may be positioned between the first codon of the exogenous mRNA and 500 nucleotides upstream of the first codon. The first region may be positioned between the first codon of the exogenous mRNA and 250 nucleotides upstream of the first codon. The first region may be positioned between the first codon of the exogenous mRNA and 150 nucleotides upstream of the first codon.

In some cases, the first region may be positioned downstream of a portion of the second region encoding the poly-A tail of the exogenous mRNA. The first region may be between the last codon of the exogenous mRNA and a position 2000 nucleotides downstream of the last codon. The first region may be between the last codon of the exogenous mRNA and a position 1000 nucleotides downstream of the last codon. The first region may be between the last codon of the exogenous mRNA and a position 500 nucleotides downstream of the last codon. The first region may be between the last codon of the exogenous mRNA and a position 250 nucleotides downstream of the last codon. The first region may be between the last codon of the exogenous mRNA and a position 150 nucleotides downstream of the last codon.

The nucleic acid may also comprise a third region encoding a one or more second inhibitory RNAs (e.g., miRNAs) comprising a nucleic acid having sufficient sequence complementary to hybridize with and inhibit expression of the endogenous mRNA. As with the first region, the third region may be positioned at any suitable location. For example, the third region may be positioned in an untranslated portion of the second region, including, for example, an intron, a 5' or 3' untranslated region, etc. The third region may be positioned upstream of a portion of the second region encoding the first codon of the exogenous mRNA. The third region may be positioned downstream of a portion of the second region encoding the poly-A tail of the exogenous mRNA. In some cases, when the first region is positioned upstream of the first codon, the third region is positioned downstream of the portion of the second region encoding the poly-A tail of the exogenous mRNA, and vice versa.

In some cases, the first region and third regions encode the same set of one or more inhibitory RNAs (e.g., miRNAs). In other cases, the first region and third regions encode a different set of one or more inhibitory RNAs (e.g., miRNAs). In some cases, the one or more inhibitory RNAs (e.g., miRNAs) encoded by the first region target one or more of the same genes as the one or more inhibitory RNAs (e.g., miRNAs) encoded by the third region. In some cases, the one or more inhibitory RNAs (e.g., miRNAs) encoded by the first region do not target any of the same genes as the one or more inhibitory RNAs (e.g., miRNAs) encoded by the third region. It is to be appreciated that inhibitory RNAs (e.g., miRNAs) which target a gene have sufficient complementarity with the gene to bind to and inhibit expression (e.g., by degradation or inhibition of translation) of the corresponding mRNA.

The first and third regions may also encode a different number of inhibitory RNAs (e.g., miRNAs). For example, the first region and third regions may independently encode 1, 2, 3, 4, 5, 6 or more inhibitory RNAs (e.g., miRNAs). The first and third regions are not limited to comprising any one particular inhibitory RNA, and may include, for example, a miRNA, an shRNA, a TuD RNA, a microRNA sponge, an antisense RNA, a ribozyme, an aptamer, or other appropriate inhibitory RNA. In some cases, the first region and/or third region comprises one or more miRNAs. The one or more miRNAs may comprise a nucleic acid sequence encoded by a sequence selected from the group consisting of SEQ ID NOS: 17-19 and 21-23.

As disclosed herein, the second protein may have an amino acid sequence that is at least 85% identical to the first protein. Accordingly, the second protein may have an amino acid sequence that is at least 88%, at least 90%, at least 95%, at least 98%, at least 99% or more identical to the first protein. In some case, the second protein differs from the first protein by 1, 2, 3, 4, 5, 6, 7, 8, 9, 10 or more amino acids. In some cases, one or more of the differences between the first protein and second protein are conservative amino acid substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Accordingly, conservative amino acid substitutions may provide functionally equivalent variants, or homologs of an endogenous protein.

It should be appreciated that in some cases the second protein may be a marker protein (e.g., a fluorescent protein, a fusion protein, a tagged protein, etc.). Such constructs may be useful, for example, for studying the distribution of the encoded proteins within a cell or within a subject and are also useful for evaluating the efficiency of rAAV targeting and distribution in a subject.

In some embodiments of the isolated nucleic acids, the first protein is alpha-1 antitrypsin (AAT) protein. An exemplary sequence of a wild-type AAT is provided at SEQ ID NO: 1 or 2. Accordingly, in some cases, the endogenous mRNA may comprise the RNA sequence specified by the sequence set forth in SEQ ID NO: 5. The endogenous mRNA may comprise the RNA sequence as specified by any one of the sequences set forth in SEQ ID NOS: 6-16. In some cases, the AAT protein is a human AAT protein. The AAT protein may have a sequence as set forth in SEQ ID NO: 1 or 2 or one or more mutations thereof as identified in Table 1, e.g. SEQ ID NO: 3 or 4. The exogenous mRNA may have one or more silent mutations compared with the endogenous mRNA. The exogenous mRNA may comprise the RNA sequence specified by the sequence set forth in SEQ ID NO: 20. The exogenous mRNA sequence may or may not encode a peptide tag (e.g., a myc tag, a his-tag, etc.) linked to the encoded protein. Often, in a construct used for clinical purposes, the exogenous mRNA sequence does not encode a peptide tag linked to the encoded protein.

As described further below, the isolated nucleic acids may comprise inverted terminal repeats (ITR) of an AAV serotypes selected from the group consisting of: AAV1, AAV2, AAV5, AAV6, AAV6.2, AAV7, AAV8, AAV9, AAV10, AAV11 and variants thereof. The isolated nucleic acids may also include a promoter operably linked with the one or more first inhibitory RNAs, the exogenous mRNA, and/or the one or more second inhibitory RNAs. The promoter may be tissue-specific promoter, a constitutive promoter or inducible promoter.

TABLE 1

Mutations in Human AAT - Entrez Gene ID: 5265

| Chr. position | mRNA position | dbSNP rs# cluster id | Function | dbSNP allele | Protein residue | Codon position | Amino acid position |
|---|---|---|---|---|---|---|---|
| 94844794 | 1822 | rs78787657 | missense | A | Lys [K] | 1 | 417 |
|  |  |  | contig reference | C | Gln [Q] | 1 | 417 |
| 94844797 | 1819 | rs3191200 | missense | C | Pro [P] | 1 | 416 |
|  |  |  | contig reference | A | Thr [T] | 1 | 416 |
| 94844842 | 1774 | rs17850837 | missense | A | Lys [K] | 1 | 401 |
|  |  |  | contig reference | C | Gln [Q] | 1 | 401 |
| 94844843 | 1773 | rs1303 | missense | C | Asp [D] | 3 | 400 |
|  |  |  | contig reference | A | Glu [E] | 3 | 400 |
| 94844855 | 1761 | rs13170 | synonymous | T | Phe [F] | 3 | 396 |
|  |  |  | contig reference | C | Phe [F] | 3 | 396 |
| 94844866 | 1750 | rs61761869 | missense | T | Ser [S] | 1 | 393 |
|  |  |  | contig reference | C | Pro [P] | 1 | 393 |
| 94844887 | 1729 | rs12233 | missense | T | Ser [S] | 1 | 386 |
|  |  |  | contig reference | C | Pro [P] | 1 | 386 |
| 94844912 | 1704 | rs28929473 | missense | T | Phe [F] | 3 | 377 |
|  |  |  | contig reference | A | Leu [L] | 3 | 377 |

TABLE 1-continued

Mutations in Human AAT - Entrez Gene ID: 5265

| Chr. position | mRNA position | dbSNP rs# cluster id | Function | dbSNP allele | Protein residue | Codon position | Amino acid position |
|---|---|---|---|---|---|---|---|
| 94844926 | 1690 | rs12077 | missense | T | Trp [W] | 1 | 373 |
| | | | contig reference | G | Gly [G] | 1 | 373 |
| 94844942 | 1674 | rs1050520 | synonymous | G | Lys [K] | 3 | 367 |
| | | | contig reference | A | Lys [K] | 3 | 367 |
| 94844947 | 1669 | rs28929474 | missense | A | Lys [K] | 1 | 366 |
| | | | contig reference | G | Glu [E] | 1 | 366 |
| 94844954 | 1662 | rs1050469 | synonymous | G | Thr [T] | 3 | 363 |
| | | | contig reference | C | Thr [T] | 3 | 363 |
| 94844957 | 1659 | rs1802961 | synonymous | T | Leu [L] | 3 | 362 |
| | | | contig reference | G | Leu [L] | 3 | 362 |
| 94844959 | 1657 | rs1131154 | missense | A | Met [M] | 1 | 362 |
| | | | contig reference | C | Leu [L] | 1 | 362 |
| 94844960 | 1656 | rs13868 | synonymous | A | Val [V] | 3 | 361 |
| | | | contig reference | G | Val [V] | 3 | 361 |
| 94844961 | 1655 | rs1131139 | missense | C | Ala [A] | 2 | 361 |
| | | | contig reference | T | Val [V] | 2 | 361 |
| 94844962 | 1654 | rs72555357 | frame shift | | | 1 | 361 |
| | | | contig reference | G | Val [V] | 1 | 361 |
| 94844965 | 1651 | rs1802959 | missense | A | Thr [T] | 1 | 360 |
| | | | contig reference | G | Ala [A] | 1 | 360 |
| 94844972 | 1644 | rs10427 | synonymous | C | Val [V] | 3 | 357 |
| | | | contig reference | G | Val [V] | 3 | 357 |
| 94844975 | 1641 | rs9630 | synonymous | T | Ala [A] | 3 | 356 |
| | | | contig reference | C | Ala [A] | 3 | 356 |
| 94844977 | 1639 | rs67216923 | frame shift | | | 1 | 356 |
| | | | frame shift | (15 bp) | | 1 | 356 |
| | | | contig reference | G | Ala [A] | 1 | 356 |
| 94845814 | 1625 | rs72555374 | frame shift | | | 2 | 351 |
| | | | contig reference | T | Leu [L] | 2 | 351 |
| 94845845 | 1594 | rs28929471 | missense | A | Asn [N] | 1 | 341 |
| | | | contig reference | G | Asp [D] | 1 | 341 |
| 94845893 | 1546 | rs1802962 | missense | T | Cys [C] | 1 | 325 |
| | | | contig reference | A | Ser [S] | 1 | 325 |
| 94845902 | 1537 | rs55704149 | missense | T | Tyr [Y] | 1 | 322 |
| | | | contig reference | G | Asp [D] | 1 | 322 |
| 94845914 | 1525 | rs117001071 | missense | T | Ser [S] | 1 | 318 |
| | | | contig reference | A | Thr [T] | 1 | 318 |
| 94845917 | 1521 | rs35624994 | frame shift | | Ser [S] | 3 | 316 |
| | | | frame shift | C | Ser [S] | 3 | 316 |
| | | | contig reference | CA | Ser [S] | 3 | 316 |
| 94847218 | 1480 | rs1802963 | nonsense | T | xxx [X] | 1 | 303 |
| | | | contig reference | G | Glu [E] | 1 | 303 |
| 94847262 | 1436 | rs17580 | missense | T | Val [V] | 2 | 288 |
| | | | contig reference | A | Glu [E] | 2 | 288 |
| 94847285 | 1413 | rs1049800 | synonymous | C | Asp [D] | 3 | 280 |
| | | | contig reference | T | Asp [D] | 3 | 280 |
| 94847306 | 1392 | rs2230075 | synonymous | T | Thr [T] | 3 | 273 |
| | | | contig reference | C | Thr [T] | 3 | 273 |
| 94847351 | 1347 | rs34112109 | synonymous | A | Lys [K] | 3 | 258 |
| | | | contig reference | G | Lys [K] | 3 | 258 |
| 94847357 | 1341 | rs8350 | missense | G | Trp [W] | 3 | 256 |
| | | | contig reference | T | Cys [C] | 3 | 256 |
| 94847386 | 1312 | rs28929470 | missense | T | Cys [C] | 1 | 247 |
| | | | contig reference | C | Arg [R] | 1 | 247 |
| 94847407 | 1291 | rs72552401 | missense | A | Met [M] | 1 | 240 |
| | | | contig reference | G | Val [V] | 1 | 240 |
| 94847415 | 1283 | rs6647 | missense | C | Ala [A] | 2 | 237 |
| | | | contig reference | T | Val [V] | 2 | 237 |
| 94847452 | 1246 | rs11558264 | missense | C | Gln [Q] | 1 | 225 |
| | | | contig reference | A | Lys [K] | 1 | 225 |
| 94847466 | 1232 | rs11558257 | missense | T | Ile [I] | 2 | 220 |
| | | | contig reference | G | Arg [R] | 2 | 220 |
| 94847475 | 1223 | rs11558265 | missense | C | Thr [T] | 2 | 217 |
| | | | contig reference | A | Lys [K] | 2 | 217 |
| 94849029 | 1119 | rs113813309 | synonymous | T | Asn [N] | 3 | 182 |
| | | | contig reference | C | Asn [N] | 3 | 182 |
| 94849053 | 1095 | rs72552402 | synonymous | T | Thr [T] | 3 | 174 |
| | | | contig reference | C | Thr [T] | 3 | 174 |
| 94849061 | 1087 | rs112030253 | missense | A | Arg [R] | 1 | 172 |
| | | | contig reference | G | Gly [G] | 1 | 172 |
| 94849109 | 1039 | rs78640395 | nonsense | T | xxx [X] | 1 | 156 |
| | | | contig reference | G | Glu [E] | 1 | 156 |
| 94849140 | 1008 | rs11558263 | missense | A | Arg [R] | 3 | 145 |
| | | | contig reference | C | Ser [S] | 3 | 145 |

TABLE 1-continued

Mutations in Human AAT - Entrez Gene ID: 5265

| Chr. position | mRNA position | dbSNP rs# cluster id | Function | dbSNP allele | Protein residue | Codon position | Amino acid position |
|---|---|---|---|---|---|---|---|
| 94849151 | 997 | rs20546 | synonymous | T | Leu [L] | 1 | 142 |
|  |  |  | contig reference | C | Leu [L] | 1 | 142 |
| 94849160 | 988 | rs11558261 | missense | A | Ser [S] | 1 | 139 |
|  |  |  | contig reference | G | Gly [G] | 1 | 139 |
| 94849201 | 947 | rs709932 | missense | A | His [H] | 2 | 125 |
|  |  |  | contig reference | G | Arg [R] | 2 | 125 |
| 94849228 | 920 | rs28931572 | missense | A | Asn [N] | 2 | 116 |
|  |  |  | contig reference | T | Ile [I] | 2 | 116 |
| 94849303 | 845 | rs28931568 | missense | A | Glu [E] | 2 | 91 |
|  |  |  | contig reference | G | Gly [G] | 2 | 91 |
| 94849325 | 823 | rs111850950 | missense | A | Thr [T] | 1 | 84 |
|  |  |  | contig reference | G | Ala [A] | 1 | 84 |
| 94849331 | 817 | rs113817720 | missense | A | Thr [T] | 1 | 82 |
|  |  |  | contig reference | G | Ala [A] | 1 | 82 |
| 94849345 | 803 | rs55819880 | missense | T | Phe [F] | 2 | 77 |
|  |  |  | contig reference | C | Ser [S] | 2 | 77 |
| 94849364 | 784 | rs11575873 | missense | C | Arg [R] | 1 | 71 |
|  |  |  | contig reference | A | Ser [S] | 1 | 71 |
| 94849381 | 767 | rs28931569 | missense | C | Pro [P] | 2 | 65 |
|  |  |  | contig reference | T | Leu [L] | 2 | 65 |
| 94849388 | 760 | rs28931570 | missense | T | Cys [C] | 1 | 63 |
|  |  |  | contig reference | C | Arg [R] | 1 | 63 |
| 94849466 | 682 | rs11558262 | missense | G | Ala [A] | 1 | 37 |
|  |  |  | contig reference | A | Thr [T] | 1 | 37 |
| 94849492 | 656 | rs11558259 | missense | G | Arg [R] | 2 | 28 |
|  |  |  | contig reference | A | Gln [Q] | 2 | 28 |
| 94849548 | 600 | rs11558260 | synonymous | T | Ile [I] | 3 | 9 |
|  |  |  | contig reference | C | Ile [I] | 3 | 9 |
|  |  |  | start codon |  |  |  | 1 |

Methods of Use

The invention also provides methods for expressing alpha 1-antitrypsin (AAT) protein in a subject. Typically, the subject has or suspected of having an AAT deficiency. The methods typically involve administering to a subject an effective amount of a recombinant Adeno-Associated Virus (rAAV) harboring any of the isolated nucleic acids disclosed herein. In general, the "effective amount" of a rAAV refers to an amount sufficient to elicit the desired biological response. In some embodiments, the effective amount refers to the amount of rAAV effective for transducing a cell or tissue ex vivo. In other embodiments, the effective amount refers to the amount effective for direct administration of rAAV to a subject. As will be appreciated by those of ordinary skill in this art, the effective amount of the recombinant AAV of the invention varies depending on such factors as the desired biological endpoint, the pharmacokinetics of the expression products, the condition being treated, the mode of administration, and the subject. Typically, the rAAV is administered with a pharmaceutically acceptable carrier.

The subject may have a mutation in an AAT gene. The mutation may result in decreased expression of wild-type (normal) AAT protein. The subject may be homozygous for the mutation. The subject may be heterozygous for the mutation. The mutation may be a missense mutation. The mutation may be a nonsense mutation. The mutation may be a mutation listed in Table 1. The mutation may result in expression of a mutant AAT protein. The mutant protein may be a gain-of-function mutant or a loss-of-function mutant. The mutant AAT protein may be incapable of inhibiting protease activity. The mutant AAT protein may fail to fold properly. The mutant AAT protein may result in the formation of protein aggregates. The mutant AAT protein may result in the formation of intracellular AAT globules. The mutation may result in a glutamate to lysine substitution at amino acid position 366 in the precursor protein according to the amino acid sequence set forth as SEQ ID NO: 3. In the mature protein, this same mutation occurs at amino acid position 342 (SEQ ID NO: 4). The methods may also involve determining whether the subject has a mutation. Accordingly the methods may involve obtaining a genotype of the AAT gene in the subject.

In some cases, after administration of the rAAV the level of expression of the first protein and/or second protein is determined in the subject. The administration may be performed on one or more occasions. When the administration is performed on one or more occasions, the level of the first protein and/or the level of the second protein in the subject are often determined after at least one administration. In some cases, the serum level of the first protein in the subject is reduced by at least 85% following administration of the rAAV. The serum level of the first protein in the subject may be reduced by at least 90% following administration of the rAAV. The serum level of the first protein in the subject may be reduced by at least 95% following administration of the rAAV. However, in some cases, the serum level of the first protein in the subject is reduced by at least 40%, at least 50%, at least 60%, at least 70%, or at least 80% following administration of the rAAV.

The level (e.g., serum level) of the first protein in the subject may be reduced by at least 85% within 2 weeks following administration of the rAAV. The serum level of the first protein in the subject may be reduced by at least 90% within 2 weeks following administration of the rAAV. The serum level of the first protein in the subject may be reduced by at least 85% within 4 weeks of administration of the rAAV. The reduction may be observed within 1 day, within 2 days, within 3 days, within 4 days, within 5 days, within 6 days, within 1 week, within 2 weeks, within 3 weeks, within 4 weeks or more.

The reduction in the level of the first protein may be sustained for at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, or more. In some cases, after 7 weeks of administration of the rAAV, the serum level of the first protein is at a level of at least 50% compared with the serum level of the first protein prior to administration of the rAAV. In certain cases, after 7 weeks of administration of the rAAV, the serum level of the first protein is at a level of at least 75% compared with the serum level of the first protein prior to administration of the rAAV.

In some instances, after administration of the rAAV at least one clinical outcome parameter associated with the AAT deficiency is evaluated in the subject. Typically, the clinical outcome parameter evaluated after administration of the rAAV is compared with the clinical outcome parameter determined at a time prior to administration of the rAAV to determine effectiveness of the rAAV. Often an improvement in the clinical outcome parameter after administration of the rAAV indicates effectiveness of the rAAV. Any appropriate clinical outcome parameter may be used. Typically, the clinical outcome parameter is indicative of the one or more symptoms of an AAT deficiency. For example, the clinical outcome parameter may be selected from the group consisting of: serum levels of the first protein, serum levels of the second protein, presence of intracellular AAT globules, presence of inflammatory foci, breathing capacity, cough frequency, phlegm production, frequency of chest colds or pneumonia, and tolerance for exercise. Intracellular AAT globules or inflammatory foci are evaluated in tissues affected by the AAT deficiency, including, for example, lung tissue or liver tissue.

Recombinant AAVs

In some aspects, the invention provides isolated AAVs. As used herein with respect to AAVs, the term "isolated" refers to an AAV that has been isolated from its natural environment (e.g., from a host cell, tissue, or subject) or artificially produced. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s). The AAV capsid is an important element in determining these tissue-specific targeting capabilities. Thus, a rAAV having a capsid appropriate for the tissue being targeted can be selected. In some embodiments, the rAAV comprises a capsid protein having an amino acid sequence corresponding to any one of AAV1, AAV2, AAV3, AAV4, AAV5, AAV6, AAV7, AAV8, AAV9, AAV10, AAV11 and variants thereof. The recombinant AAVs typically harbor an isolated nucleic acid of the invention.

Methods for obtaining recombinant AAVs having a desired capsid protein are well known in the art (See, for example, US 2003/0138772, the contents of which are incorporated herein by reference in their entirety). AAV capsid proteins that may be used in the rAAVs of the invention a include, for example, those disclosed in G. Gao, et al., J. Virol., 78(12):6381-6388 (June 2004); G. Gao, et al, Proc Natl Acad Sci USA, 100(10):6081-6086 (May 13, 2003); US 2003-0138772, US 2007/0036760, US 2009/0197338, and WO 2010/138263, the contents of which relating to AAVs capsid proteins and associated nucleotide and amino acid sequences are incorporated herein by reference. Typically the methods involve culturing a host cell which contains a nucleic acid sequence encoding an AAV capsid protein or fragment thereof; a functional rep gene; a recombinant AAV vector composed of AAV inverted terminal repeats (ITRs) and a transgene; and sufficient helper functions to permit packaging of the recombinant AAV vector into the AAV capsid proteins.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing the rAAV of the invention may be delivered to the packaging host cell using any appropriate genetic element (vector). The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, J. Virol., 70:520-532 (1993) and U.S. Pat. No. 5,478,745.

In some embodiments, recombinant AAVs may be produced using the triple transfection method (e.g., as described in detail in U.S. Pat. No. 6,001,650, the contents of which relating to the triple transfection method are incorporated herein by reference). Typically, the recombinant AAVs are produced by transfecting a host cell with a recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present invention include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the invention provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

In some aspects, the invention provides isolated cells. As used herein with respect to cell, the term "isolated" refers to a cell that has been isolated from its natural environment (e.g., from a tissue or subject). As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA) from a transcribed gene.

The foregoing methods for packaging recombinant vectors in desired AAV capsids to produce the rAAVs of the invention are not meant to be limiting and other suitable methods will be apparent to the skilled artisan.

Recombinant AAV Vectors

The isolated nucleic acids of the invention may be recombinant AAV vectors. The recombinant AAV vector may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise, as disclosed elsewhere herein, one or more regions that encode one or more inhibitory RNAs (e.g., miRNAs) comprising a nucleic acid that targets an endogenous mRNA of a subject. The transgene may also comprise a region encoding an exogenous mRNA that encodes a protein (e.g., a protein that has an amino acid sequence that is at least 85% identical to the protein encoded by the endogenous mRNA), in which the one or more inhibitory RNAs do not target the exogenous mRNA.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In addition to the major elements identified above for the recombinant AAV vector, the vector also includes conventional control elements which are operably linked with elements of the transgene in a manner that permits its transcription, translation and/or expression in a cell transfected with the vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., miRNA).

For nucleic acids encoding proteins, a polyadenylation sequence generally is inserted following the transgene sequences and before the 3' AAV ITR sequence. A rAAV construct useful in the present invention may also contain an intron, desirably located between the promoter/enhancer sequence and the transgene. One possible intron sequence is derived from SV-40, and is referred to as the SV-40 T intron sequence. Any intron may be from the β-Actin gene. Another vector element that may be used is an internal ribosome entry site (IRES).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer), the SV40 promoter, and the dihydrofolate reductase promoter. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system, the ecdysone insect promoter, the tetracycline-repressible system, the tetracycline-inducible system, the RU486-inducible system and the rapamycin-inducible system. Still other types of inducible promoters which may be useful in this context are those which are regulated by a specific physiological state, e.g., temperature, acute phase, a particular differentiation state of the cell, or in replicating cells only. In another embodiment, the native promoter, or fragment thereof, for the transgene will be used. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. In some embodiments, the promoter is a chicken β-actin promoter.

In some embodiments, one or more bindings sites for one or more of miRNAs are incorporated in a transgene of a rAAV vector, to inhibit the expression of the transgene in one or more tissues of a subject harboring the transgenes, e.g., non-liver tissues, non-lung tissues. The skilled artisan will appreciate that binding sites may be selected to control the expression of a transgene in a tissue specific manner. The miRNA target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or more nucleotides. The target site sequence may comprise at least 5 nucleotides of the sequence of a target gene binding site.

In some embodiments, the cloning capacity of the recombinant RNA vector may be limited and a desired coding sequence may involve the complete replacement of the virus's 4.8 kilobase genome. Large genes may, therefore, not be suitable for use in a standard recombinant AAV vector, in some cases. The skilled artisan will appreciate that options are available in the art for overcoming a limited coding capacity. For example, the AAV ITRs of two genomes can anneal to form head to tail concatamers, almost doubling the capacity of the vector. Insertion of splice sites allows for the removal of the ITRs from the transcript. Other options for overcoming a limited cloning capacity will be apparent to the skilled artisan.

Recombinant AAV Administration rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected tissue (e.g., liver tissue, lung tissue)

and administration subcutaneously, intraopancreatically, intranasally, parenterally, intravenously, intramuscularly, intrathecally, intracerebrally, orally, intraperitoneally, by inhalation or by another route. Routes of administration may be combined, if desired. Delivery of certain rAAVs to a subject may be, for example, by administration into the bloodstream of the subject. Administration into the bloodstream may be by injection into a vein, an artery, or any other vascular conduit.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, intracerebrally, orally, intraperitoneally, or by inhalation.

It can be appreciated by one skilled in the art that desirable administration of rAAV-based therapeutic constructs can also include ex vivo administration. In some embodiments, ex vivo administration comprises (1) isolation of cells or tissue(s) of interest from a subject, (2) contacting the cells or tissue(s) with rAAVs in sufficient amounts to transfect the cells or tissue to provide sufficient levels of gene transfer and expression without undue adverse effect, and (3) transferring cells or tissue back into the subject. In some embodiments, cells or tissues may be cultured ex vivo for several days before and/or after transfection.

Cells or tissues can be isolated from a subject by any suitable method. For example, cells or tissues may be isolated by surgery, biopsy (e.g., biopsy of skin tissue, lung tissue, liver tissue, adipose tissue), or collection of biological fluids such as blood. In some embodiments, cells are isolated from bone marrow. In some embodiments, cells are isolated from adipose tissue. In some embodiments, cells are isolated from a lipoaspirate. Appropriate methods for isolating cells from adipose tissue for ex vivo transfection are known in the art. See, e.g., Kuroda, M., et al., (2011), Journal of Diabetes Investigation, 2: 333-340; Kouki Morizono, et al. Human Gene Therapy. January 2003, 14(1): 59-66; and Patricia A. Zuk, Viral Transduction of Adipose-Derived Stem Cells, Methods in Molecular Biology, 1, Volume 702, Adipose-Derived Stem Cells, Part 4, Pages 345-357.

In some embodiments, the isolated cells comprise stem cells, pluripotent stem cells, lipoaspirate derived stem cells, liver cells (e.g., hepatocytes), hematopoetic stem cells, mesenchymal stem cells, stromal cells, hematopoetic cells, blood cells, fibroblasts, endothelial cells, epithelial cells, or other suitable cells. In some embodiments, cells to be transfected are induced pluripotent stem cells prepared from cells isolated from the subject.

In an embodiment, cells or tissue(s) are transduced at a multiplicity of infection (MOI) of at least 10 infectious units (i.u.) of a rAAV per cell (for example, 10, 100, 1,000, 5,000, 10,000, 100,000 or more i.u.) or at a functionally equivalent viral copy number. In one embodiment, cells or tissue(s) are transduced at a MOI of 10 to 10,000 i.u. Routes for transfer of transfected cells or tissue(s) into a subject include, but are not limited to, subcutaneously, intraopancreatically, intranasally, parenterally, intravenously, intravascularly, intramuscularly, intrathecally, intracerebrally, intraperitoneally, or by inhalation. In some embodiments, transfected cells are administered by hepatic portal vein injection. In some embodiments, transfected cells are administered intravascularly. Methods for ex vivo administration of rAAV are well known in the art (see, e.g., Naldini, L. Nature Reviews Genetics (2011) 12, 301-315, Li, H. et al. Molecular Therapy (2010) 18, 1553-1558, and Loiler et al. Gene Therapy (2003) 10, 1551-1558).

Recombinant AAV Compositions

The rAAVs may be delivered to a subject in compositions according to any appropriate methods known in the art. The rAAV, preferably suspended in a physiologically compatible carrier (e.g., in a composition), may be administered to a subject, e.g., a human, mouse, rat, cat, dog, sheep, rabbit, horse, cow, goat, pig, guinea pig, hamster, chicken, turkey, or a non-human primate (e.g., Macaque). The compositions of the invention may comprise a rAAV alone, or in combination with one or more other viruses (e.g., a second rAAV encoding having one or more different transgenes).

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. Still others will be apparent to the skilled artisan.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The dose of rAAV virions required to achieve a desired effect or "therapeutic effect," e.g., the units of dose in vector genomes/per kilogram of body weight (vg/kg), will vary based on several factors including, but not limited to: the route of rAAV administration, the level of gene or RNA expression required to achieve a therapeutic effect, the specific disease or disorder being treated, and the stability of the gene or RNA product. One of skill in the art can readily determine a rAAV virion dose range to treat a subject having a particular disease or disorder based on the aforementioned factors, as well as other factors that are well known in the art. An effective amount of the rAAV is generally in the range of from about 10 µl to about 100 ml of solution containing from about 109 to $10^{16}$ genome copies per subject. Other volumes of solution may be used. The volume used will typically depend, among other things, on the size of the subject, the dose of the rAAV, and the route of administration. For example, for intravenous administration a volume in range of 10 µl to 100 µl, 100 µl to 1 ml, 1 ml to 10 ml, or more may be used. In some cases, a dosage between about $10^{10}$ to $10^{12}$ rAAV genome copies per subject is appropriate. In some embodiments the rAAV is administered at a dose of $10^{10}$, $10^{11}$, $10^{12}$, $10^{13}$, $10^{14}$, or $10^{15}$ genome copies per subject. In some embodiments the rAAV is administered at a dose of $10^{10}$, $10^{11}$, $10^{12}$, $10^{13}$, or $10^{14}$ genome copies per kg.

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active ingredient or more, although the percentage of the active ingredient(s) may, of course, be varied and may conveniently be between about 1 or 2% and about 70% or 80% or more of the weight or volume of the total formulation. Naturally, the amount of active ingredient in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present invention into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trails examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 .ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (ie., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The isolated nucleic acids, compositions, rAAV vectors, rAAVs, etc. described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to a subject, such as a syringe, topical application devices, or IV needle tubing and bag.

Exemplary embodiments of the invention will be described in more detail by the following examples. These embodiments are exemplary of the invention, which one skilled in the art will recognize is not limited to the exemplary embodiments.

EXAMPLES

Introduction to the Examples

Alpha-1 antitrypsin (AAT) deficiency is one of the most commonly inherited diseases in North America, with a carrier frequency of approximately 4% in the US population. The most common mutation arises as a single base pair change (Glu342Lys, PI*Z, SEQ ID 4) and leads to the synthesis of the mutant Z-AAT protein, which polymerizes and accumulates within hepatocytes, precluding its efficient secretion. The subsequent relative deficiency of serum AAT predisposes to chronic lung disease. Twelve to 15% of homozygous PI*ZZ patients develop significant liver disease, ranging from neonatal hepatitis, cholestatic jaundice and cirrhosis to adult-onset cirrhosis and hepatocellular carcinoma. Liver injury is considered to be a consequence of the pathological accumulation of mutant Z-AAT protein polymers within the endoplasmic reticulum of hepatocytes.

Strategies to alleviate the liver disease are focused on decreasing the presence of the mutant Z-AAT protein in the hepatocytes by either reducing expression of the mutant protein, or augmenting its proteolysis or secretion. In vivo studies of an allele-specific small interfering RNA (siRNA) directed against PI*Z AAT in the Pi*Z transgenic mouse model of AAT deficiency have been performed. In vitro studies using U6-driven shRNA clones in recombinant adeno-associated virus (rAAV) backbones have identified an effective allele-specific siRNA sequence (termed p10) that can reduce Pi*Z AAT protein levels while minimizing knockdown of the normal Pi*M AAT. Using the AAV8 capsid, rAAV-U6-p10 was packaged and administered by hepatic portal vein injection into Pi*Z transgenic mice for direct in vivo targeting of the liver. A similarly delivered AAV8-packaged non-specific siRNA, rAAV-U6-NC, served as a control (NC). Histological data from these studies revealed areas of complete or partial elimination of Z-AAT protein in the liver at 10 days post-injection in the p10 cohort. Analysis of the serum Z-AAT levels shows a kinetically significant reduction for 4 weeks post-injection in the p10 cohort when compared to NC control cohort. To examine the allele-specificity, AAV8-packaged Pi*M-AAT was co-administered with each shRNA construct. For both the p10+Pi*M and NC+Pi*M groups, there was considerable expression of AAT in the liver by histological staining and there was no significant difference in serum AAT levels.

The Pi*Z mutation (Glu342Lys) within exon 5 of alpha-1 antitrypsin (AAT) causes a plasma AAT deficiency (A1AD) which exposes lung tissue to uncontrolled proteolytic attack and can result in emphysema. Pi*Z mutant AAT is retained within the hepatocytes and causes a liver disease in ~12% of patients with the deficiency. Delivering wild-type copies of AAT does not address the liver pathology so down-regulation strategies including siRNA have been targeted to AAT message within hepatocytes. Since mutant AAT-PiZ exhibits a gain-of-function hepatocellular toxicity accumulating in the endoplasmic reticulum, decreasing AAT-Pi*Z mRNA levels (and therefore the protein) may ameliorate or even reverse the liver pathology. In addition, increased secretion of functional AAT protein will theoretically protect the lungs from neutrophil elastase and associated proteolytic enzymes.

The strategies described herein include the development of rAAV mediated therapies to both augment serum levels of normal AAT and down-regulate mutant AAT using miRNA. To achieve expression and secretion of wild-type AAT while simultaneously reducing AAT-PiZ levels. Three miRNA sequences targeting the AAT gene were selected in some embodiments and cloned into two different locations of the expression cassette. The first location is within the intron of the CB promoter driving expression of GFP, and the second location was between the polyA sequence and the 3' end of the gene, an additional construct with miRNAs at both locations was also created. These three constructs were packaged into rAAV8 and delivered to transgenic mice expressing the mutant form of human AAT (hAAT Pi*Z) at $6 \times 10^{11}$ vector particles per mouse via the tail vein. These experiments showed about a 60% to 80% reduction in secreted AAT protein in mice serum when compared with CB-GFP control vector injected group. It was determined that the 3×D construct was the most efficient for knocking down hAAT, in some embodiments. Liver immuno-histology also showed hAAT Pi*Z protein clearance at 4 weeks after vector delivery. Using an AAT sequence with silent base pair changes to prevent the miRNA silencing allows both up regulation of wildtype AAT gene expression while simultaneously knocking down levels of mutant protein with a single rAAV vector construct.

Materials and Methods rAAV9 Packaging and Purification:

Recombinant AAV9 vectors used in this study were generated, purified, and titered by the UMass Gene Therapy Vector Core as previously described.

Cell Culture and Transfection:

HEK-293 cells were cultured in Dulbecco's modified Eagle's medium supplemented with 10% fetal bovine serum and 100 mg/l of penicillin-streptomycin (Gemini Bio-products Cat#400-109, Woodland, Calif.). Cells were maintained in a humidified incubator at 37° C. and 5% CO2. Plasmids were transiently transfected using Lipofectamine 2000 (Cat#11668-027 Invitrogen, Carlsbad, Calif.) according to the manufacturer's instructions. Cell culture supernatants or cell lyses were collected accordingly.

Serum AAT ELISAs

Human AAT ELISA:

Total AAT protein levels were detected by ELISA. High binding extra, 96-well plate (Immulon 4, cat #3855 Dynatech Laboratories, Inc., Chantilly, Va.) were coated with 100 µl of goat anti-hAAT (1:500 diluted; cat #55111MP Biomedicals, irvine CA) in Voller's buffer overnight at 4° C. After blocking with 1% non-fat dry milk in PBS-T, duplicate standard curves (hAAT; cat #16-16-011609, Athens Research and Technology, Athens, Ga.) and serially diluted unknown samples were incubated in the plate at room temperature for 1 hr, a second antibody, Goat anti-hAAT (HRP) (1:5000 diluted, cat #ab7635-5, Abcam Inc, Cambridge, Mass.) was incubated at room temperature for 1 h. The plate was washed with phosphate-buffered saline (PBS)-Tween 20 between reactions. After reaction with TMB peroxidase substrate (KPL, Inc, Gaithersburg, Md.) reactions were stopped by adding 2 N $H_2SO_4$ (cat #A300-500 Fisher, Pittsburgh, Pa.). Plates were read at 450 nm on a VersaMax microplate reader (Molecular Devices).

Z-AAT ELISA:

Human Z-AAT protein levels were detected by ELISA using coating antibody (1:100 diluted mouse-anti-human Alpha-1-Antitrypsin-Z, clone F50.4.1 Monoclonal Antibody cat #MON5038, Cell Sciences, Inc., Canton, Mass.). Standard curves were created using PIZ mouse serum with 5% BSA (cat #B4287 Sigma, St. Louis, Mo.). Serially diluted unknown samples were incubated in the plate at 37° C. for 1 hr, secondary antibody and following the step were same as the standard human-AAT ELISA described above, except secondary antibody was diluted in 5% BSA and incubated in the plate at 37° C. for 1 hr.

c-Myc ELISA:

c-Myc tag levels were quantified by a similar method as described above. Plates were coated with a c-Myc antibody (1:1000 diluted Goat anti-c-Myc, MA cat #AB 19234 Abcam, Cambridge Mass.), plates were then blocked with 5% BSA at 37° C. for 1 hr. Standard curves were generated from supernatants collected from c-Myc-AAT transfected cells.

Real-Time RT-PCR

RNA Extraction:

Flash frozen mouse liver tissue was ground up in a pestle and mortar and used to extract either small or total RNA using the mirVana miRNA RNA Isolation Kit (cat #AM 1560 Ambion, Austin, Tex.) according to the manufacturer's instructions.

microRNA qRT-PCR:

mircoRNA was primed and reverse-transcribed with TaqMan MicroRNA reverse transcription Kit (cat #4366596, Applied Biosystems Foster City, Calif.). Quantitative PCR were performed in duplicate with gene specific RT-miRNA primers and PCR Assays were designed by Applied Biosystems, using TaqMan Gene Expression Master mix (cat #436916, Applied Biosystems, Foster City, Calif.) in a StepOne Plus real-time PCR instrument (Applied Biosystems, Foster City, Calif.).

PIM and PIZ qRT-PCR:

Total RNA was primed with oligo(dT) and reverse-transcribed with SuperScript III First-Strand Synthesis kit for RT-PCR (Cat#18989-51, Invitrogen, Carlsbad, Calif.). Quantitative PCR were performed by gene-specific primer pairs. PIM and PIZ share the primers but differ in the probes. Forward primer CCAAGGCCGTGCATAAGG (SEQ ID NO: 29), Reverse primer: GGCCCCAGCAGCTTCAGT (SEQ ID NO: 30), PIZ probe: 6FAM-CTGACCATCGA-CAAGA-MGBNFQ (SEQ ID NO: 31) and PIM probe: 6FAM-CTGACCATCGACGAGA-MGBNFQ (SEQ ID NO: 32), Reactions were performed using TaqMan Gene Expression Master mix (cat #436916, Applied Biosystems, Foster City, Calif.) in a StepOne Plus real-time PCR instrument (Applied Biosystems, Foster City, Calif.).

Z-AAT Transgenic Mice and rAAV9 Delivery:

The PiZ-transgenic mice used in this study have been described previously. All animal procedures were performed according to the guidelines of the Institutional Animal Care and Use Committee of the University of Massachusetts Medical School. Recombinant AAV9 vector was administered by mouse tail veil injection. The injections were performed in the most accessible vessels veins that run the length of both lateral aspects of the tail by grasping the tail at the distal end. Bleeds were performed through the facial vein pre-injection and every week after tail vein rAAV9 delivery until termination of the studies.

Liver Histology:

For determination of histological changes, liver samples were fixed in 10% neutral-buffered formalin (Fisher Scientific), and embedded in paraffin. Sections (5 am) were stained with hematoxylin and eosin and periodic acid-Schiff (PAS) with or without diastase digestion.

Immuno-histochemistry for hAAT was performed as previously described[14], briefly tissue sections (5 am) were deparaffinized, rehydrated, and blocked for endogenous peroxidase with 3% hydrogen peroxide in methanol for 10 minutes. To detect hAAT expression, tissue sections were incubated with primary antibody, rabbit antihuman AAT (1:800; RDI/Fitzgerald Industries, Concord, Mass.), for overnight at 4° C. Staining was detected using ABC-Rb-HRP and DAB kits (Vector Laboratories, Burlingame, Calif.).

Histology Image Analysis.

Slides were stained for PASD to remove glycogen. Whole digital slide images were created using an Aperio CS ScanScope (V, CA) and analyzed using the positive pixel count algorithm (version 9). PASD-positive globules were expressed as the proportion of strong positive pixels to total pixels using a hue value of 0.9, hue width of 0.15, and color saturation threshold of 0.25. The intensity threshold for strong positivity was set to an upper limit of 100.

Analysis of Z-AAT Protein Monomer and Polymer.

For soluble/insoluble protein separation, 10 mg of whole liver was added to 2 ml buffer at 4° C. (50 mmol/l Tris-HCl (pH 8.0), 150 mmol/l NaCl, 5 mmol/l KCl, 5 mmol/l MgCl2, 0.5% Triton X-100, and 80 µl of complete protease inhibitor stock). The tissue was homogenized in a prechilled Dounce homogenizer for 30 repetitions, then vortexed vigorously. A 1-ml aliquot was passed through a 28-gauge needle 10 times. The total protein concentration of the sample was determined, and a 5-jag total liver protein sample was aliquoted and centrifuged at 10,000 g for 30 minutes at 4° C. Supernatant (soluble (S) fraction) was immediately removed into fresh tubes; extreme care was taken to avoid disturbing the pellet (insoluble (I) fraction). The insoluble polymers pellet (I fraction) was denatured and solubilized via addition of 10 l chilled cell lysis buffer (1% Triton X-100, 0.05% deoxycholate, 10 mmol/l EDTA in phosphate-buffered saline), vortexed for 30 seconds, sonicated on ice for 10 minutes and vortexed. To each soluble and insoluble sample, 2.5 sample buffer (50% 5 sample buffer (5% sodium dodecyl sulfate, 50% glycerol, 0.5 mol/l Tris (pH 6.8)), 10% mercaptoethanol, 40% ddH2O) was added at a volume of 50% of the sample volume. Samples were boiled and loaded for sodium dodecyl sulfate-polyacrylamide gel electrophoresis (SDS-PAGE); equal amounts of total liver protein were loaded per soluble-insoluble pair in quantitative experiments. Densitometry was performed using Image J Software (NIH, Bethesda, Md.).

Serum Chemistries:

Serum samples were analyzed by UMass Mouse Phenotyping Center Analytical Core, using the NExCT Clinical Chemistry Analyzer (Alfa Wassermann Diagnostic Technologies, West Caldwell, N.J.). Serum was analyzed for alanine aminotransferase (ALT) and aspartate aminotransferase (AST) according the manufacturers specifications.

miRNA Microarray Expression Analysis:

8 µg of total RNA were isolated from flash frozen mouse livers using the mirVana miRNA isolation kit (Ambion). The experimental design included six groups with RNA samples from 5 mice each which were assayed on single color arrays for a total of 30 independent microarrays. In brief, the RNA was labeled with Cy5 and hybridized to dual-channel microarray tParaFlo microfluidics chips (LC Sciences) containing miRNA probes to mouse mature miRNAs available in the Sanger miRBase database (Release 16.0) as previously described[15]. Each of the spotted detection probes consisted of a nucleotide sequence complementary to a specific miRNA sequence and a long non-nucleotide spacer that extended the specific sequence away from the chip surface. Fluorescence images were collected using a laser scanner (GenePix 4000B, Molecular Device) and digitized using Array-Pro image analysis software (Media Cybernetics). The data was analyzed including background subtraction, using a LOWESS (locally weighted regression) method on the background-subtracted data as previously described[16]. The normalization is to remove system related variations, such as sample amount variations, and signal gain differences of scanners. Detection was determined to be positive only if transcripts had a signal intensity higher than 3× (background SD) and spot CV<0.5. CV as calculated by (SD)/(signal intensity), and in which repeating probes on the array produced signals from at least 50% of the repeating probes above detection level. Data is represented as a Log 2 transformation. The data was further filtered to remove miRNAs with (normalized) intensity values below a threshold value of 32 across all samples. t-Test were performed between "control" and "test" sample groups where T-values are calculated for each miRNA, and p-values are computed from the theoretical t-distribution. If p<0.05, it is plotted as red spot in a log scatter plot.

Figure 1A:
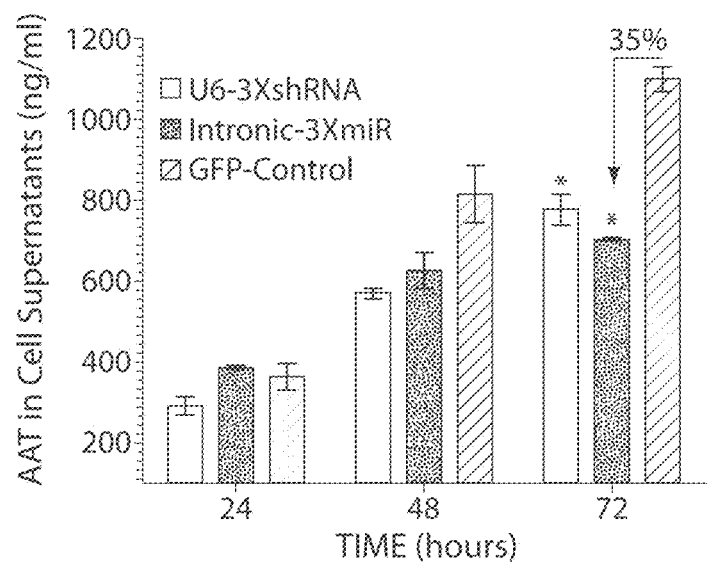
FIGS. 1A-1B Comparison of shRNA and miRNA mediated knockdown of human AAT. HEK-293 cells were contrasfected with human Z-AAT plasmid and either a plasmid expressing 3 anti-AAT shRNAs from a U6 promoter or a plasmid expressing 3 anti-AAT miRNA from a hybrid chicken beta actin promoter.
Figure 1B:
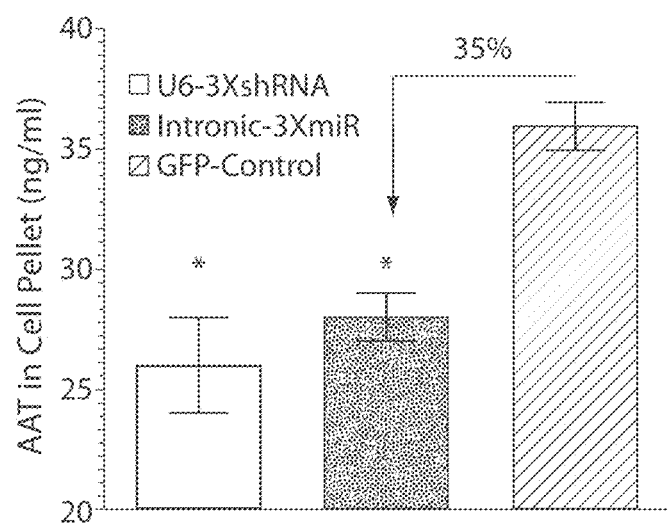

Artificial miRNAs are as Efficient as shRNAs at Downregulating Alpha-1 Antitrypsin In Vitro Efficient Z-AAT knockdown has been demonstrated in vivo and in vitro using shRNAs expressed from a pol III U6 promoter using rAAV8. In order to determine if an alternative and potentially safer approach could be employed using polymerase II driven miRNA expression, three distinct miRNAs targeting the human AAT gene were cloned into the intron of a hybrid chicken beta-actin (CB) promoter driving GFP expression (Table 2 and FIG. 1). An in vitro comparison of the previously used U6 driven shRNAs against the pol II driven miRNAs was carried out on cell lines expressing the human Pi*Z AAT gene. Initially a delay in Z-AAT knockdown with the miRNAs at 24 hrs was observed, but an eventual comparable ~35% reduction in secreted AAT protein by 48 and 72 hrs was observed for both constructs as compared to GFP controls (FIG. 1a). A similar reduction was observed in intracellular AAT protein levels assayed from the cell pellets at 72 hrs (FIG. 1b).

rAAV9 Expressed miRNAs Mediate Efficient AAT Knockdown In Vivo

Figure 2:
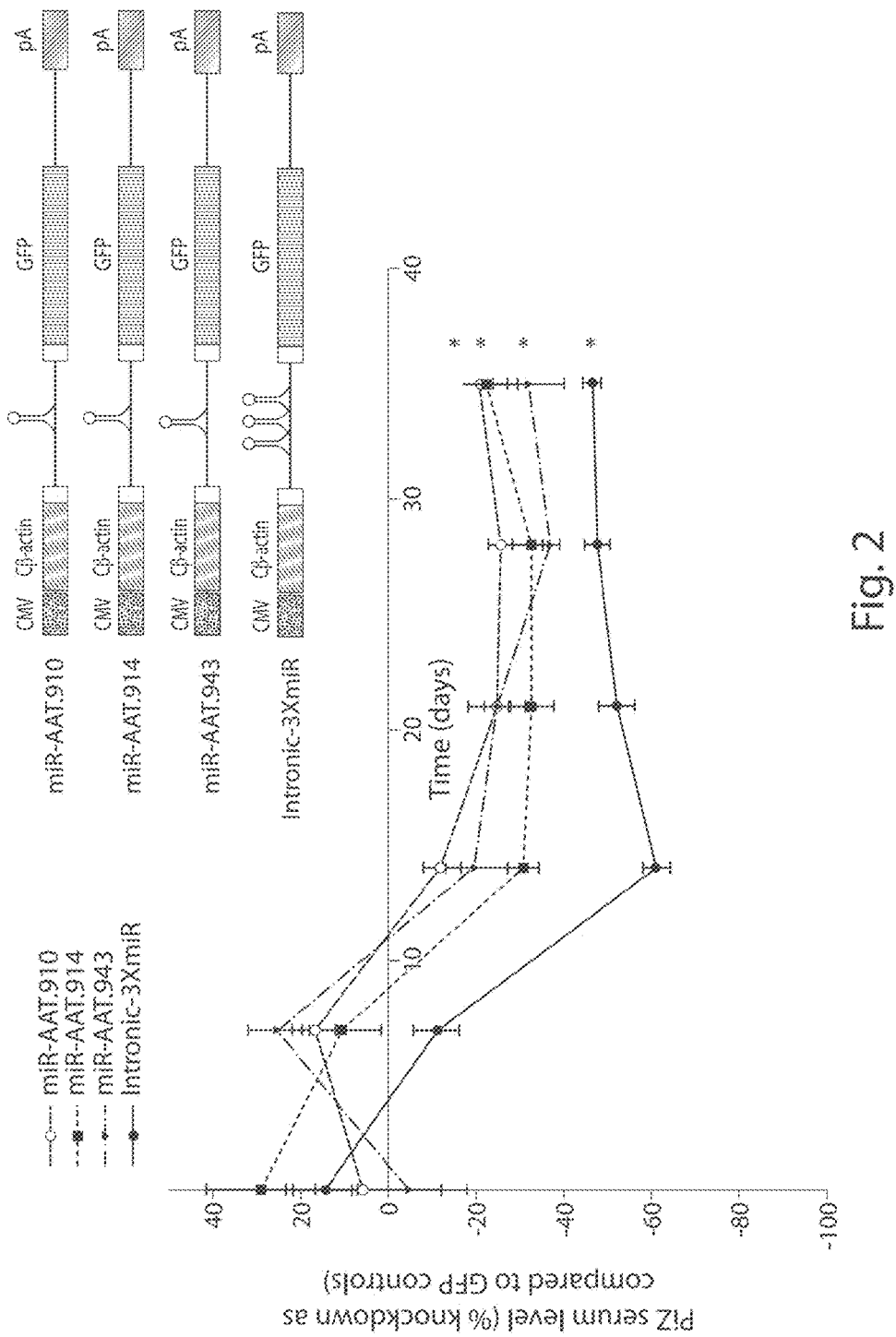
FIG. 2 In vivo silencing of human AAT by rAAV9 expressed miRNAs. Transgenic mice expressing the human PiZ allele were injected with $5\times10^{11}$ vector particles or rAAV9 expressing miRNAs against AAT under the control of the hybrid chicken beta-actin promoter via the tail vein. Serums from each cohort were collected on a weekly basis and were used to assess Z-AAT concentration by ELISA. Data is expressed as group means+SEM (n=6).
Figure 3A:
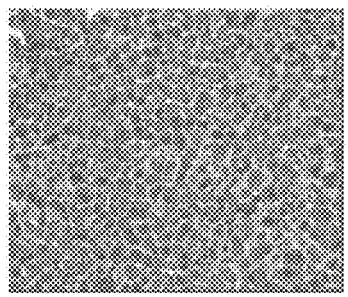
FIGS. 3A-3G Liver histology for PiZ transgenic mice 5 weeks post-rAAV9 delivery. Livers from mice receiving rAAV9 vectors with miRNAs and GFP controls were formalin-fixed and stained for AAT, or with a PAS-D assay. Mouse liver sections stained using an anti-human AAT antibody from a mouse treated with (FIG. 3A) intronic-3× miR or (FIG. 3B) GFP controls. Mouse Liver sections stained with diastase-resistant Periodic Acid Schiff assay from (FIGS. 3E and 3F) intronic-3×miR or (FIGS. 3C and 3D) GFP controls.
Figure 3B:
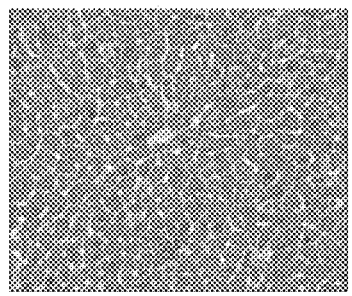
Figure 3C:
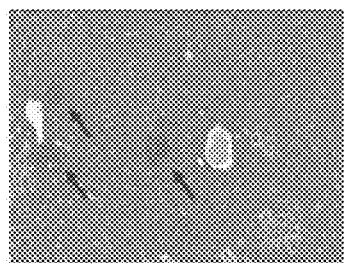
Figure 3D:
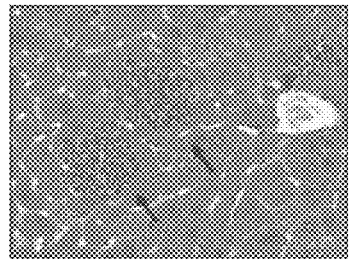
Figure 3E:
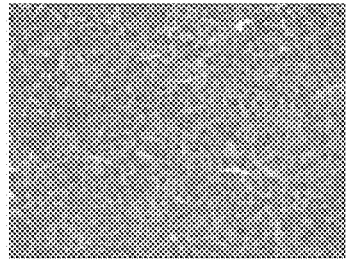
Figure 3F:
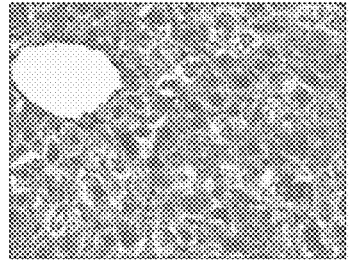
Figure 3G:
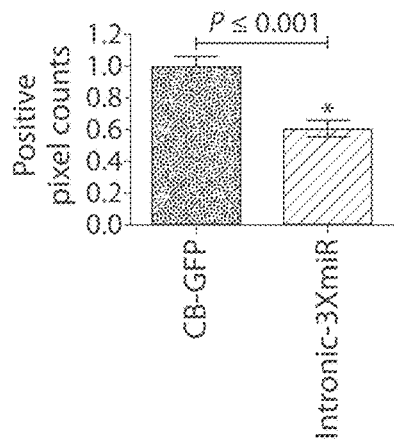

Based on the in vitro findings, the construct with the three intronic miRNA sequences (intronic 3×miR) along with three other constructs containing the individual miRNAs directed against the Z-AAT were packaged in rAAV and tested in vivo in the PiZ transgenic mice. Five groups of 5 week old mice received: rAAV9-CB-GFP, rAAV9-CBintronic3×miR-GFP or vector with either one of the individual miRNA via a tail vein injection with 5.0×1011 vector particles (vps) of rAAV9. Mice were bled weekly for a total of 5 weeks to check for circulating Z-AAT levels and were sacrificed on day 35 post rAAV delivery. As shown in FIG. 2, mice receiving 3× intronic miRNAs (intronic 3Xmir) had on average a sustained 50-60% decrease in serum AAT levels when compared to baseline values while mice receiving the single intronic miRNAs had on average a knockdown of 30% as compared to mice receiving the GFP control vector.

To evaluate the effect that miRNA mediated knockdown was having at the organ level, the livers of these mice were evaluated 5 weeks post rAAV delivery for abundance of intracellular Z-AAT. As can be appreciated from liver immuno-stains for human AAT in FIG. 3, there was a marked decrease in AAT positive staining in the livers belonging to mice in the rAAV9-intronic3×miR-GFP treated group. In addition to the drastic reduction in AAT positive staining, likewise there was a dramatic decrease in intracellular AAT globules as determined by diastase resistant PAS (PASD) positive staining. Importantly the reduction in both PASD and hAAT staining was accompanied by a reduction in inflammatory foci in the GFP group (FIG. 3). This suggests that the reduction in hAAT accumulation in the PiZ mice livers may be alleviating inflammation as evidenced by the reduction in inflammatory infiltrates.

Figure 4:
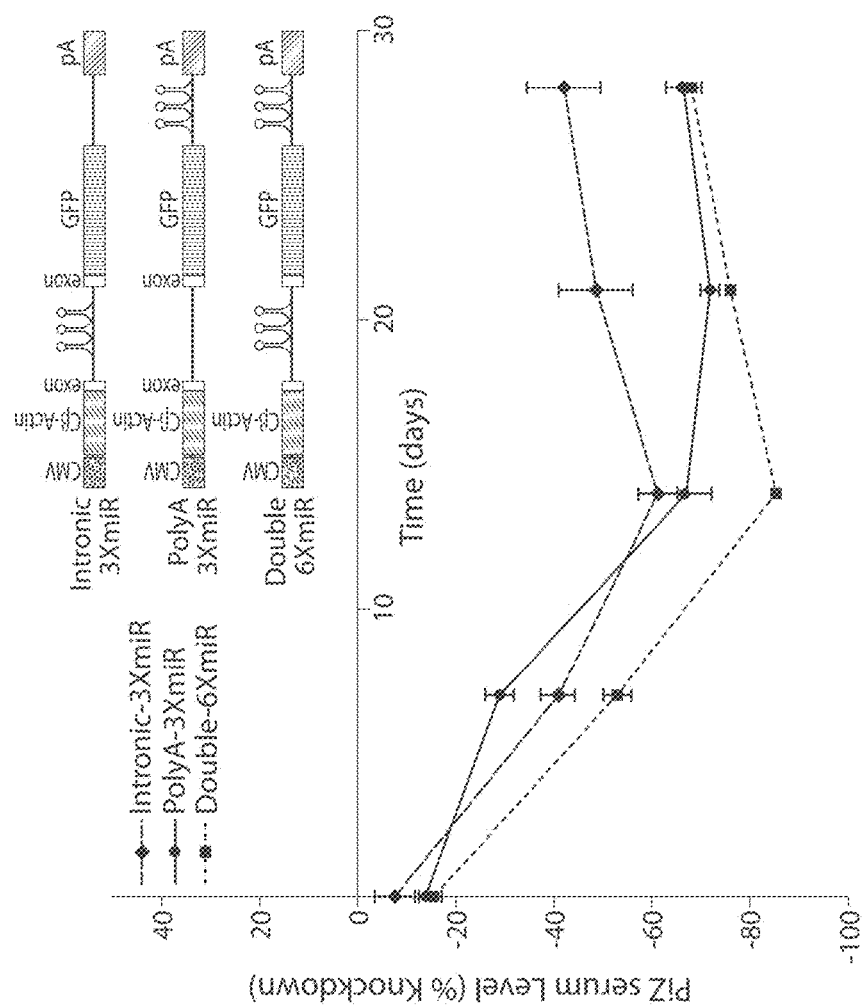
FIG. 4 In vivo optimization of anti-AAT miRNA delivery within rAAV9 vectors. Transgenic mice expressing the human PiZ allele were injected with $5\times10^{11}$ vector particles or rAAV9 expressing miRNAs against AAT under the control of the hybrid chicken beta-actin promoter via the tail vein. Serums from each cohort were collected on a weekly basis and were used to assess Z-AAT concentration by ELISA.
Figure 5:
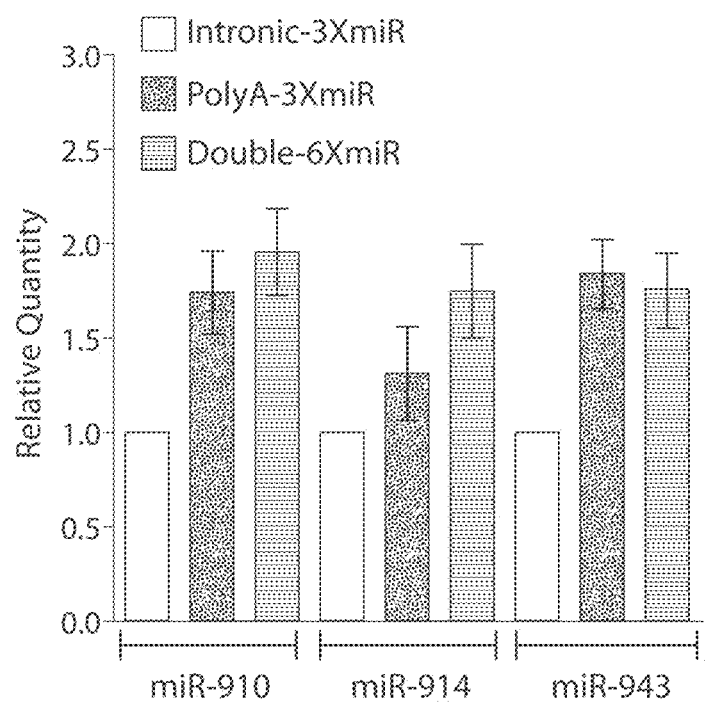
FIG. 5 Quantitative RT-PCR for artificial miRNA in vivo. Total RNA from mouse livers was used to assay for the presence of the 3 artificial anti-AAT miRNAs from mice receiving rAAV9-miRNA vectors. *<0.05 as determined by a two-way unpaired student t-test.

Onset and Degree of Knockdown are Dependent on miRNA Location within the Expression Cassette While delivering 3 miRNAs within the intron of the CB promoter was successful at lowering Z-AAT expression, it was unclear whether the location of the miRNAs within the expression cassette had any effect on their efficiency. It was investigated whether cloning the 3 miRNAs between the 3' end of the GFP gene and the polyA tail would have an effect on the kinetics of AAT knockdown. Likewise it was evaluated whether cloning the 3 miRNAs at both locations would increase (e.g., double) the amount of miRNAs being produced and lead to a further enhancement of AAT knockdown. As in the previous experiments, Z-AAT transgenic mice received $5 \times 10^{11}$ vector particles of rAAV9 vectors expressing the miRNAs either from the intron (intronic-3×miR), polyA region (PolyA-3×miR) or at both locations at once (Double-6×miR) (see diagram in FIG. 4). Analysis of serum Z-AAT levels revealed that by four weeks the PolyA-3×miR and Double-6×miR were more effective than the intronic-3×miR vector at clearing serum Z-AAT levels by 85-70% and in some cases by up to 95% with the Double-6×miR vector (FIG. 4). Real-time quantitative RT-PCR analysis of liver tissue from these mice was performed to assay for the abundance of each of the three artificial vector derived miRs (910, 914, 943). As indicated in FIG. 5, both the PolyA-3×miR and Double-6×miR vectors produced about two-fold more copies of each of the miRs (FIG. 5).

Figure 6A:
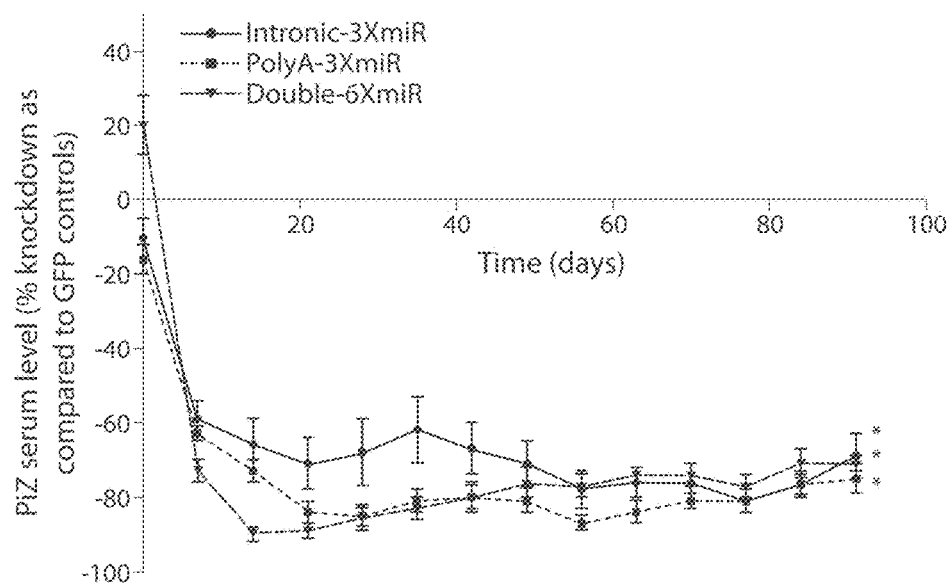
FIGS. 6A-6F Long-term In vivo silencing of human AAT by rAAV9 expressed miRNAs. Transgenic mice expressing the human PiZ allele were injected with 1×1012 vector particles or rAAV9 expressing miRNAs against AAT under the control of the hybrid chicken beta-actin promoter via the tail vein.
Figure 6B:
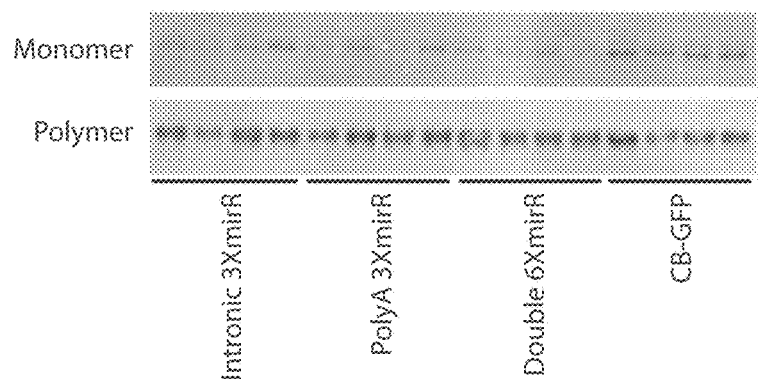
Figure 6C:
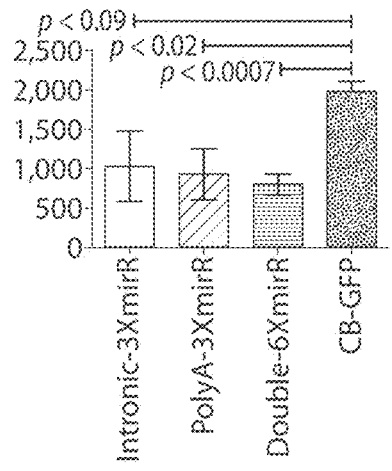
Figure 6D:
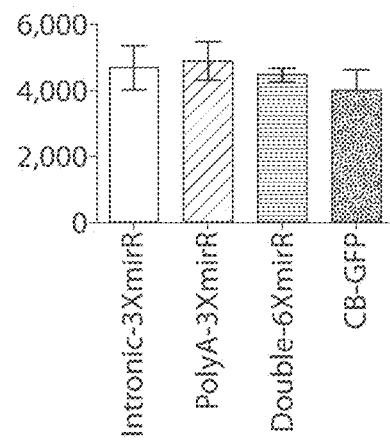
Figure 6E:
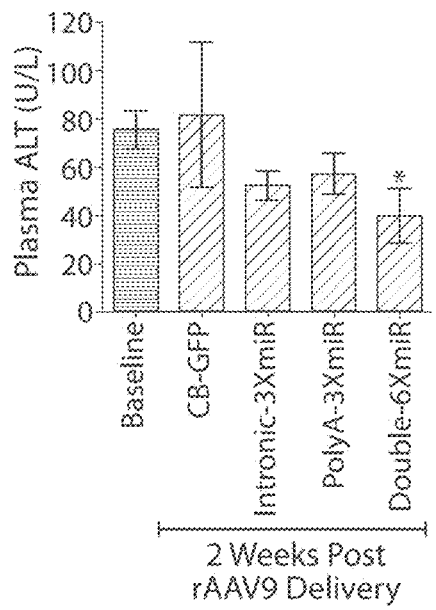
Figure 6F:
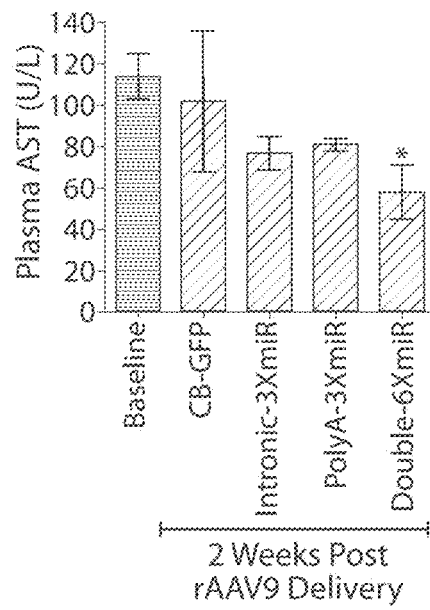

Having achieved a short-term clinically significant knockdown of more than 50% of Z-AAT protein levels it was necessary to determine if this knockdown could be sustained for longer periods of time. Once again the three vector constructs were delivered via the tail vein at a slightly higher titer of $1.0 \times 10^{12}$ vector particles per mouse and serum Z-AAT levels were monitored weekly for 3 months. The knockdown onset of the three vector varied within 7 weeks, the Double-6×miR vector achieved 90% knockdown 2 weeks after delivery, the PolyA-3×miR reached this mark by the third week while the intronic-3×miR vector remained in the range of 50-65% knockdown for the first 7 weeks (FIG. 6a). Further analysis of liver homogenates to determine whether this reduction was in the monomer or polymer pools of Z-AAT was performed on all groups. Monomer and polymer Z-AAT fractions were separated under nondenaturing conditions after which, the fractions were denatured and quantitatively assessed by immunoblotting. A reduction was observed in all groups in the monomer pool 3 months after miRNA treatment. Densitometric analysis of the bands showed significant differences in the PolyA-3×miR and Double-6×miR as compared to mice treated with a control vector (FIGS. 6B-6D). This knockdown observed at two weeks in FIG. 6a was accompanied by significant reduction in serum ALT and AST in the Double-6×miR group with clear decreasing trends in the two other groups expressing anti-AAT miRs (FIGS. 6E and 6F). Although Z-AAT levels rose slightly for animals in the Double-6×miR and PolyA-3×miR groups between week 7 and 13, all three vectors stabilized at a sustained level of about 75% knockdown of Z-AAT for the remainder of the study (FIG. 6).

In Vitro Delivery of miRNAs Against Z-AAT and Gene Correction with M-AAT Using a Single Vector A dual-function vector that would simultaneously augment protein levels of the wild-type M-AAT protein, thereby addressing both liver disease caused by the toxic gain-of-function of Z-AAT polymers and the loss-of-function caused by the absence of circulating M-AAT, was evaluated. To achieve this, the GFP gene was replaced with a wild-type AAT gene that had silent base pair changes at the miRNAs' target sites, thus making it impervious to the miRNA mediated knockdown. HEK-293 cells were co-transfected with two plasmids, one of the plasmid expressed Z-AAT and the other one was either the Double-6×miR-GFP, Double-6×miR-AAT (containing the hardened, knockdown-impervious AAT gene) or a control. The transfected cells were incubated for 72 hrs and RNA was harvested from cell pellets for a quantitative RT-PCR analysis of Z-AAT and M-AAT transcripts. Analysis of Z-AAT mRNA levels revealed the both Double-6×miR-GFP and Double-6×miR-AAT produced a significant knockdown of up to 37-fold in Z-AAT mRNA copies as compared to the mock transfected cells (FIG. 7a). Furthermore, quantitative RT-PCR for wild-type M-AAT transcripts from the same RNA pool, revealed that the Double-6×miR-AAT construct upregulated M-AAT expression by more than 100-fold over the endogenous levels observed in control transfected cells (FIG. 7b).

In Vivo Delivery of Dual-Function Vectors

Taking the in vitro findings into consideration as well as the more rapid onset and the decreased variability in knockdown observed with the Double-6×miR and PolyA-3×miR vectors (FIG. 6), both of these miRNA configurations were tested as dual function vectors in vivo. Three cohorts of seven mice each were dosed with $1.0 \times 10^{12}$ vector particles with either a GFP control, Double-6×miR-CB-AAT or a PolyA-3×miR-CB-AAT rAAV9 vectors. Serum was harvested weekly from the mice for 13 weeks and was analyzed for Z-AAT serum levels with a PiZ specific ELISA and for M-AAT levels with an ELISA detecting the cMYC tag on the M-AAT cDNA. Changes in Z-AAT serum levels were comparable to previous experiments, with a sustained knockdown around 75-85% for both vectors (FIG. 8a bottom panel). A more rapid onset of knockdown was seen with the Double-6×miR vector but the PolyA-3×miR vector achieved similar knockdown by the fourth week. As the Z-AAT knockdown progressed, a concomitant rise in circulating M-AAT was observed from mice receiving the dual function vectors (FIG. 8a upper panel).

Surprisingly, while the knockdown for both vectors was similar four weeks post delivery, the production of M-AAT was substantially different. The PolyA-3×miR-CB-AAT vector produced 8-10 times more M-AAT than the Double-6×miR-CB-AAT vector. Liver RNA was extracted from these mice at the end of the study to quantify the mRNA levels of Z-AAT and M-AAT. A precipitous decrease in Z-AAT mRNA occurred in both cohorts of mice receiving vectors with miRNAs as compared to mice receiving a rAAV9-CB-GFP control (FIG. 8B). A quantitative RT-PCR for M-AAT was also performed, to verify production of M-AAT at the RNA level and to determine if the difference in M-AAT production between dual-function vectors was related to mRNA transcription. Despite the clear difference in M-AAT serum protein levels, there was no statistically significant difference in the M-AAT mRNA levels between the two groups (FIG. 8C). This indicates that mRNA processing and translation but not the level of transcription may be affected in the Double-6×miR-CB-AAT group, in some cases.

Analysis of Global Liver miRNA Profiles after Delivery of Artificial miRNAs with rAAV9

A microarray analysis of endogenous mouse miRNAs from liver tissue for 6 groups of mice with 5 mice per group was performed on 30 separate microfluidic chips using samples obtained from the long-term Z-AAT knockdown experiments (FIG. 6), along with 5 untreated Z-AAT transgenic mice and 5 C57/BL6 mice. In order to determine basal differences imparted by the human Z-AAT gene in mice, an initial comparison between untreated PiZ mice and wiltype C57BL6 mice was performed. As shown in FIG. 9a and Table 3, there were only 4 statistically significant differences among these mice with only miR-1 having a log 2 ratio greater than 2, being upregulated in PiZ mice. The effects of rAAV9-CB-GFP, rAAV9-Double-6×miR-CB-GFP, rAAV9-PolyA-3×miR-CB-GFP and rAAV9-intronic-3×miR-CB-GFP liver transduction on liver miRNA profiles were compared. Surprisingly the expression of the artificial vector derived miRNAs had minimal impact on global miRNA profiles (see FIGS. 9B-9D). Statistically significant differences between untreated PiZ mice and rAAV9 treated mice were observed in 2-6 differentially expressed miRNAs. Of these differentially expressed miRNAs the one with the largest change was miR-1 which was down-regulated back down to levels observed in the C57Bl6. This correction of miR-1 up-regulation in PiZ mice was observed in all groups including the mice receiving only rAAV9-GFP. Thus it seems to be dependent on rAAV9 delivery and not on artificial miRNA delivery.

The results presented in these examples describe a combinatorial therapeutic approach for the treatment of both liver and lung disease present in alpha-1 antitrypsin deficiency. This therapeutic approach is based on a single dual function AAV vector to deliver both miRNAs targeting AAT for clearance of mutant mRNA along with a miRNA resistant AAT cDNA for augmentation of wild-type protein. The data presented herein support this approach as the biological activities of the miRNAs are demonstrated both by cell culture experiments, and in vivo after numerous experiments with tail vein delivery of rAAV9-pseudotyped vectors. Depending on the configuration of the miRNAs, a long-term knockdown of circulating serum Z-AAT in a range of 50-95% was consistently achieved. Furthermore, in the case of dual function vectors this knockdown was accompanied by equally sustained expression and secretion of wild-type M-AAT.

Knockdown of mutant Z-AAT protein is observed in PiZ transgenic mice using a rAAV8 vector expressing U6 driven shRNAs. Initial cell culture experiments determined that by 72 hours the efficiency of the miRNAs used in this study were comparable to shRNAs (FIG. 1). The in vivo experiments described herein corroborated this finding, as a significant decrease in Z-AAT was observed with administration of the rAAV9-CBintronic3×miR-GFP rAAV9 vector (FIG. 2). These experiments also highlighted an enhanced effect that was obtained by using 3 anti-AAT miRNAs with different target sequences as none of the vectors with a single miRNA achieved the level of knockdown seen when they were delivered in combination (FIG. 2). Another biological effect aside from Z-AAT serum reduction that was observed included a significant and widespread decrease in the accumulation of Z-AAT within the hepatocytes and a reduction of the inflammatory lymphocyte foci within the liver (FIG. 3).

Surprisingly, anti-AAT miRNA efficacy was improved by altering the location of the miRNA within the expression cassette. Initial short-term experiments demonstrated that expressing the miRNAs from the 3' end of the GFP gene rather than from the intron of the CB promoter lead to a 25% increase in the silencing capabilities of the miRNAs and also a to significant decrease in the variability of this effect. Furthermore, doubling the effective miRNA dose per vector by having the miRNAs expressed from both locations did lead to more rapid onset of Z-AAT knockdown (FIG. 4). Moreover, increased miRNA production was seen for both the PolyA-3×miR-CB-GFP and the Double-6×miR-CB-GFP vectors as compared to the rAAV9-intronic3×miR-GFP vector. This indicates that, in some embodiments, miRNA processing from the intron of the CB promoter may be not as efficient as from the 3' end of the GFP gene. In other embodiments, long-term experiments showed that initial kinetic differences in knockdown from the three vectors wanes overtime and by eight weeks the intronic3×miR-GFP decreases in variability and augments in silencing efficacy.

The potency and stability of the decrease in serum Z-AAT observed in vivo suggests that either of these vectors would lower Z-AAT levels in Pi*ZZ patients to therapeutic levels, even below those seen in Pi*MZ heterozygote patients. However, in some cases, maximal clinical benefit would be derived from a concomitant rise in M-AAT circulation. In this regard, the dual function vectors were designed to also deliver a miRNA-resistant M-AAT cDNA. Cell culture experiments showed the feasibility of this strategy as was shown by a decrease in Z-AAT specific mRNA with a simultaneous rise in M-AAT using a single pro-viral plasmid (FIG. 7). These experiments supported an in vivo study of the dual function vectors. The results from those experiments confirmed the in vitro data, clearly demonstrating the feasibility of concomitant knockdown and augmentation of mutant and wild-type protein respectively. These experiments also revealed that the double configuration of miRNAs had a more rapid onset of Z-AAT knockdown but the overall efficacy over time was comparable to the PolyA-3× miR-CB-AAT vector. In addition to improved knockdown kinetics of the Double-6×miR-CB-AAT vector, a decreased output of M-AAT was also observed (FIG. 8a). Initially it was hypothesized that this may have been a result of decreased M-AAT mRNA production due to the presence of miRNA within the intron of this construct, but as shown in FIG. 8c, there was a statistically significant difference in M-AAT mRNA was not observed between the two groups. While mRNA transcription and stability are not affected by the presence of miRNAs within the intron, their translation into protein may be hindered as observed in the decrease circulating M-AAT levels in the serum of these mice.

A consideration for a clinical therapy is an effect of artificial miRNA expression on the endogenous miRNA profiles of the target organ. In order to determine if rAAV9 expressed anti-AAT miRNAs were disturbing the endogenous miRNA profiles of the liver, the livers of 30 mice were interrogated at the end of the study described in FIG. 6 with a miRNA microarray. As can be observed from FIG. 9, neither did the delivery of rAAV9-GFP or of the vectors expressing miRNAs have a significant impact on miRNA profiles. Notably, mir-122 which is the most abundant miRNA produced in the liver was unaffected in any group. While some miRNAs were found to be expressed at statistically different levels among the groups, they were mostly on the border of having a 2-fold change with one exception. Interestingly, mir-1 seemed to consistently have upwards of a 2-fold change with rAAV9 intervention. In the case of this miRNA the fold change with rAAV intervention was in the direction of reverting the levels back to those found in wildtype C57BL6 mice (FIG. 9a). Thus, in summary, miRNA profiles were unperturbed and in some cases 'corrected' back to wildtype levels with rAAV9 delivery.

These findings indicate that other diseases states requiring the combination of augmentation of a functional allele and suppression of a mutant allele may be addressed in a similar fashion. One such example is Huntington Disease (HD), in which mutant alleles cause a severe autosomal dominant disease, but in which an allele-specific knockdown might only be feasible if the functional allele were modified to convey resistance to a miRNA-based knockdown. It is also significant that these manipulations result in minimal perturbations of endogenous miRNA profiles. This is potentially important for considering the safety of single agent miRNA-based approaches, which would be useful in other anti-viral therapies, e.g., therapies directed against HBV or HCV. As with the genetic diseases considered above, these are conditions in which the down-regulation of target genes for prolonged periods of time may be advantageous. Therefore, emergence of the rAAV-based miRNA platform as a means to address these problems would be useful as well.

TABLE 2

Artificial miRNA sequences miRNA910 (SEQ ID NO: 21)
5'-TAAGCTGGCAGACCTTCTGTCGTTTTGGCCACTGAGTGACGACAGA
AGCTGCCAGCTTA miRNA914 (SEQ ID NO: 22)
5'-AATGTAAGCTGGCAGACCTTCGTTTTGGCCACTGACTGACGAAGGT
CTCAGCTTACATT miRNA943 (SEQ ID NO: 23)
5'-ATAGGTTCCAGTAATGGACAGGTTTGGCCACTGACTGACCTGTCCA
TCTGGAACCTAT

TABLE 3

Statistically significant changes in liver miRNA profiles

| Reporter Name | p-value | Group 1 Mean Intensity (n = 5) | Group 2 Mean Intensity (n = 5) | Log2 (G2/G1) |
|---|---|---|---|---|
| | | B6-Control | PiZ-Control | |
| mmu-miR-762 | 2.39E−02 | 525 | 1,099 | 1.07 |
| mmu-miR-23a | 4.03E−02 | 1,247 | 1,591 | 0.35 |
| mmu-miR-1 | 4.95E−02 | 126 | 2,776 | 4.46 |
| mmu-miR-341* | 4.97E−02 | 4,340 | 2,287 | −0.92 |
| | | PiZ-GFP | PiZ-Control | |
| mmu-miR-1 | 6.03E−03 | 5 | 2,776 | 9.13 |
| mmu-miR-148a | 7.48E−03 | 1,841 | 1,058 | −0.80 |
| mmu-miR-720 | 9.33E−03 | 1,264 | 3,440 | 1.44 |
| mmu-miR-30c | 1.03E−02 | 2,830 | 1,757 | −0.69 |
| mmu-miR-146a | 1.71E−02 | 362 | 175 | −1.05 |
| mmu-miR-30d | 4.64E−02 | 627 | 454 | −0.47 |
| | | PiZ-PolyA | PiZ-Control | |
| mmu-miR-2145 | 1.40E−02 | 573 | 114 | −2.32 |
| mmu-miR-1 | 2.82E−02 | 22 | 2,776 | 6.95 |

TABLE 3-continued

Statistically significant changes in liver miRNA profiles

| Reporter Name | p-value | Group 1 Mean Intensity (n = 5) | Group 2 Mean Intensity (n = 5) | Log2 (G2/G1) |
|---|---|---|---|---|
| mmu-miR-690 | 2.41E−02 | 3,071 | 534 | −2.52 |
| mmu-miR-720 | 4.31E−02 | 1,816 | 3,440 | 0.92 |
| | | PiZ-6X | PiZ-Control | |
| mmu-miR-146a | 1.53E−02 | 445 | 175 | −1.35 |
| mmu-miR-1 | 3.04E−02 | 115 | 2,776 | 4.59 |

REFERENCES

1. Propst, T. et al. Prevalence of hepatocellular carcinoma in alpha-1-antitrypsin deficiency. J Hepatol 21, 1006-11 (1994).
2. Sivasothy, P., Dafforn, T. R., Gettins, P. G. & Lomas, D. A. Pathogenic alpha 1-antitrypsin polymers are formed by reactive loop-beta-sheet A linkage. J Biol Chem 275, 33663-8 (2000).
3. Lomas, D. A., Evans, D. L., Finch, J. T. & Carrell, R. W. The mechanism of Z alpha 1-antitrypsin accumulation in the liver [see comments]. Nature 357, 605-7 (1992).
4. Brantly, M. L. et al. Phase I trial of intramuscular injection of a recombinant adeno-associated virus serotype 2 alpha1-antitrypsin (AAT) vector in AAT-deficient adults. Hum Gene Ther 17, 1177-86 (2006).
5. Flotte, T. R. et al. Phase I trial of intramuscular injection of a recombinant adeno-associated virus alpha 1-antitrypsin (rAAV2-CB-hAAT) gene vector to AAT-deficient adults. Hum Gene Ther 15, 93-128 (2004).
6. Zern, M. A. et al. A novel SV40-based vector successfully transduces and expresses an alpha 1-antitrypsin ribozyme in a human hepatoma-derived cell line. Gene Ther 6, 114-20 (1999).
7. Fire, A. et al. Potent and specific genetic interference by double-stranded RNA in Caenorhabditis elegans. Nature 391, 806-11 (1998).
8. Cruz, P. E. et al. In vivo post-transcriptional gene silencing of alpha-1 antitrypsin by adeno-associated virus vectors expressing siRNA. Lab Invest 87, 893-902 (2007).
9. Grimm, D. et al. Fatality in mice due to oversaturation of cellular microRNA/short hairpin RNA pathways. Nature 441, 537-41 (2006).
10. McBride, J. L. et al. Artificial miRNAs mitigate shRNA-mediated toxicity in the brain: implications for the therapeutic development of RNAi. Proc Natl Acad Sci USA 105, 5868-73 (2008).
11. Denli, A. M., Tops, B. B., Plasterk, R. H., Ketting, R. F. & Hannon, G. J. Processing of primary microRNAs by the Microprocessor complex. Nature 432, 231-5 (2004).
12. Vaucheret, H., Vazquez, F., Crete, P. & Bartel, D. P. The action of ARGONAUTE 1 in the miRNA pathway and its regulation by the miRNA pathway are crucial for plant development. Genes Dev 18, 1187-97 (2004).
13. Gao, G. P. et al. Novel adeno-associated viruses from rhesus monkeys as vectors for human gene therapy. Proc Natl Acad Sci USA 99, 11854-9 (2002).
14. Li, H. et al. Ex vivo transduction and transplantation of bone marrow cells for liver gene delivery of alpha1-antitrypsin. Mol Ther 18, 1553-8 (2010).
15. Gao, X., Gulari, E. & Zhou, X. In situ synthesis of oligonucleotide microarrays. Biopolymers 73, 579-96 (2004).

16. Bolstad, B. M., Irizarry, R. A., Astrand, M. & Speed, T. P. A comparison of normalization methods for high density oligonucleotide array data based on variance and bias. Bioinformatics 19, 185-93 (2003).
17. Naldini, L. Ex vivo gene transfer and correction for cell-based therapies. Nature Reviews Genetics 12, 301-315 (2011).
18. Loiler, S. A., Conlon, T. J., Song, S., Tang, Q., Warrington, K. H., Agarwai, A., Kapturczak, M., Li, C., Ricordi, C., Atkinson, M. A., Muzyczka, N., and Flotte, T. R. Targeting recombinant adeno-associated virus vectors to enhance gene transfer to pancreatic islets and liverGene Therapy (2003) 10, 1551-1558).

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

As used herein, the terms "approximately" or "about" in reference to a number are generally taken to include numbers that fall within a range of 1%, 5%, 10%, 15%, or 20% in either direction (greater than or less than) of the number unless otherwise stated or otherwise evident from the context (except where such number would be less than 0% or exceed 100% of a possible value).

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The entire contents of all references, publications, abstracts, and database entries cited in this specification are incorporated by reference herein.

---

What is claimed is:

1. A recombinant adenoviral associated vector (rAAV vector) comprising:
   (a) a first region that encodes one or more first miRNAs comprising a nucleic acid having sufficient sequence complementary with an endogenous mRNA of a subject to hybridize with and inhibit expression of the endogenous mRNA, wherein the endogenous mRNA encodes a first protein having a dominant negative or gain of function mutation; and
   (b) a second region encoding an exogenous mRNA that encodes a second protein, wherein the second protein has an amino acid sequence that is at least 85% identical to the first protein and does not have the dominant negative or gain of function mutation,
   wherein the one or more first miRNAs do not comprise a nucleic acid having sufficient sequence complementary to hybridize with and inhibit expression of the exogenous mRNA, and wherein the first region is positioned between a portion of the second region encoding the last codon of the exogenous mRNA and a polyadenylation sequence of the exogenous mRNA.

2. The rAAV vector of claim 1, further comprising a third region encoding a one or more second miRNAs comprising a nucleic acid having sufficient sequence complementary to hybridize with and inhibit expression of the endogenous mRNA, wherein the third region is positioned within an untranslated portion of the second region.

3. The rAAV vector of claim 2, wherein the third region is between the first codon of the exogenous mRNA and a position 1000 nucleotides upstream of the first codon.

4. The rAAV vector of claim 1, wherein the first region encodes two first miRNAs.

5. The rAAV vector of claim 1, wherein the first region encodes three first miRNAs.

6. The rAAV vector of claim 2, wherein the third region encodes two second miRNAs.

7. The rAAV vector of claim 2, wherein the third region encodes three second miRNAs.

8. The rAAV vector of claim 1, wherein the exogenous mRNA has one or more silent mutations compared with the endogenous mRNA.

9. The rAAV vector of claim 1, further comprising an inverted terminal repeats (ITR) of an AAV serotypes selected from the group consisting of:
   AAV1, AAV2, AAV5, AAV6, AAV6.2, AAV7, AAV8, AAV9, AAV10, AAV11 and variants thereof.

10. The rAAV vector of claim 1, further comprising a promoter operably linked with the region(s) encoding the one or more first miRNAs, the exogenous mRNA, and/or the one or more second miRNAs.

11. The rAAV vector of claim 10, wherein the promoter is a tissue-specific promoter.

12. The rAAV vector of claim 10, wherein the promoter is a β-actin promoter.

13. A recombinant Adeno-Associated Virus (AAV) comprising an rAAV vector of claim 1.

14. A composition comprising the recombinant AAV of claim 13.

15. The composition of claim 14, further comprising a pharmaceutically acceptable carrier.

16. A kit comprising a container housing the composition of claim 14.

17. The kit of claim 16, further comprising written instructions for administering the rAAV to a subject.

* * * * *

SEQUENCE LISTING

<160> NUMBER OF SEQ ID NOS: 32

<210> SEQ ID NO 1
<211> LENGTH: 418
<212> TYPE: PRT
<213> ORGANISM: Homo sapiens

<400> SEQUENCE: 1

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
```

```
                225                 230                 235                 240
Lys Val Pro Met Met Lys Arg Leu Gly Met Phe Asn Ile Gln His Cys
                245                 250                 255
Lys Lys Leu Ser Ser Trp Val Leu Leu Met Lys Tyr Leu Gly Asn Ala
                260                 265                 270
Thr Ala Ile Phe Phe Leu Pro Asp Glu Gly Lys Leu Gln His Leu Glu
                275                 280                 285
Asn Glu Leu Thr His Asp Ile Ile Thr Lys Phe Leu Glu Asn Glu Asp
                290                 295                 300
Arg Arg Ser Ala Ser Leu His Leu Pro Lys Leu Ser Ile Thr Gly Thr
305                 310                 315                 320
Tyr Asp Leu Lys Ser Val Leu Gly Gln Leu Gly Ile Thr Lys Val Phe
                325                 330                 335
Ser Asn Gly Ala Asp Leu Ser Gly Val Thr Glu Glu Ala Pro Leu Lys
                340                 345                 350
Leu Ser Lys Ala Val His Lys Ala Val Leu Thr Ile Asp Glu Lys Gly
                355                 360                 365
Thr Glu Ala Ala Gly Ala Met Phe Leu Glu Ala Ile Pro Met Ser Ile
370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
                405                 410                 415
Gln Lys

<210> SEQ ID NO 2
<211> LENGTH: 394
<212> TYPE: PRT
<213> ORGANISM: Homo sapiens

<400> SEQUENCE: 2

Glu Asp Pro Gln Gly Asp Ala Ala Gln Lys Thr Asp Thr Ser His His
1               5                   10                  15
Asp Gln Asp His Pro Thr Phe Asn Lys Ile Thr Pro Asn Leu Ala Glu
                20                  25                  30
Phe Ala Phe Ser Leu Tyr Arg Gln Leu Ala His Gln Ser Asn Ser Thr
                35                  40                  45
Asn Ile Phe Phe Ser Pro Val Ser Ile Ala Thr Ala Phe Ala Met Leu
            50                  55                  60
Ser Leu Gly Thr Lys Ala Asp Thr His Asp Glu Ile Leu Glu Gly Leu
65                  70                  75                  80
Asn Phe Asn Leu Thr Glu Ile Pro Glu Ala Gln Ile His Glu Gly Phe
                85                  90                  95
Gln Glu Leu Leu Arg Thr Leu Asn Gln Pro Asp Ser Gln Leu Gln Leu
                100                 105                 110
Thr Thr Gly Asn Gly Leu Phe Leu Ser Glu Gly Leu Lys Leu Val Asp
            115                 120                 125
Lys Phe Leu Glu Asp Val Lys Lys Leu Tyr His Ser Glu Ala Phe Thr
130                 135                 140
Val Asn Phe Gly Asp Thr Glu Glu Ala Lys Lys Gln Ile Asn Asp Tyr
145                 150                 155                 160
Val Glu Lys Gly Thr Gln Gly Lys Ile Val Asp Leu Val Lys Glu Leu
                165                 170                 175
Asp Arg Asp Thr Val Phe Ala Leu Val Asn Tyr Ile Phe Phe Lys Gly
```

```
            180                 185                 190
Lys Trp Glu Arg Pro Phe Glu Val Lys Asp Thr Glu Glu Asp Phe
                195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
            290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 3
<211> LENGTH: 418
<212> TYPE: PRT
<213> ORGANISM: Homo sapiens

<400> SEQUENCE: 3

Met Pro Ser Ser Val Ser Trp Gly Ile Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160
```

Leu Tyr His Ser Glu Ala Phe Thr Val Asn Phe Gly Asp Thr Glu
             165                 170                 175

Ala Lys Lys Gln Ile Asn Asp Tyr Val Glu Lys Gly Thr Gln Gly Lys
         180                 185                 190

Ile Val Asp Leu Val Lys Glu Leu Asp Arg Asp Thr Val Phe Ala Leu
         195                 200                 205

Val Asn Tyr Ile Phe Phe Lys Gly Lys Trp Glu Arg Pro Phe Glu Val
210                 215                 220

Lys Asp Thr Glu Glu Asp Phe His Val Asp Gln Val Thr Thr Val
225                 230                 235                 240

Lys Val Pro Met Met Lys Arg Leu Gly Met Phe Asn Ile Gln His Cys
             245                 250                 255

Lys Lys Leu Ser Ser Trp Val Leu Leu Met Lys Tyr Leu Gly Asn Ala
         260                 265                 270

Thr Ala Ile Phe Phe Leu Pro Asp Glu Gly Lys Leu Gln His Leu Glu
         275                 280                 285

Asn Glu Leu Thr His Asp Ile Ile Thr Lys Phe Leu Glu Asn Glu Asp
     290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
             325                 330                 335

Ser Asn Gly Ala Asp Leu Ser Gly Val Thr Glu Glu Ala Pro Leu Lys
         340                 345                 350

Leu Ser Lys Ala Val His Lys Ala Val Leu Thr Ile Asp Lys Lys Gly
         355                 360                 365

Thr Glu Ala Ala Gly Ala Met Phe Leu Glu Ala Ile Pro Met Ser Ile
     370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
             405                 410                 415

Gln Lys

<210> SEQ ID NO 4
<211> LENGTH: 394
<212> TYPE: PRT
<213> ORGANISM: Homo sapiens

<400> SEQUENCE: 4

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

```
Thr Thr Gly Asn Gly Leu Phe Leu Ser Glu Gly Leu Lys Leu Val Asp
            115                 120                 125
Lys Phe Leu Glu Asp Val Lys Lys Leu Tyr His Ser Glu Ala Phe Thr
130                 135                 140
Val Asn Phe Gly Asp Thr Glu Glu Ala Lys Lys Gln Ile Asn Asp Tyr
145                 150                 155                 160
Val Glu Lys Gly Thr Gln Gly Lys Ile Val Asp Leu Val Lys Glu Leu
                165                 170                 175
Asp Arg Asp Thr Val Phe Ala Leu Val Asn Tyr Ile Phe Phe Lys Gly
            180                 185                 190
Lys Trp Glu Arg Pro Phe Glu Val Lys Asp Thr Glu Glu Glu Asp Phe
        195                 200                 205
His Val Asp Gln Val Thr Thr Val Lys Val Pro Met Met Lys Arg Leu
    210                 215                 220
Gly Met Phe Asn Ile Gln His Cys Lys Lys Leu Ser Ser Trp Val Leu
225                 230                 235                 240
Leu Met Lys Tyr Leu Gly Asn Ala Thr Ala Ile Phe Phe Leu Pro Asp
                245                 250                 255
Glu Gly Lys Leu Gln His Leu Glu Asn Glu Leu Thr His Asp Ile Ile
            260                 265                 270
Thr Lys Phe Leu Glu Asn Glu Asp Arg Arg Ser Ala Ser Leu His Leu
        275                 280                 285
Pro Lys Leu Ser Ile Thr Gly Thr Tyr Asp Leu Lys Ser Val Leu Gly
    290                 295                 300
Gln Leu Gly Ile Thr Lys Val Phe Ser Asn Gly Ala Asp Leu Ser Gly
305                 310                 315                 320
Val Thr Glu Glu Ala Pro Leu Lys Leu Ser Lys Ala Val His Lys Ala
                325                 330                 335
Val Leu Thr Ile Asp Lys Lys Gly Thr Glu Ala Ala Gly Ala Met Phe
            340                 345                 350
Leu Glu Ala Ile Pro Met Ser Ile Pro Pro Glu Val Lys Phe Asn Lys
        355                 360                 365
Pro Phe Val Phe Leu Met Ile Glu Gln Asn Thr Lys Ser Pro Leu Phe
    370                 375                 380
Met Gly Lys Val Val Asn Pro Thr Gln Lys
385                 390

<210> SEQ ID NO 5
<211> LENGTH: 1257
<212> TYPE: RNA
<213> ORGANISM: Homo sapiens

<400> SEQUENCE: 5
augccgucuu cugucucgug gggcauccuc cugcuggcag gccugugcug ccuggucccu     60
gucucccugg cugaggaucc cagggagau gcugcccaga agacagauac auccaccau    120 gaucaggauc acccaaccuu caacaagauc accccaacc uggcugaguu cgccuucagc    180
cuauaccgcc agcuggcaca ccaguccaac agcaccaaua ucuucuucuc cccagugagc    240
aucgcuacag ccuuugcaau gcucccccug ggaccaagg cugacacuca cgaugaaauc    300
cuggagggcc ugaauuucaa cccucacgag auuccggagg cucagaucca ugaaggcuuc    360
caggaacucc uccguacccu caaccagcca gacagccagc uccagcugac caccggcaau    420
ggccuguuuc ucagcgaggg ccugaagcua ugggauaagu uuuggaggag uguuaaaaag    480
uuguaccacu cagaagccuu cacugucaac uucggggaca ccgaagaggc caagaaacag    540
```

```
aucaacgauu acguggagaa ggguacucaa gggaaaauug uggauuuggu caaggagcuu    600
gacagagaca caguuuuugc ucuggugaau uacaucuucu uuaaaggcaa augggagaga    660
cccuuugaag ucaaggacac cgaggaagag gacuuccacg uggaccaggu gaccaccgug    720
aaggugccua ugaugaagcg uuuaggcaug uuuaacaucc agcacuguaa gaagcugucc    780
agcugggugc ugcugaugaa auaccugggc aaugccaccg ccaucuucuu ccugccugau    840
gaggggaaac uacagcaccu ggaaaaugaa cucacccacg auaucaucac caaguuccug    900
gaaaaugaag acagaagguc ugccagcuua cauuuaccca aacugccau uacuggaacc      960 uaugaucuga gagcguccu ggucaacug ggcaucacua aggucuucag caaugggcu      1020 gaccucuccg ggucacaga ggaggcaccc ugaagcucu ccaaggccgu gcauaaggcu      1080
gugcugacca ucgacgagaa agggacugaa gcugcugggg ccauguuuuu agaggccaua    1140
cccaugucua uccccccga ggucaaguuc aacaaacccu uugucuucuu aaugauugaa    1200
caaaauacca agucuccccu cuucauggga aaaguggga aucccaccca aaaauaa       1257

<210> SEQ ID NO 6
<211> LENGTH: 3220
<212> TYPE: RNA
<213> ORGANISM: Homo sapiens

<400> SEQUENCE: 6
acaaugacuc cuuucgguaa gugcagugga agcuguacac ugcccaggca aagcguccgg     60
gcagcguagg cgggcgacuc agaucccagc caguggacuu agccccuguu ugcuccuccg    120
auaacugggg ugaccuuggu uaauauucac cagcagccuc ccccguugcc ccucuggauc    180
cacugcuuaa auacgacga ggacagggcc cugucccuc agcuucaggc accaccacug     240
accugggaca gugaaucgac aaugccgucu ucugucucgu gggcauccu ccugcuggca    300 ggccugugcu gccugguccc ugucccccug cgcaggauc cccagggaga ugcugcccag    360
aagacagaua caucccacca ugaucaggau cacccaaccu ucaacaagau cacccccaac    420
cuggcugagu ucgccuucag cccauaccgc cagcuggcac accaguccaa cagcaccaau    480
aucuucuucu ccccagugag caucgcuaca gccuuugcaa ugcuccccu ggggaccaag    540 gcugacacuc acgaugaaau ccuggagggc cugaauuuca accucacgga gauccggag    600 gcucagaucc augaaggcuu ccaggaacuc ucccguaccc ucaaccagcc agacagccag    660
cuccagcuga ccaccggcaa uggccuguuc cucagcgagg gccugaagcu aguggauaag    720
uuuuuggagg auguuaaaaa guuguaccac ucagaagccu ucacugucaa cuucggggac    780
accgaagagg ccaagaaaca gaucaacgau uacguggaga aggguacuca agggaaaauu    840
guggauuugg ucaaggagcu ugacagagac acaguuuuug cucuggugaa uuacaucuuc    900
uuuaaaggca auggagagag acccuuugaa gucaaggaca ccgaggaaga ggacuuccac    960
guggaccagg ugaccaccgu gaaggugccu augaugaagc guuuaggcau guuuaacauc   1020
cagcacugua agaagcuguc cagcugggug cugcugauga auaccugggg caaugccacc   1080
gccaucuucu uccugccuga ugagggaaaa cuacagcacc uggaaaauga acucacccac   1140
gauaucauca ccaaguuccu ggaaaaugaa gacagaaggu cugccagcuu acauuuaccc   1200
aaacugucca uuacuggaac cuaugaucug aagagcgucc uggucaacu gggcaucacu   1260 aaggucuuca gcaaugggc ugaccucucc ggggucacag aggaggcacc ccugaagcuc   1320
uccaaggccg ugcauaaggc ugugcugacc aucgacgaga aagggacuga agcugcuggg   1380
```

```
gccauguuuu uagaggccau acccaugucu auccccccg aggucaaguu caacaaaccc    1440
uuugucuucu uaaugauuga acaaaauacc aagucccccc ucuucauggg aaaaguggug   1500
aaucccaccc aaaaauaacu gccucucgcu ccucaaccc ucccuccau cccuggcccc    1560
cucccuggau gacauuaaag aagguugag cuggucccug ccugcaugug acuguaaauc    1620
ccucccaugu uuucucugag ucccuuug ccugcugagg cuguaugugg gcuccaggua    1680
acagugcugu cuucggcccc ccugaacugu guucauggag caucuggcug gguaggcaca   1740
ugcugggcuu gaauccaggg gggacugaau ccucagcuua cggaccuggg cccaucuguu    1800
ucuggagggc uccagucuuc cuugccugu cuuggaguccc caagaagga aucacagggg    1860
aggaaccaga uaccagccau gaccccaggc uccaccaagc aucuucaugu ccccugcuc    1920
aucccccacu ccccccccacc cagaguugcu cauccgcca gggcuggcug ugcccacccc    1980
aaggcugccc uccuggggc cccagaacug ccugaucgug ccguggccca guuugugcc    2040
aucugcagca acacaagaga gaggacaaug uccuccucuu gacccgcugu caccuaaacca   2100
gacucggcc cugcacccu cagcacuuc uggaaaauga cugaggcaga uucuuccuga    2160
agcccauucu ccauggggca acaaggacac cuauucugu cuugccuuc caucgcugcc    2220
ccagaaagcc ucacauaucu ccguuuagaa caggucccu ucccccaga ugaagaggag    2280
ggucucugcu uguuuucuc uaucuccucc ucagacuuga ccaggccag caggccag      2340
aagaccauua cccauauacc cuucuccucc cuagucacau ggccauaggc cugcugaugg    2400
cucaggaagg ccauugcaag gacuccucag cuagggagga ggaagcacau cacccauuga    2460
cccccgcaac cccucccuu ccuccucuga guccgacug gggccacaug cagccugacu    2520
ucuuugugcc uguugcuguc ccugcagucu cagagggcc accgcagcuc caguggccacg    2580
gcaggaggcu guuccugaau agcccccgug uaaggccca ggagaguccc uccauccucc    2640
aaggcccugc uaaaggacac agcagccagg aagucccccug ggccccuagc ugaaggacag    2700
ccugcuccccu ccgucucuac caggaauggc cuugccuaua ggaaggcacu gccccaucc    2760
aaacuaaucu aggaaucacu gucuaaccac ucacugucau gaauguguac uuaaaggaug    2820
agguugaguc auaccaaaua gugauuucga uagguucaaaa uggugaaauu agcaauucua    2880
caugauucag ucuaaucaau ggauaccgac uguucccac acaagucucc guucucuua    2940
agcuuacuca cugacagccu uucacucucc acaaauacau uaaagauaug gccaucacca    3000
agcccccuag gaugacacca gaccugagag ucugaagacc uggauccaag uucugacuuu    3060
uccccugac agcugugugga ccuucgugaa gucgccaaac cucucugagc cccagucauu    3120
gcuaguaaga ccugccuuug aguugguaug auguucaagu uagauaacaa aauguuuaua    3180
cccauuagaa cagagaauaa auagaacuac auuucuugca                        3220
```

<210> SEQ ID NO 7
<211> LENGTH: 3513
<212> TYPE: RNA
<213> ORGANISM: Homo sapiens

<400> SEQUENCE: 7

```
ugggcaggaa cugggcacug ugcccagggc augcacugcc uccacgcagc aacccucaga     60
guccugagcu gaaccaagaa ggaggagggg gucgggccuc cgaggaaggc cuagccgcug    120
cugcugccag gaauuccagg uuggaggggc ggcaacccuc ugccagccuu caggccacuc    180
uccugugccu gccagaagag acagagcuug aggagagcuu gaggagagca ggaaagggcg    240
gcaguaaguc uucagcauca ggcauuuugg ggugacucag uaaauggu ag aucuugcuac   300
```

```
cagcgaaca gccacuaagg auucugcagu gagagcagag ggccagcuaa guggacucu      360 cccagagacu gucugacuca cgccacccc uccaccuugg acacaggacg cuguggauuu     420
ugagccaggu acaaugacuc cuuucgcagc ucccccguu gccccucugg auccacugcu     480
uaaauacgga cgaggacagg gcccugucuc ucagccuuca ggcaccacca cugaccuggg    540
acagugaauc gacaaugccg ucuucugucu cguggggcau ccuccugcug gcaggccugu    600
gcugccuggu cccugucucc cuggcugagg auccccaggg agaugcugcc cagaagacag    660 auacaucca ccaugaucag gaucacccaa ccuucaacaa gaucaccccc aaccuggcug     720
aguucgccuu cagccauauc cgccagcugg cacaccaguc caacagcacc aauaucuucu    780
ucuccccagu gagcaucgcu acagccuuug caaugcucuc ccuggggacc aaggcugaca    840
cucacgauga aauccuggag ggccugaauu caaccucac ggagauuccg gaggcucaga     900
uccaugaagg cuuccaggaa ucuccccgua cccucaacca gccagacagc cagcuccagc    960
ugaccaccgg caauggccug uuccucagcg agggccugaa gcuaguggau aaguuuuugg   1020
aggauguuaa aaaguugaac cacucagaag ccuucacugu caacuucggg acaccgaag    1080 aggccaagaa acagaucaac gauuacgugg agaagggauc ucaagggaaa auguggauu    1140 uggucaagga gcuugacaga gacacaguuu uugcucuggu gaauuacauc uucuuuaaag   1200
gcaaauggga gagacccuuu gaagucaagg acaccgagga gaggacuuc cacguggacc    1260 aggugaccac cgugaaggug ccuaugauga agcguuuagg caguuuaac auccagcacu     1320 guaagaagcu guccagcugg gugcugcuga ugaaauaccu gggcaaugcc accgccaucu   1380
ucuuccugcc ugaugagggg aaacuacagc accuggaaaa ugaacucacc cacgauauca   1440
ucaccaaguu ccuggaaaau gaagacagaa ggucugccag cuuacauuua cccaaacugu   1500
ccauuacugg aaccuaugau cugaagagcg uccgggguca acugggcauc acuaaggucu   1560
ucagcaaugg ggcugaccuc uccggggauca cagaggaggc accccugaag cucuccaagg   1620
ccgugcauaa ggcugugcug accaucgacg agaaagggac ugaagcugcu ggggccaugu   1680 uuuagaggc cauacccaug ucuauccccc ccgaggucaa guucaacaaa cccuuugucu    1740
ucuuaaugau ugaacaaaau accaaguuuc cccucuucau gggaaaagug gugaauccca    1800
cccaaaaaua acugcucucuc gcuccucaac ccccucccuc cauccuggc cccucccug    1860 gaugacauua agaagggguu gagcuggucc cugccugcau gugacuguaa ucccucca    1920 uguuucucu gagucccccu uugccugcug aggcuguaug ugggucccag guaacagugc    1980
ugucuucggg cccccugaac uguguucaug gagcaucugg cuggguaggc acaugcuggg   2040
cuugaaucca ggggggacug aauccucagc uuacggaccu gggcccaucu guuucuggag   2100
ggcuccaguc uuccuugucc ugucuuggag ucccaagaa ggaaucacag gggaggaacc    2160
agauaccagc caugaccccc aggcuccacca agcaucuuca ugucccccug ucauccccc    2220 acuccccccc cccagaguu gcucauccug ccagggcugg cugugccac cccaaggcug    2280 cccuccuggg ggcccagaa cugccugauc gugccguggc ccaguuuugu ggcaucugca    2340
gcaacacaag agagaggaca augucccuccu cuugacccgc uguaccuaa ccagacucgg    2400 gcccugcacc ucucaggcac uucuggaaaa ugacugaggc agauucuucc ugaagccau     2460 ucuccaugg gcaacaagga caccuauucu guccuugucc uucaucgcu gcccagaaa     2520 gccucacaua ucuccguuua gaaucagguc ccuucucccc agaugaagag gagggucucu   2580
gcuuuguuuu cucuaucucc uccucagacu ugaccaggcc cagcaggccc cagaagacca   2640
```

| | |
|---|---|
| uuacccuaua ucccuucucc ucccuaguca cauggccaua ggccugcuga uggcucagga | 2700 |
| aggccauugc aaggacuccu cagcuauggg agaggaagca caucacccau ugaccccgc | 2760 |
| aaccccuccc uuuccuccuc ugaguccga cuggggccac augcagccug acuucuuugu | 2820 |
| gccuguugcu gucccugcag ucuucagagg gccaccgcag cuccagugcc acggcaggag | 2880 |
| gcuguuccug aauagcCCCu gugguaaggg ccaggagagu ccuuccaucc uccaaggccc | 2940 |
| ugcuaaagga cacagcagcc aggaaguccc cugggcCCcu agcugaagga cagccugcuc | 3000 |
| ccuccgucuc uaccaggaau ggccuugucc uauggaaggc acugcCCcau cccaaacuaa | 3060 |
| ucuaggaauc acugucuaac cacucacugu caugaaugug uacuuaaagg augagguuga | 3120 |
| gucauaccaa auagugauuu cgauaguuca aaauggugaa auuagcaauu cuacaugauu | 3180 |
| cagucuaauc aauggauacc gacuguuucc cacacaaguc uccguuucuc uuaagcuuac | 3240 |
| ucacugacag ccuuucacuc uccacaaaua cauuaaagau auggccauca ccaagccccc | 3300 |
| uaggaugaca ccagaccuga gagucugaag accuggaucc aaguucugac uuuucccccu | 3360 |
| gacagcugug ugaccuucgu gaagucgcca aaccucucug agcccagcuc auugcuagua | 3420 |
| agaccugccu uugaguuggu augauguuca aguuagauaa caaaauguuu aucccauua | 3480 |
| gaacagagaa uaaauagaac uacauuucuu gca | 3513 |

<210> SEQ ID NO 8
<211> LENGTH: 3236
<212> TYPE: RNA
<213> ORGANISM: Homo sapiens

<400> SEQUENCE: 8

| | |
|---|---|
| ugggcaggaa cugggcacug ugcccagggc augcacugcc uccacgcagc aacccucaga | 60 |
| guccugagcu gaaccaagaa ggaggagggg gucgggccuc cgaggaaggc cuagccgcug | 120 |
| cugcugccag gaauuccagg uuggagggc ggcaaccucc ugccagccuu caggccacuc | 180 |
| uccugugccu gccagaagag acagagcuug aggagagcuu gaggagagca ggaaaggugg | 240 |
| gacauugcug cugcugcuca cucaguucca caggacaaug ccgucuucug ucucguggg | 300 |
| cauccccug cuggcaggcc ugugcugccu ggucccuguc ucccuggcug aggauccca | 360 |
| gggagaugcu gcccagaaga cagauacauc ccaccaugau caggaucacc caaccuucaa | 420 |
| caagaucacc cccaaccugg cugaguucgc cuucagccua uaccgccagc uggcacacca | 480 |
| guccaacagc accaauaucu ucuucucccc agugagcauc gcuacagccu uugcaaugcu | 540 |
| cucccugggg accaaggcug acacucacga ugaaauccug gagggccuga auuucaaccu | 600 |
| cacggagauu ccggaggcuc agaucauga aggcuuccag gaacuccuccc guacccucaa | 660 |
| ccagccagac agccagcucc agcugaccac cggcaauggc cuguuccuca gcgagggccu | 720 |
| gaagcuagug gauaaguuuu uggaggaugu uaaaaguug uaccacucag aagccuucac | 780 |
| ugucaacuuc ggggacaccg aagaggccaa gaaacagauc aacgauuacg uggagaaggg | 840 |
| uacucaaggg aaaauugugg auuggucaa ggagcuugac agagacacag uuuuugcucu | 900 |
| ggugaauuac aucuucuuua aaggcaaaug ggagagaccc uuugaaguca aggacaccga | 960 |
| ggaagaggac uuccacgugg accaggugac caccgugaag gugccauaug augaagcguuu | 1020 |
| aggcauguuu aacauccagc acguaagaa gcuguccagc ugggugcugc ugaugaaaua | 1080 |
| ccuggcaau gccaccgcca ucuucuuccu gccugaugag gggaaacuac agcaccugga | 1140 |
| aaaugaacuc acccacgaua ucaucaccaa guuccggaa aaugaagaca gaaggucugc | 1200 |
| cagcuuacau uuacccaaac ugccauuac uggaaccuau gaucugaaga gcguccuggg | 1260 |

```
ucaacugggc aucacuaagg ucuucagcaa uggggcugac cucuccgggg ucacagagga    1320
ggcaccccug aagcucucca aggccgugca uaaggcugug cugaccaucg acgagaaagg    1380
gacugaagcu gcugggggcca uguuuuuaga ggccauaccc augucuaucc ccccgaggu    1440 caaguucaac aaacccuuug ucuucuuaau gauugaacaa aauaccaagu cuccccucuu    1500
caugggaaaa guggugaauc ccacccaaaa auaacugccu cucgcuccuc aacccuccc    1560 cuccauccu ggcccccucc cuggaugaca uuaaagaagg guugagcugg ucccugccug    1620
caugugacug uaaaucccuc ccauguuuuc ucugagucuc ccuuugccug cugaggcugu    1680 auggggcuc cagguaacag ugcugucuuc ggggccccug aacuguguuc auggagcauc    1740
uggcugggua ggcacaugcu gggcuugaau ccagggggga cugaauccuc agcuuacgga    1800
ccugggccca ucuguuucug gagggcucca gucuuccuug uccugucuug gagucccaa    1860 gaaggaauca caggggagga accagauacc agccaugacc ccaggcucca ccaagcaucu    1920 ucauguccc cugcucaucc cccacucccc cccacccaga guugcucauc cugccagggc    1980
uggcugugcc caccccaagg cugcccuccu ggggccccca gaacugccug aucgugccgu    2040
ggcccaguuu uguggcaucu gcagcaacac aagagagagg acaauguccu ccucuugacc    2100
cgcugucacc uaaccagacu cgggcccugc accucucagg cacuucugga aaaugacuga    2160
ggcagauucu uccugaagcc cauucuccau ggggcaacaa ggacaccuau ucuguccuug    2220
uccuuccauc gcugccccag aaagccucac auaucuccgu uuagaaucag gucccuucuc    2280
cccagaugaa gaggagggguc ucugcuuugu uuucucuauc uccuccccag acuugaccag    2340
gcccagcagg cccagaagaa ccauuacccu auaucccuuc uccucccuag ucacauggcc    2400
auaggccugc ugauggcuca ggaaggccau ugcaaggacu ccagcauau ggagaggaa    2460 gcacaucacc cauugacccc cgcaaccccu cccuuccuc ucucugagucc cgacugggggc    2520 cacaugcagc cugacuucuu ugugccuguu gcuguccug cagucuucag agggccaccg    2580
cagcuccagu gccacggcag gaggcuguuc cugaauagcc ccguggguaa gggccaggag    2640
aguccuucca uccuccaagg cccugcuaaa ggacacagca gccaggaagu cccucugggcc    2700 ccuagcugaa ggacagccug cucccuccgu ucuaccagg aauggccuug uccuauggaa    2760
ggcacugccc caucccaaac uaaucuagga aucacugcu aaccacucac ugucaugaau    2820
guguacuuaa aggaugaggu ugagucaac caaauaguga uucgauagu ucaaaauggu    2880 gaaauuagca auucuacaug auucagcuaa aucaauggau accgacuguu ucccacacaa    2940
gucuccuguu ucucuuaagcu uacucacuga cagccuuuca cucuccacaa auacauuaaa    3000
gauauggcca ucaccaagcc cccuaggaug acaccagacc ugagagucug aagaccugga    3060
uccaaguucu gacuuucccc ccugacagcu gugugaccuu cgugaagucg ccaaaccucu    3120
cugagcccca gucauugcua guaagaccug ccuuugaguu gguaugaugu ucaaguuaga    3180
uaacaaaaug uuuauaccca uuagaacaga gaauaaauag aacuacauuu cuugca    3236
```

<210> SEQ ID NO 9
<211> LENGTH: 3532
<212> TYPE: RNA
<213> ORGANISM: Homo sapiens

<400> SEQUENCE: 9

```
ugggcaggaa cugggcacug ugcccagggc augcacugcc uccacgcagc aacccucaga      60
guccugagcu gaaccaagaa ggaggagggg gucgggccuc cgaggaaggc cuagccgcug     120
```

| | |
|---|---:|
| cugcugccag gaauuccagg uuggaggggc ggcaaccucc ugccagccuu caggccacuc | 180 |
| uccugugccu gccagaagag acagagcuug aggagagcuu gaggagagca ggaaaggugg | 240 |
| gacauugcug cugcugcuca cucaguucca cagggcggca guaagucuuc agcaucaggc | 300 |
| auuuuggggu gacucaguaa augguagauc uugcuaccag uggaacagcc acuaaggauu | 360 |
| cugcagugag agcagagggc cagcuaagug guacucuccc agagacuguc ugacucacgc | 420 |
| cacccccucc accuuggaca caggacgcug ugguuucuga gccagcagcc uccccguug | 480 |
| ccccucugga uccacugcuu aaauacggac gaggacaggg cccugucucc ucagcuucag | 540 |
| gcaccaccac ugaccuggga cagugaaucg acaaugccgu cuucugucuc uggggcauc | 600 |
| cuccugcugg caggccugug cugccugguc ccugucuccc uggcugagga uccccaggga | 660 |
| gaugcugccc agaagacaga uacaucccac caugaucagg aucacccaac cuucaacaag | 720 |
| aucacccccca accggcuga guucgccuuc agccuauacc gccagcuggc acaccagucc | 780 |
| aacagcacca auaucuucuu uccccagug agcaucgcua cagccuuugc aaugcucucc | 840 |
| cuggggacca aggcugacac ucacgaugaa uccuggagg ccugaauuu caaccucacg | 900 |
| gagauuccgg aggcucagau ccaugaaggc uuccaggaac uccccguac ccucaaccag | 960 |
| ccagacagcc agcuccagcu gaccaccggc aauggccugu uccucagcga gggcugaag | 1020 |
| cuaguggaua aguuuuugga ggauguuaaa aaguuguacc acucagaagc cuucacuguc | 1080 |
| aacuucgggg acaccgaaga ggccaagaaa cagaucaacg auuacgugga aaggguacu | 1140 |
| caagggaaaa uuguggauuu ggucaaggag cuugacagag acacaguuuu ugcucugug | 1200 |
| aauuacaucu ucuuuaaagg caaauggag agacccuuug aagucaagga caccgaggaa | 1260 |
| gaggacuucc acguggacca ggugaccacc gugaaggugc cuaugaugaa gcguuuaggc | 1320 |
| auguuuaaca uccagcacug uaagaagcug ccagcugggg ugcugcugau gaauauccug | 1380 |
| ggcaaugcca ccgccaucuu cuuccugccu gaugagggga aacuacagca ccuggaaaau | 1440 |
| gaacucaccc acgauaucau caccaaguuc cuggaaaaug aagacagaag gucugccagc | 1500 |
| uuacauuuac ccaaacuguc cauuacugga accaugaauc ugaagagcgu ccuggucaa | 1560 |
| cugggcauca cuaaggucuu cagcaauggg gcugaccucu ccggggucac agaggaggca | 1620 |
| ccccugaagc ucuccaaggc cgugcauaag gcugugcuga ccaucgacga gaaagggacu | 1680 |
| gaagcugcug ggccaugguu uuagaggcc auacccaugu cuaucccccc cgaggucaag | 1740 |
| uucaacaaac ccuuugucuu cuuaaugauu gaacaaaaua ccaagcuccc ccucuucaug | 1800 |
| ggaaaagugg ugaaucccac ccaaaaauaa cugccucucg cuccucaacc ccucccccuc | 1860 |
| auccuggcc cccucccugg augacauuaa agaagggguug agcuggucccc ugccugcaug | 1920 |
| ugacuguaaa uccucccau guuucucug agucucccuu ugccugcuga ggcuguaugu | 1980 |
| gggcuccagg uaacagugcu gcuucgggc cccugaacu guucauggg agcaucuggc | 2040 |
| ugggnaggca caugcugggc uugaauccag ggggacuga auccagcu uacgaccug | 2100 |
| ggcccaucug uuucuggagg gccuccagucu uccuugccu gucuuggagu ccccaagaag | 2160 |
| gaaucacagg ggaggaacca gauaccagcc augaccccag gcuccaccaa gcaucuucau | 2220 |
| gucccccugc ucauccccca cucccccca cccagaguug ucauccugc cagggcuggc | 2280 |
| ugugcccacc ccaaggcugc cuccugggg gccccagaac ugccugaucg ugccguggcc | 2340 |
| caguuuugug gcaucugcag caacacaaga gagaggacaa ugccuccuc uugacccgcu | 2400 |
| gucaccuaac cagacucggg cccugcaccu ucaggcacu ucuggaaaau gacugaggca | 2460 |
| gauucuuccu gaagcccauu cuccaugggg caacaaggac accuauucug uccuuguccu | 2520 |

| | |
|---|---|
| uccaucgcug cccagaaaag ccucacauau cuccguuuag aaucaggucc cuucuccccca | 2580 |
| gaugaagagg agggucucug cuuuguuuuc ucuaucccu cccagacuu gaccaggccc | 2640 |
| agcaggcccc agaagaccau uacccuauau cccuucuccu cccuagucac auggccauag | 2700 |
| gccugcugau ggcucaggaa ggccauugca aggacuccuc agcuauggga gaggaagcac | 2760 |
| aucacccauu gaccccgca accccucccu uccuccucu gaguccgac uggggccaca | 2820 |
| ugcagccuga cuucuuugug ccuguugcug cccugcagu cuucagaggg ccaccgcagc | 2880 |
| uccagugcca cggcaggagg cuguuccuga auagcccug ugguaagggc caggagaguc | 2940 |
| cuuccauccu ccaaggcccu gcuaaaggac acagcagcca ggaagucccc ugggcccua | 3000 |
| gcugaaggac agccugcucc cuccgucucu accaggaaug gccuuguccu auggaaggca | 3060 |
| cugcccauc ccaaacuaau cuaggaauca cugucuaacc acucacuguc augaaugugu | 3120 |
| acuuaaagga ugagguugag ucauaccaaa uagugauuuc gauaguucaa aauggugaaa | 3180 |
| uuagcaauuc uacaugauuc agucuaauca auggauaccg acuguuccc acacaagucu | 3240 |
| ccuguucucu uaagcuuacu cacugacagc cuuucacucu ccacaaauac auuaaagaua | 3300 |
| uggccaucac caagccccu aggaugacac cagaccugag agucugaaga ccuggaucca | 3360 |
| aguucugacu uuuccccug acagcugugu gaccuucgug aagucgccaa accucucuga | 3420 |
| gccccaguca uugcuaguaa gaccugccuu ugaguuggua ugauguucaa guuagauaac | 3480 |
| aaaauguuua uacccauuag aacagagaau aaauagaacu acauuucuug ca | 3532 |

<210> SEQ ID NO 10
<211> LENGTH: 3340
<212> TYPE: RNA
<213> ORGANISM: Homo sapiens

<400> SEQUENCE: 10

| | |
|---|---|
| ugggcaggaa cugggcacug ugcccagggc augcacugcc uccacgcagc aacccucaga | 60 |
| guccugagcu gaaccaagaa ggaggagggg gucgggccuc cgaggaaggc cuagccgcug | 120 |
| cugcugccag gaauuccagg uuggaggggc ggcaaccucc ugccagccuu caggccacuc | 180 |
| uccugugccu gccagaagag acagagcuug aggagagcuu gaggagagca ggaaaggugg | 240 |
| gacauugcug cugcugcuca cucaguucca cagcagccuc ccccguugcc ccucuggauc | 300 |
| cacugcuuaa auacgacga ggacagggcc cugucuccuc agcuucaggc accaccacug | 360 |
| accugggaca gugaaucgac aaugccgucu ucugucucgu gggcauccu ccugcuggca | 420 |
| ggccugugcu gccuggucc ugucucccug gcugaggauc cccagggaga ugcugccag | 480 |
| aagacagaua caucccacca ugaucaggau caccaaaccu ucaacaagau caccccccaac | 540 |
| cuggcugagu cgccuucag ccuauaccgc cagcuggcac accagccaa cagcaccaau | 600 |
| aucuucuucu ccccagugag caucgcuaca gccuugcaa ugcucucccu ggggaccaag | 660 |
| gcugacacuc acgaugaaau ccuggagggc cugaauuuca accucacgga gauuccggag | 720 |
| gcucagaucc augaaggcuu ccaggaacuc cuccguaccc ucaaccagcc agacagccag | 780 |
| cuccagcuga ccaccggcaa uggccuguuc cucagcgagg gccugaagcu aguggauaag | 840 |
| uuuuuggagg auguuaaaaa guuuuaccac ucagaagccu ucacgucaa cuucgggac | 900 |
| accgaagagg ccaagaaaca gaucaacgau uacguggaga aggguacuca agggaaaauu | 960 |
| gugggauugg ucaaggagcu ugacagagac acaguuuuug cucuggugaa uuacaucuuc | 1020 |
| uuuaaaggca aaugggagag accuuugaa gucaaggaca ccgaggaaga ggacuuccac | 1080 |

| | | | | |
|---|---|---|---|---|
| guggaccagg | ugaccaccgu | gaaggugccu | augaugaagc | guuuaggcau guuuaacauc | 1140 |
| cagcacugua | agaagcuguc | cagcugggug | cugcugauga | aauaccuggg caaugccacc | 1200 |
| gccaucuucu | uccugccuga | ugaggggaaa | cuacagcacc | uggaaaauga acucacccac | 1260 |
| gauaucauca | ccaaguuccu | ggaaaaugaa | gacagaaggu | cugccagcuu acauuuaccc | 1320 |
| aaacugucca | uuacuggaac | cuaugaucug | aagagcgucc | uggucaacu gggcaucacu | 1380 |
| aaggucuuca | gcaauggggc | ugaccucucc | ggggucacag | aggaggcacc ccugaagcuc | 1440 |
| uccaaggccg | ugcauaaggc | ugugcugacc | aucgacgaga | aagggacuga agcugcuggg | 1500 |
| gccauguuuu | uagaggccau | acccaugucu | auccccccccg | aggucaaguu caacaaaccc | 1560 |
| uuugucuucu | uaaugauuga | acaaaauacc | aagucccccc | ucuucauggg aaaaguggug | 1620 |
| aaucccaccc | aaaaauaacu | gccucucgcu | ccucaaccccc | uccccuccau cccuggcccc | 1680 |
| cucccuggau | gacauuaaag | aagggguugag | cuggucccug | ccugcaugug acuguaaauc | 1740 |
| ccucccaugu | uuucucugag | ucucccuuug | ccugcugagg | cuguaugugg gcuccaggua | 1800 |
| acagugcugu | cuucgggccc | ccugaacugu | guucauggag | caucuggcug gguaggcaca | 1860 |
| ugcugggcuu | gaauccaggg | gggacugaau | cccucagcuua | cggaccuggg cccaucuguu | 1920 |
| ucuggagggc | uccagucuuc | cuugucccugu | cuuggaguucc | ccaagaagga aucacagggg | 1980 |
| aggaaccaga | uaccagccau | gaccccaggc | uccaccaagc | aucuucaugu ccccccugcuc | 2040 |
| aucccccacu | ccccccccacc | cagaguugcu | cauccugcca | gggcuggcug ugcccacccc | 2100 |
| aaggcugccc | uccuggggggc | cccagaacug | ccugaucgug | ccgguggccca guuuugugc | 2160 |
| aucugcagca | acacaagaga | gaggacaaug | uccccucuu | gacccgcugu caccuaaccca | 2220 |
| gacucgggcc | cugcaccucu | caggcacuuc | uggaaaauga | cugaggcaga uucuuccuga | 2280 |
| agcccauucu | ccauggggca | acaaggacac | cuauucugucu | cuugccuuc caucgcugcc | 2340 |
| ccagaaagcc | ucacauaucu | ccguuuagaa | ucaguccccu | ucucccccaga ugaagaggag | 2400 |
| ggucucugcu | uuguuuucuc | uaucuccucc | ucagacuuga | ccaggccccag caggccccag | 2460 |
| aagaccauua | cccuauaucc | cuucucccucc | cuagucacau | ggccauaggc cugcugaugg | 2520 |
| cucaggaagg | ccauugcaag | gacuccucag | cuauggggaga | ggaagcacau cacccauuga | 2580 |
| cccccgcaac | cccucccuuu | ccuccucuga | gucccgacug | gggccacaug cagccugacu | 2640 |
| ucuuugugcc | uguugcugucc | ccugcagucu | ucagagggcc | accgcagcuc cagugccacg | 2700 |
| gcaggaggcu | guuccugaau | agcccccugug | guaagggcca | ggagaguccu uccauccucc | 2760 |
| aaggcccugc | uaaaggacac | agcagccagg | aagucccccug | ggccccuagc ugaaggacag | 2820 |
| ccugcucccu | ccgucucuac | caggaauggc | cuugccuau | ggaaggcacu gccccauccc | 2880 |
| aaacuaaucu | aggaaucacu | gucuaaccac | ucacugucau | gaaugcguac uuaaaggaug | 2940 |
| agguugaguc | auaccaaaua | gugauuucga | uaguucaaaa | uggugaaauu agcaauucua | 3000 |
| caugauucag | ucuaaucaau | ggauaccgac | uguucccac | acaagucucc uguucucuua | 3060 |
| agcuuacuca | cugacagccu | uucacucucc | acaaauacau | uaaagauaug gccaucacca | 3120 |
| agcccccuag | gaugacacca | gaccugagag | ucugaagacc | uggauccaag uucugacuuu | 3180 |
| ucccccugac | agcugugugu | ccuucgugaa | gucgccaaac | cucucugagc cccagucauu | 3240 |
| gcuaguaaga | ccugccuuug | aguuggguaug | auguucaagu | uagauaacaa aauguuuaua | 3300 |
| cccauuagaa | cagagaauaa | auagaacuac | auuucuugca | | 3340 |

<210> SEQ ID NO 11
<211> LENGTH: 3495

<212> TYPE: RNA
<213> ORGANISM: Homo sapiens

<400> SEQUENCE: 11

```
ugggcaggaa cugggcacug ugcccagggc augcacugcc uccacgcagc aacccucaga      60
guccugagcu gaaccaagaa ggaggagggg gucgggccuc cgaggaaggc cuagccgcug     120
cugcugccag gaauuccagg uuggagggc ggcaaccucc ugccagccuu caggccacuc     180
uccugugccu gccagaagag acagagcuug aggagagcuu gaggagagca ggaaagggcg     240
gcaguaaguc uucagcauca ggcauuuugg ggugacucag uaaaugguag aucuugcuac     300
caguggaaca gccacuaagg auucugcagu gagagcagag ggccagcuaa ugguacucu     360
cccagagacu gucugacuca cgccacccc uccaccuugg acacaggacg cuguggauuc     420
ugagccagca gccucccccg uugcccucu ggauccacug cuuaaauacg gacgaggaca     480
gggcccuguc uccucagcuu caggcaccac cacugaccug ggacagugaa ucgacaaugc     540
cgucuucugu ucugugggc auccuccugc uggcaggccu gugcugccug ucccugucu     600
cccuggcuga ggaucccag ggagaugcug cccagaagac agauacaucc caccaugauc     660
aggaucaccc aaccuucaac aagauccccc caaccuggc ugaguucgcc uucagccuau     720
accgccagcu ggcacaccag uccaacagca ccaauaucuu cuucucccca gugagcaucg     780
cuacagccuu ugcaaugcuc ucccugggga ccaaggcuga cacucacgau gaaauccugg     840
agggccugaa uucaaccuc acggagauuc cggaggcuca gauccaugaa ggcuuccagg     900
aacuccuccg uacccucaac cagccagaca gccagcucca gcugaccacc ggcaauggcc     960
uguuccucag cgagggccug aagcuaguug auaaguuuuu ggaggauguu aaaaguugu    1020
accacucaga agccuucacu gucaacuucg gggacaccga agaggccaag aaacagauca    1080
acgauuacgu ggagaagggu acucaaggga aauugugga uuuggucaag gagcuugaca    1140
gagacacagu uuuugcucug gugaauuaca ucuucuuuaa aggcaaaugg gagagacccu    1200
uugaagucaa ggacaccgag gaagaggacu uccacgugga ccaggugacc accgugaagg    1260
ugccuaugau gaagcguuua ggcauguuua acauccagca cuguaagaag cuguccagcu    1320
gggugcugcu gaugaaauac cugggcaaug ccaccgccau cuucuuccug ccugaugagg    1380
ggaaacuaca gcaccuggaa aaugaacuca cccacgauau caucaccaag uccuggaaa    1440
augaagacag aaggucugcc agcuuacauu uacccaaacu guccauuacu ggaaccuaug    1500
aucugaagag cguccugggu caacugggca ucacuaaggu cuucagcaau ggggcugacc    1560
ucuccggggu cacagaggag gcacccccuga agcucccaa ggccgugcau aaggcugugc    1620
ugaccaucga cgagaagggg acugaagcug cuggggccau guuuuuagag gccauaccca    1680
ugucuauccc ccccgagguc aaguucaaca acccccuugu cuucuaaaug auugaacaaa    1740
auaccaaguc uccccucuuc augggaaaag uggugaaucc caccccaaaaa uaacugccuc    1800
ucgcccucca ccccucccc uccauccug gcccccuccc uggaugacau uaaagaaggg    1860
uugagcuggu cccugccugc augugacugu aaaucccucc caugauuucu cugagucucc    1920
cuuugccugc ugaggcugua gugggcucc agguaacagu gcugcuucg ggcccccuga    1980
acuguguuca uggagcaucu ggcugggugag cacaugcug ggcuugaauc cagggggac    2040
ugaauccuca gcuacggac cugggccau cuguuucugg agggcuccag ucuuccuguu    2100
ccugucuugu agucccaag aaggaaucac aggggaggaa ccagauacca gccaugaccc    2160
caggcuccac caagcaucuu caugucccc ugcucaucccc cacucccc ccacccagag    2220
```

| | | | | |
|---|---|---|---|---|
| uugcucaucc | ugccagggcu | ggcugugccc | accccaaggc | ugcccuccug | ggggcccag | 2280 |
| aacugccuga | ucgugccgug | gcccaguuuu | guggcaucug | cagcaacaca | agagagagga | 2340 |
| caauguccuc | ucuugacccc | gcugucaccu | aaccagacuc | gggcccugca | ccucucaggc | 2400 |
| acuucuggaa | aaugacugag | gcagauucuu | ccugaagccc | auucuccaug | ggcaacaag | 2460 |
| gacaccuauu | cuguccuugu | ccuccaucg | cugccccaga | aagccucaca | uaucuccguu | 2520 |
| uagaaucagg | ucccuucucc | ccagaugaag | aggagggucu | cugcuuugu | uucucuaucu | 2580 |
| ccuccucaga | cuugaccagg | cccagcaggc | cccagaagac | cauuacccua | uccccuucu | 2640 |
| ccucccuagu | cacauggcca | uaggccugcu | gauggcucag | gaaggccauu | gcaaggacuc | 2700 |
| cucagcuaug | ggagaggaag | cacaucaccc | auugaccccc | gcaacccuc | ccuuccucc | 2760 |
| ucugaguccc | gacuggggcc | acaugcagcc | ugacuucuuu | gugccuguug | cuguccuge | 2820 |
| agucuucaga | gggccaccgc | agcuccagug | ccacggcagg | aggcuguucc | ugaauagccc | 2880 |
| cuguggugaag | ggccaggaga | guccuuccau | ccuccaaggc | ccugcuaaag | gacacagcag | 2940 |
| ccaggaaguc | cccuggggccc | cuagcugaag | gacagccugc | ucccuccguc | ucuaccagga | 3000 |
| auggccuugu | ccuauggaag | gcacugcccc | aucccaaaacu | aaucuaggaa | ucacugucua | 3060 |
| accacucacu | gucaugaaug | uguacuuaaa | ggaugagguu | gagucauacc | aaauagugau | 3120 |
| uucgauaguu | caaaaugguvg | aaauuagcaa | uucuacauga | uucagcuaaa | ucaauggaua | 3180 |
| ccgacuguuu | cccacacaag | uccugguuc | ucuuaagcuu | acacacgac | agccuuucac | 3240 |
| ucuccacaaa | uacauuaaag | auauggccau | caccaagccc | ccuaggauga | caccagaccu | 3300 |
| gagagucuga | agaccuggau | ccaaguucug | acuuuuccccc | cugacagcug | ugugaccuuc | 3360 |
| gugaagucgc | caaaccucuc | ugagcccccag | ucauugcuag | uaagaccugc | cuuugaguug | 3420 |
| guaugauguu | caaguuagau | aacaaaaugu | uuauacccau | uagaacagag | aauaaauaga | 3480 |
| acuacauuuc | uugca | | | | | 3495 |

<210> SEQ ID NO 12
<211> LENGTH: 3492
<212> TYPE: RNA
<213> ORGANISM: Homo sapiens

<400> SEQUENCE: 12

| | | | | |
|---|---|---|---|---|
| ugggcaggaa | cugggcacug | ugcccagggc | augcacugcc | uccacgcagc | aacccucaga | 60 |
| guccugagcu | gaaccaagaa | ggaggagggg | gucgggccuc | cgaggaaggc | cuagccgcug | 120 |
| cugcugccag | gaauuccagg | uuggagggc | ggcaacccuc | ugccagccuu | caggccacuc | 180 |
| uccugugccu | gccagaagag | acagagcuug | aggagagcuu | gaggagagca | ggaaagggcg | 240 |
| gcaguaaguc | uucagcauca | ggcauuuugg | ggugacucag | uaaaugguag | aucuugcuac | 300 |
| caguggaaca | gccacuaagg | auucugcagu | gagagcagag | ggccagcuaa | gugguacucu | 360 |
| cccagagacu | gucugacuca | cgccacccccc | uccaccuugg | acacaggacg | cuguggguuc | 420 |
| ugagccagcc | uccccccguug | ccccucugga | uccacugcuu | aaauacggac | gaggacaggg | 480 |
| cccugucucc | ucagcuucag | gcaccaccac | ugaccuggga | cagugaaucg | acaaugccgu | 540 |
| cuucugucuc | gugggcauc | cuccugcugg | caggccugug | cugccugguc | ccugucccc | 600 |
| uggcugagga | uccccaggga | gaugcugccc | agaagacaga | uacaucccac | caugaucagg | 660 |
| aucacccaac | cuucaacaag | auccccccca | accuggcuga | guucgccuuc | agccuauacc | 720 |
| gccagcuggc | acaccagucc | aacagcacca | auaucuucuu | cuccccagug | agcaucgcua | 780 |
| cagccuuugc | aaugcucucc | cuggggacca | aggcugacac | ucacgaugaa | auccuggagg | 840 |

-continued

```
gccugaauuu caaccucacg gagauuccgg aggcucagau ccaugaaggc uuccaggaac    900
uccuccguac ccucaaccag ccagacagcc agcuccagcu gaccaccggc aauggccugu    960
uccucagcga gggccugaag cuaguggaua aguuuuugga ggauguuaaa aaguuguacc   1020
acucagaagc cuuacuguc aacuucgggg acaccgaaga ggccaagaaa cagaucaacg    1080
auuacgugga gaagguacu caagggaaaa ugugauuu ggucaaggag cuugacagag      1140
acacaguuuu ugcucgguug aauuacaucu ucuuuaaagg caaaugggag agacccuuug   1200
aagucaagga caccgaggaa gaggacuucc acguggacca ggugaccacc gugaaggugc   1260
cuaugaugaa gcguuuaggc auguuuaaca uccagcacug uaagaagcug uccagcuggg   1320
ugcugcugau gaaauaccug ggcaaugcca ccgccaucuu cuuccugccu gaugagggga   1380
aacuacagca ccuggaaaau gaacucaccc acgauaucau caccaaguuc cuggaaaaug   1440
aagacagaag gucugccagc uuacauuuac ccaaacuguc cauuacugga accaugauc    1500
ugaagagcgu ccuggucaa cugggcauca cuaaggucuu cagcaauggg gcugaccucu    1560
ccggggucac agaggaggca ccccugaagc ucuccaaggc cgugcauaag gcugugcuga   1620
ccaucgacga gaaagggacu gaagcugcug gggccauguu uuuagaggcc auacccaugu   1680
cuauccccc cgaggucaag uucaacaaac ccuuugucuu cuuaaugauu gaacaaaaua    1740
ccaagcuccc ccucuucaug ggaaaagugg ugaaucccac ccaaaaauaa cugcccucg    1800
cuccucaacc ccuccccucc aucccuggcc cccucccugg augacauuaa agaagggu     1860
agcugguccc ugccugcaug ugacuguaaa ucccucccau guuuucucug agucucccuu   1920
ugccugcuga ggcuguaugu gggcuccagg uaacagugcu gcuucgggc ccccugaacu    1980
guguucaugg agcaucuggc ugguaggca caugcuggc uugaauccag ggggacuga      2040
auccucagcu uacggaccug ggcccaucug uuucggagg gcuccagucu ccuugugccu    2100
gucuggagu ccccaagaag gaaucacagg ggaggaacca gauaccagcc augaccccag    2160
gcuccaccaa gcaucuucau guccccgc ucauccccca cuccccccca cccagaguug     2220
cucauccugc cagggcuggc ugugcccacc ccaaggcugc ccuccugggg gcccagaac    2280
ugccugaucg ugccguggcc caguuuugug gcaucugcag caacacaaga gagaggacaa   2340
uguccuccuc uugacccgcu gucaccuaac cagacucggg cccugcaccu ucaggcacu    2400
ucuggaaaau gacugaggca gauucuuccu gaagcccauu uccauggggg caacaaggac   2460
accuauucug uccuugaccu ccaucgcuc ccccagaaag ccucacauau uccgguuuag    2520
aaucaggucc cuucucccca gaugaagagg agggucucg cuuuguuuuc ucuaucuccu    2580
cccucagacuu gaccaggccc agcaggcccc agaagaccau ucccuauau cccuucuccu    2640
cccuagucac auggccauag gccugcugau ggcucaggaa ggccauugca aggacuccuc   2700
agcuauggga gaggaagcac aucacccauu gaccccccgca accccucccu uccuccucu   2760
gagucccgac ugggggccaca ugcagccuga cuucuuugug ccguugcug ucccugcagu   2820
cuucagaggg ccaccgcagc uccagugcca cggcaggagg cuguuccuga auagcccug    2880
ugguaagggc caggagaguc cuuccauccu ccaaggcccu gcuaaaggac acagcagcca   2940
ggaaguccc uggggcccua gcugaaggac agccugcucc cuccgucucu accaggaaug   3000
gccuuguccu auggaaggca cugccccauc ccaaacuaau cuaggaauca cugucuaacc    3060
acucacuguc augaaugugu acuuaaagga ugagguugag ucauaccaaa uagugauuuc   3120
gauaguucaa aauggugaaa uuagcaauuc uacaugauuc agcuaauca auggauaccg    3180
```

| | |
|---|---:|
| acuguuuccc acacaagucu ccuguucucu uaagcuuacu cacugacagc cuuucacucu | 3240 |
| ccacaaauac auuaaagaua uggccaucac caagcccccu aggaugacac cagaccugag | 3300 |
| agucugaaga ccuggaucca aguucugacu uuuccccug acagcugugu gaccuucgug | 3360 |
| aagucgccaa accucucuga gccccaguca uugcuaguaa gaccugccuu ugaguuggua | 3420 |
| ugauguucaa guuagauaac aaaauguuua uacccauuag aacagagaau aaauagaacu | 3480 |
| acauuucuug ca | 3492 |

<210> SEQ ID NO 13
<211> LENGTH: 3510
<212> TYPE: RNA
<213> ORGANISM: Homo sapiens

<400> SEQUENCE: 13

| | |
|---|---:|
| ugggcaggaa cugggcacug ugcccagggc augcacugcc uccacgcagc aacccucaga | 60 |
| guccugagcu gaaccaagaa ggaggagggg gucgggccuc cgaggaaggc cuagccgcug | 120 |
| cugcugccag gaauuccagg uuggagggc ggcaaccucc ugccagccuu caggccacuc | 180 |
| uccugugccu gccagaagag acagagcuug aggagagcuu gaggagagca ggaaagggcg | 240 |
| gcaguaaguc uucagcauca ggcauuuugg ggugacucag uaaaugguag aucuugcuac | 300 |
| cagugggaaca gccacuaagg auucugcagu gagagcagag ggccagcuaa gugguacucu | 360 |
| cccagagacu gucugacuca cgccaccccc uccaccuugg acacaggacg cuguggauuc | 420 |
| ugagccaggu acaaugacuc cuuucgccuc ccccguugcc ccucuggauc cacugcuuaa | 480 |
| auacggacga ggacagggcc cugucuccuc agcuucaggc accaccacug accugggaca | 540 |
| gugaaucgac aaugccgucu ucugucucgu ggggcauccu ccugcuggca ggccugugcu | 600 |
| gccugguccc ugucucccug gcugaggauc cccagggaga ugcugcccag aagacagaua | 660 |
| caucccacca ugaucaggau cacccaaccu ucaacaagau caccccccaac cuggcugagu | 720 |
| ucgccuucag ccuauaccgc cagcuggcac accaguccaa cagcaccaau aucuucuucu | 780 |
| ccccagugag caucgcuaca gccuuugcaa ugcucucccu ggggaccaag gcugacacuc | 840 |
| acgaugaaau ccuggaggc cugaauuuca accucacgga gauuccgag gcucagaucc | 900 |
| augaaggcuu ccaggaacuc cuccguaccc ucaaccagcc agacagccag cuccagcuga | 960 |
| ccaccggcaa uggccuguuc cucagcgagg gccugaagcu aguggauaag uuuuuggagg | 1020 |
| auguuaaaaa guuguaccac ucagaagccu ucacugucaa cuucgggac accgaagagg | 1080 |
| ccaagaaaca gaucaacgau uacguggaga agggacucua agggaaaauu guggauuugg | 1140 |
| ucaaggagcu ugacagagac acaguuuuug cucuggugaa uuacaucuuc uuuaaaggca | 1200 |
| aaugggagag accccuuugaa gucaaggaca ccgaggaaga ggacuuccac guggaccagg | 1260 |
| ugaccaccgu gaaggugccu augaugaagc guuuaggcau guuuaacauc cagcacugua | 1320 |
| agaagcuguc cagcggggug cugcugauga auaccugggg caaugccacc gccaucuucu | 1380 |
| uccugccuga ugagggaaa cuacagcacc uggaaaauga acucacccac gauaucauca | 1440 |
| ccaaguuccu ggaaaaugaa gacagaaggu cugccagcuu acauuucccc aaacugucca | 1500 |
| uuacuggaac cuaugaucug aagagcguccc ugggucaacu gggcaucacu aaggucuuca | 1560 |
| gcaaugggc ugaccucucc ggggucacag aggaggcacc ccugaagcuc uccaaggccg | 1620 |
| ugcauaaggc ugugcugacc aucgacgaga agggacugaa agcugcuggg gccauguuuu | 1680 |
| uagaggccau acccaugucu aucccccccg aggucaaguu caacaaaccc uuugucuucu | 1740 |
| uaaugauuga acaaaauacc aagucucccc ucuucauggg aaaaguggug aaucccaccc | 1800 |

| | | | | | |
|---|---|---|---|---|---|
| aaaaauaacu | gccucucgcu | ccucaacccc | uccccuccau | cccuggcccc | cucccuggau | 1860 |
| gacauuaaag | aaggguugag | cuggucccug | ccugcaugug | acuguaaauc | ccucccaugu | 1920 |
| uuucucugag | ucuccuuug | ccugcugagg | cuguauggg | gcuccaggua | acagugcugu | 1980 |
| cuucgggccc | ccugaacugu | guucauggag | caucuggcug | gguaggcaca | ugcugggcuu | 2040 |
| gaauccaggg | gggacugaau | ccucagcuua | cggaccuggg | cccaucuguu | ucuggagggc | 2100 |
| uccagucuuc | cuuguccugu | cuuggagucc | ccaagaagga | aucacagggg | aggaaccaga | 2160 |
| uaccagccau | gaccccaggc | uccaccaagc | aucuucaugu | ccccugcuc | auccccacu | 2220 |
| ccccccacc | cagaguugcu | cauccugcca | gggcuggcug | ugccacccc | aaggcugccc | 2280 |
| uccuggggc | cccagaacug | ccugaucgug | ccguggccca | guuugugcc | aucugcagca | 2340 |
| acacaagaga | gaggacaaug | uccccucuu | gaccgcgu | caccuaacca | gacucgggcc | 2400 |
| cugcaccucu | caggcacuuc | uggaaaauga | cugaggcaga | uucuuccuga | agcccauucu | 2460 |
| ccaugggca | acaaggacac | cuauucuguc | cuuguccuuc | caucgcugcc | ccagaaagcc | 2520 |
| ucacauaucu | ccguuuagaa | ucagguccu | ucuccccaga | ugaagaggag | ggucucugcu | 2580 |
| uuguuucuc | uaucuccucc | ucagacuuga | ccaggcccag | caggcccag | aagaccauua | 2640 |
| cccuauaucc | cuucuccucc | cuagucacau | ggccauaggc | cugcugaugg | ucaggaagg | 2700 |
| ccauugcaag | gacuccucag | cuaugggaga | ggaagcacau | cacccauuga | ccccgcaac | 2760 |
| cccucccuuu | ccuccucuga | gucccgacug | gggccacaug | cagccugacu | ucuuugugcc | 2820 |
| uguugcuguc | ccugcagucu | ucagagggcc | accgcagcuc | cagugccacg | gcaggaggcu | 2880 |
| guuccugaau | agcccugug | guaagggcca | ggagaguccu | uccauccucc | aaggcccugc | 2940 |
| uaaaggacac | agcagccagg | aaguccccug | ggccccuagc | ugaaggacag | ccugcucccu | 3000 |
| ccgucucuac | caggaauggc | cuuguccuau | ggaaggcacu | gccccauccc | aaacuaaucu | 3060 |
| aggaaucacu | gucuaaccac | ucacugucau | gaaugcuac | uuaaaggaug | agguugaguc | 3120 |
| auaccaaaua | gugauuucga | uaguucaaaa | ugguuaaauu | agcaauucua | caugauucag | 3180 |
| ucuaaucaau | ggauaccgac | uguuccac | acaagcuccc | uguucucuua | agcuuacuca | 3240 |
| cugacagccu | uucacucucc | acaaauacau | uaaagauaug | gccaucacca | agcccccuag | 3300 |
| gaugacacca | gaccugagag | ucugaagacc | uggauccaag | uucugacuuu | ucccccugac | 3360 |
| agcuguguga | ccuucgugaa | gucgccaaac | cucucugagc | cccagucauu | gcuaguaaga | 3420 |
| ccugccuuug | aguugguaug | auguucaagu | uagauaacaa | aauguuuaua | cccauuagaa | 3480 |
| cagagaauaa | auagaacuac | auuucuugca | | | | 3510 |

<210> SEQ ID NO 14
<211> LENGTH: 3303
<212> TYPE: RNA
<213> ORGANISM: Homo sapiens

<400> SEQUENCE: 14

| | | | | | |
|---|---|---|---|---|---|
| ugggcaggaa | cugggcacug | ugcccagggc | augcacugcc | uccacgcagc | aacccucaga | 60 |
| guccugagcu | gaaccaagaa | ggaggagggg | gucgggccuc | cgaggaaggc | cuagccgcug | 120 |
| cugcugccag | gaauuccagg | uuggagggc | ggcaaccucc | ugccagccuu | caggccacuc | 180 |
| uccugugccu | gccagaagag | acagagcuug | aggagagcuu | gaggagagca | ggaaagcagc | 240 |
| cucccccguu | gccccucugg | auccacugcu | uaaauacgga | cgaggacagg | gcccugucuc | 300 |
| cucagcuuca | ggcaccacca | cugaccuggg | acagugaauc | gacaaugccg | ucuucugucu | 360 |

```
cgugggcau  ccuccugcug  gcaggccugu  gcugccuggu  cccugucucc  cuggcugagg   420
auccccaggg  agaugcugcc  cagaagacag  auacauccca  ccaugaucag  gaucacccaa   480
ccuucaacaa  gaucacccc   aaccuggcug  aguucgccuu  cagccuauac  cgccagcugg   540
cacaccaguc  caacagcacc  aauaucuucu  ucucccagu   gagcaucgcu  acagccuuug   600
caaugcucuc  ccuggggacc  aaggcugaca  cucacgauga  aauccuggag  ggccugaauu   660
ucaaccucac  ggagauuccg  gaggcucaga  uccaugaagg  cuuccaggaa  ucccccgua    720 cccucaacca  gccagacagc  cagcuccagc  ugaccaccgg  caauggccug  uccucagcg    780 agggccugaa  gcuaguggau  aaguuuuugg  aggauguuaa  aaaguuguac  cacucagaag   840
ccuucacugu  caacuucggg  gacaccgaag  aggccaagaa  acagaucaac  gauuacgugg   900 agaagggguac  ucaagggaaa  auuguggauu  uggucaagga  gcuugacaga  gacacaguu    960 uugcucuggu  gaauuacauc  uucuuuaaag  gcaaauggga  gagacccuuu  gaagucaagg  1020
acaccgagga  agaggacuuc  cacgguggacc  aggugaccac  cgugaaggug  ccuaugauga  1080
agcguuuagg  cauguuuaac  auccagcacu  guaagaagcu  guccagcugg  gugcugcuga  1140
ugaaauaccu  gggcaaugcc  accgccaucu  ucuuccugcc  ugaugagggg  aaacuacagc  1200
accuggaaaa  ugaacucacc  cacgauauca  ucaccaaguu  ccuggaaaau  gaagacagaa  1260
ggucugccag  cuuacauuua  cccaaacugu  ccauuacugg  aaccaaugau  cugaagagcg  1320
uccgggguca  acugggcauc  acuaaggucu  ucagcaaugg  ggcugaccuc  uccggggca   1380 cagaggaggc  acccugaag   cucuccaagg  ccgugcauaa  ggcugugcug  accaucgacg  1440
agaaagggac  ugaagcugcu  ggggccaugu  uuuagaggc   cauacccaug  ucuauccccc  1500
ccgaggucaa  guucaacaaa  cccuuugucu  ucuuaaugau  ugaacaaaau  accaagucuc  1560
cccucuucau  gggaaaagug  gugaauccca  cccaaaaaua  acugcucucu  gcuccucaac  1620
ccccucccuc  caucccuggc  ccccucccug  gaugacauua  agaagggguu  gagcuggucc  1680
cugccugcau  gugacugaa   aucccucca   uguuucucu   gagucccccu  uugccugcug  1740
aggcuguaug  ugggcuccag  guaacaguc   ugucuucggg  ccccugaac   uguguucaug  1800 gagcaucugg  cuggguaggc  acaugcuggg  cuugaaucca  gggggacug   aauccucagc  1860 uuacggaccu  gggcccaucu  guuucuggag  ggcuccaguc  uccuuguucc  ugucuuggag  1920 ucccaagaa   ggaaucacag  gggaggaacc  agauaccagc  caugacccca  ggcuccacca  1980
agcaucuuca  uguccccug   cucauccccc  acucccccc   acccagaguu  gcucauccug  2040
ccagggcugg  cugugcccac  cccaaggcug  ccuccuggg   ggcccagaa   cugccugauc  2100 gugccgguggc  ccaguuuugu  ggcaucugca  gcaacacaag  agagaggaca  auguccuccu  2160
cuugacccgc  ugcaccuaa   ccagacucgg  gcccugcacc  ucuccaggcac  uucuggaaaa  2220 ugacugaggc  agauucuucc  ugaagcccau  ucuccauggg  gcaacaagga  caccuauucu  2280
guccuugucc  uuccaucgcu  gccccagaaa  gccucacaua  ucccguuua   gaaucagguc  2340 ccuucucccc  agaugaagag  gagggucucu  gcuuuguuuu  ucuaucccc   uccucagacu  2400 ugaccaggcc  cagcaggccc  cagaagacca  uuacccuaua  uccuucucc   ucccuaguca  2460 cauggccaua  ggccugcuga  uggcucagga  aggccauugc  aaggaccccu  cagcuauggg  2520
agaggaagca  caucacccau  ugaccccgc   aaccccuccc  uuuccuccuc  ugaguccga   2580 cuggggccac  augcagccug  acuucuuugu  gccuguugcu  gcccugcag   ucuucagagg  2640 gccaccgcag  cuccagugcc  acggcaggag  gcuguuccug  aauagcccu   guguaaggg   2700 ccaggagagu  ccuuccaucc  uccaaggccc  ugcuaaagga  cacagcagcc  aggaagucc   2760
```

| | |
|---|---:|
| cugggccccu agcugaagga cagccugcuc ccuccgucuc uaccaggaau ggccuugucc | 2820 |
| uauggaaggc acugccccau cccaaacuaa ucuaggaauc acugucuaac cacucacugu | 2880 |
| caugaaugug acuuaaagg augagguuga gucauaccaa auagugauuu cgauaguuca | 2940 |
| aaauggugaa auuagcaauu cuacaugauu cagucuaauc aauggauacc gacguuuuuc | 3000 |
| cacacaaguc uccuguucuc uuaagcuuac ucacugacag ccuuucacuc uccacaaaua | 3060 |
| cauuaaagau auggccauca ccaagccccc uaggaugaca ccagaccuga gucugaag | 3120 |
| accuggaucc aaguucugac uuuucccccu gacagcugug ugaccuucgu gaagucgcca | 3180 |
| aaccucucug agccccaguc auugcuagua agaccugccu uugaguuggu augauguuca | 3240 |
| aguuagauaa caaaauguuu uacccauua gaacagaaa uaaauagaac uacauuucuu | 3300 |
| gca | 3303 |

<210> SEQ ID NO 15
<211> LENGTH: 3300
<212> TYPE: RNA
<213> ORGANISM: Homo sapiens

<400> SEQUENCE: 15

| | |
|---|---:|
| ugggcaggaa cugggcacug ugcccagggc augcacugcc uccacgcagc aacccucaga | 60 |
| guccugagcu gaaccaagaa ggaggagggg gucgggccuc cgaggaaggc cuagccgcug | 120 |
| cugcugccag gaauuccagg uuggagggc ggcaaccucc ugccagccuu caggccacuc | 180 |
| uccugugccu gccagaagag acagagcuug aggagagcuu gaggagagca ggaaagccuc | 240 |
| ccccguugcc ccucuggauc cacugcuuaa uacggacga ggacagggcc cugucuccuc | 300 |
| agcuucaggc accaccacug accugggaca gugaaucgac aaugccgucu ucugucucgu | 360 |
| ggggcauccu ccugcuggca ggccugugcu gccuggucccc ugucucccug gcugaggauc | 420 |
| cccagggaga ugcugcccag aagacagaua cauccaccca ugaucaggau cacccaaccu | 480 |
| ucaacaagau caccccccaac cuggcugagu ucgccuucag ccuauaccgc cagcuggcac | 540 |
| accaguccaa cagcaccaau aucuucuucu ccccagugag caucgcuaca gccuuugcaa | 600 |
| ugcucucccu ggggaccaag gcugacacuc acgaugaaau ccuggagggc cugaauuuca | 660 |
| accucacgga gauuccggag gcucagauuc augaaggcuu ccaggaacuc cuccguaccc | 720 |
| ucaaccagcc agacagccag cuccagcuga ccaccggcaa uggccuguuc cucagcgagg | 780 |
| gccugaagcu aguggauaag uuuuuggagg auguuaaaaa guuguaccac ucagaagccu | 840 |
| ucacugucaa cuucggggac accgaagagg ccaagaaaca gaucaacgau uacguggaga | 900 |
| agguacuca agggaaaauu guggauuugg ucaaggagcu ugacagagac acaguuuug | 960 |
| cucuggugaa uuacaucuuc uuuaaaggca aaugggagag acccuuugaa gucaaggaca | 1020 |
| ccgaggaaga ggacuuccac guggaccagg ugaccaccgu gaaggugccu augaugaagc | 1080 |
| guuuaggcau guuuaacauc cagcacugua agaagcuguc cagcugggug cugcugauga | 1140 |
| aauaccuggg caaugccacc gccaucuucu uccugccuga ugagggaaa cuacagcacc | 1200 |
| uggaaaauga acucacccac gauaucauca ccaaguccuu ggaaaaugaa gacagaaggu | 1260 |
| cugccagcuu acauuuaccc aaacugucca uuacuggaac cuaugaucug aagagcguucc | 1320 |
| uggguucaacu gggcaucacu aaggucuuca gcaaugggc ugaccucucc gggucacag | 1380 |
| aggaggcacc ccugaagcuc uccaaggccg ugcauaaggc ugugcugacc aucgacgaga | 1440 |
| aagggacuga agcugcuggg gccauguuuu uagaggccau acccaugucu auccccccg | 1500 |

| | |
|---|---|
| aggucaaguu caacaaaccc uuugucuucu aaugauuga caaaauacc aagucccccc | 1560 |
| ucuucauggg aaaagugguu aaucccaccc aaaaauaacu gccucucgcu ccucaacccc | 1620 |
| uccccuccau cccuggcccc ucccuggau gacauuaaag aagggungag cuggucccug | 1680 |
| ccugcaugu acuguaaauc ccucccaugu uuucucugag ucccuuug ccugcugagg | 1740 |
| cuguaugugg gcuccaggua acagugcugu cuucgggccc ccugaacugu guucauggag | 1800 |
| caucuggcug gguaggcaca ugcugggcuu gaaccaggg gggacugaau ccucagcuua | 1860 |
| cggaccuggg cccaucuguu ucuggagggc uccagucuuc cuuguccugu cuuggaguccc | 1920 |
| ccaagaagga aucacagggg aggaaccaga uaccagccau gaccccaggc uccaccaagc | 1980 |
| aucuucaugu cccccugcuc aucccccacu ccccccacc cagaguugcu caucgcuca | 2040 |
| gggcuggcug ugcccacccc aaggcugccc uccggggggc cccagaacug ccugaucgug | 2100 |
| ccguggccca guuugugg aucugcagca acacaagaga gaggacaaug uccuccucuu | 2160 |
| gacccgcugu caccuaacca gacucggggcc cugcaccucu caggcacuc uggaaaauga | 2220 |
| cugaggcaga uucuuccuga agcccauucu ccauggggca caaggacac cuauucuguc | 2280 |
| cuuguccuuc caucgcugcc cagaaagcc ucacauaucu ccguuuagaa ucaggucccu | 2340 |
| ucucccccaga ugaagaggag ggucucugcu uuguuucuc uaucuccucc ucagacuuga | 2400 |
| ccaggcccag caggcccag aagaccauua cccauauacc cuucccucc cuagucacau | 2460 |
| ggccauaggc cugcugaugg ucaggaagg ccauugcaag gacuccucag cuaugggaga | 2520 |
| ggaagcacau caccccauuga cccccgcaac ccucccuuu ccucccuga gucccgacug | 2580 |
| gggccacaug cagccugacu ucuuugccc uguugcuguc ccugcagucu ucagagggcc | 2640 |
| accgcagcuc cagugccacg gcaggaggcu guuccugaau agcccugug uaagggcca | 2700 |
| ggagaguccu uccauccucc aaggcccugc uaaaggacac agcagccagg aagucccccug | 2760 |
| ggccccuagc ugaaggacag ccugcucccu ccgucucuac caggaauggc cuuguccuau | 2820 |
| ggaaggcacu gccccauccc aaacuaaucu aggaaucacu gucuaaccac ucacugucau | 2880 |
| gaauguguac uuaaaggaug agguugaguc auaccaaaua gugauucga uaguucaaaa | 2940 |
| uggugaaauu agcaauucua caugauucag ucuaaucaau ggauaccgac uguuccccac | 3000 |
| acaagucucc uguucucuua agcuuacuca cugacagccu uucacucucc acaaauacau | 3060 |
| uaaagauaug gccaucacca agccccccuag gaugacacca gaccugagag ucugaagacc | 3120 |
| uggauccaag uucugacuuu uccccugac agcugugugu ccuucgugaa gucgccaaac | 3180 |
| cucucugagc cccagucauu gcuaguaaga ccugccuuug aguugguaug augulucaagu | 3240 |
| uagauaacaa aauguuuaua cccauuagaa cagagaauaa auagaacuac auucuugca | 3300 |

<210> SEQ ID NO 16
<211> LENGTH: 3199
<212> TYPE: RNA
<213> ORGANISM: Homo sapiens

<400> SEQUENCE: 16

| | |
|---|---|
| ugggcaggaa cugggcacug ugcccagggc augcacugcc uccacgcagc aacccucaga | 60 |
| guccugagcu gaaccaagaa ggaggagggg gucgggccuc cgaggaaggc cuagccgcug | 120 |
| cugcugccag gaauuccagg uuggaggggc ggcaaccucc ugccagccuu caggccacuc | 180 |
| uccugugcca gccagaagag acagagcuug aggagagcuu gaggagagca ggaaaggaca | 240 |
| augccgucuu cugucucgug gggcauccuc cugcuggcag gccugcugcu ccuggucccu | 300 |
| gucucccugg cugaggaucc ccagggagau gcugcccaga agacagauac aucccaccau | 360 |

```
gaucaggauc acccaaccuu caacaagauc accccccaacc uggcugaguu cgccuucagc    420
cuauaccgcc agcuggcaca ccaguccaac agcaccaaua ucuucuucuc cccagugagc    480
aucgcuacag ccuuugcaau gcucucccug gggaccaagg cugacacuca cgaugaaauc    540
cuggagggcc ugaauuucaa ccucacgag auuccggagg cucagaucca ugaaggcuuc     600
caggaacucc uccguacccu caaccagcca gacagccagc ccagcugac accggcaau     660 ggccuguuuc ucagcgaggg ccugaagcua ugggauaagu uuuggagga uguuaaaaag    720 uuguaccacu cagaagccuu cacugucaac uucggggaca ccgaagaggc caagaaacag    780
aucaacgauu acguggagaa ggguacucaa gggaaaauug uggauuuggu caaggagcuu    840
gacagagaca caguuuuugc ucuggugaau uacaucuucu uuaaaggcaa augggagaga    900
cccuuugaag ucaaggacac cgaggaagag gacuuccacg uggaccaggu gaccaccgug    960
aaggugccua ugaugaagcg uuuaggcaug uuuaacaucc agcacuguaa gaagcuguccu  1020 agcuggguc ugcugaugaa uaccuggggc aaugccaccg ccaucuucu ccugccugau   1080 gaggggaaac uacagcaccu ggaaaaugaa cucacccacg auaucaucac caaguuccug   1140
gaaaaugaag acagaagguc ugccagcuua cauuuaccca aacugccau uacuggaacc    1200 uaugaucuga agagcguccu ggucaacug gcaucacua aggucuucag caaugggcu     1260 gaccucuccg ggucacaga ggaggcaccc cugaagcucu ccaaggccgu gcauaaggcu    1320
gugcugacca ucgacgagaa agggacugaa gcugcugggg ccauguuuuu agaggccaua   1380
cccaugucua ucccccccga ggucaaguuc aacaaacccu uugucuucu aaugauugaa    1440 caaaauacca agucucccc cuucauggga aaguggguga aucccaccca aaauaacug    1500 ccucucgcuc ucaaccccu ccccuccauc ccuggcccccc uccuggaug acauuaaaga   1560 agggguugagc uggucccugc cugcauguga cuguaaaucc cucccauguu uucucugagu   1620
cucccuuugc cugcugaggc uguaugguggg uccagguaa caguacugc uucggccccc    1680 cugaacuuug uucauggagc aucggcuggg uaggcacau gcuggguug aaccagggg     1740 ggacugaauc cucagcuuac ggaccuggc ccaucuguuu cuggagggcu ccaguccuuc    1800
uuguccuguc uuggaguccc caagaaggaa ucacagggga ggaaccagau accagccaug   1860
accccaggcu ccaccaagca ucuucaugc ccccugcuca ucccccacuc ccccccaccc   1920
agauugcucu auccugccag ggcuggcugu gccccacccca aggcugcccu ccuggggcc   1980 ccagaacugc cugaucgugc cguggcccag uuuuggca ucugcagcaa cacaagagag    2040
aggacaaugu cccucuug acccgcuguc accuaaccag acucgggccc ugcaccucuc    2100 aggacuucu ggaaaaugac ugaggcagau ucuuccugaa gcccauucuc caugggcaa     2160 caaggacacc uauucugucc uugccuuccc aucgcugcc cagaaagccu cacauaucuc    2220
cguuuagaau cagguucccuu cucccagau gaagaggagg gucucugcuu uguuucucu   2280 aucuccuccu cagacuugac caggcccagc aggcccaga agaccauuac ccuauauccc    2340
uucuccuccc uagucacaug gcauaggcc ugcugauggc ucaggaagg cauugcaagg    2400 acuccuagc uaugggagag gaagcacauc acccauugac cccgcaaucc ccucccuuuc   2460
cucccucgag ucccgacugg ggccacaugc agccugacuu cuuugugccu guugcugucc   2520
cugcagucuu cagagggccca ccgcagcucc agugccacgg caggaggcug uuccugaaua  2580
gccccgugug uaagggccag gagagaccuu ccauccuccu agggcccugcu aaaggacaca  2640 gcagccagga agucccccugg gccccuagcu gaaggacagc cugcucccuc cgucucuacc  2700
```

```
aggaauggcc uguccuaug gaaggcacug ccccauccca aacuaaucua ggaaucacug      2760
ucuaaccacu cacugucaug aauguguacu uaaaggauga gguugaguca uaccaaauag      2820
ugauuucgau aguucaaaau ggugaaauua gcaauucuac augauucagu cuaaucaaug      2880
gauaccgacu guucccaca caagucuccu guucucuuaa gcuuacucac ugacagccuu      2940
ucacucucca caaauacauu aaagauaugg ccaucaccaa gcccccuagg augacaccag      3000
accugagagu cugaagaccu ggauccaagu cugacuuuu ccccugaca gcugugugac       3060 cuucgugaag ucgccaaacc ucucugagcc ccagucauug cuaguaagac cugccuuuga     3120
guugguauga guucaaguu agauaacaaa auguuuauac ccauuagaac agagaauaaa      3180
uagaacuaca uuucuugca                                                   3199

<210> SEQ ID NO 17
<211> LENGTH: 133
<212> TYPE: RNA
<213> ORGANISM: Artificial Sequence
<220> FEATURE:
<223> OTHER INFORMATION: Antisense 901

<400> SEQUENCE: 17
ccuggaggcu ugcugaaggc uguaugcugu aagcuggcag accuucuguc guuuuggcca      60
cugacugacg acagaagcug ccagcuuaca ggacacaagg ccuguuacua gcacucacau      120
ggaacaaaug gcc                                                          133

<210> SEQ ID NO 18
<211> LENGTH: 133
<212> TYPE: RNA
<213> ORGANISM: Artificial Sequence
<220> FEATURE:
<223> OTHER INFORMATION: Antisense 914

<400> SEQUENCE: 18
ccuggaggcu ugcugaaggc uguaugcuga auguaagcug gcagaccuuc guuuuggcca      60
cugacugacg aaggucucag cuuacauuca ggacacaagg ccuguuacua gcacucacau      120
ggaacaaaug gcc                                                          133

<210> SEQ ID NO 19
<211> LENGTH: 133
<212> TYPE: RNA
<213> ORGANISM: Artificial Sequence
<220> FEATURE:
<223> OTHER INFORMATION: Antisense 943

<400> SEQUENCE: 19
ccuggaggcu ugcugaaggc uguaugcuga uagguuccag uaauggacag guuuuggcca      60
cugacugacc uguccaucug gaaccuauca ggacacaagg ccuguuacua gcacucacau      120
ggaacaaaug gcc                                                          133

<210> SEQ ID NO 20
<211> LENGTH: 1254
<212> TYPE: RNA
<213> ORGANISM: Artificial Sequence
<220> FEATURE:
<223> OTHER INFORMATION: Hardened alpha-1 antitrypsin

<400> SEQUENCE: 20
augccgucuu cugucucgug gggcauccuc cugcuggcag ccugugcug ccugguccu        60 gucucccugg cugaggaucc ccagggagau gcugcccaga agacagauac aucccaccau      120
```

```
gaucaggauc acccaaccuu caacaagauc accccccaacc uggcugaguu cgccuucagc      180
cuauaccgcc agcuggcaca ccaguccaac agcaccaaua ucuucuucuc cccagugagc      240
aucgcuacag ccuuugcaau gcucucccug gggaccaagg cugacacuca cgaugaaauc      300
cuggagggcc ugaauuucaa ccucacggag auuccggagg cucagaucca ugaaggcuuc      360
caggaacucc uccguacccu caaccagcca gacagccagc ccagcugac caccggcaau       420 ggccuguucc ucagcgaggg ccugaagcua uggauaagu uuuuggagga uguuaaaaag       480
uuguaccacu cagaagccuu cacugucaac uucggggaca ccgaagaggc caagaaacag      540
aucaacgauu acguggagaa gggacucaa gggaaaauug uggauuuggu caaggagcuu       600
gacagagaca caguuuuugc ucuggugaau uacaucuucu uuaaaggcaa augggagaga      660
cccuuugaag ucaaggacac cgaggaagag gacuuccacg uggaccaggu gaccaccgug      720
aaggugccua ugaugaagcg uuuaggcaug uuuaacaucc agcacuguaa gaagcugucc      780
agcugggugc ugcugaugaa auaccugggc aaugccaccg ccaucuucuu ccugccugau      840
gaggggaaac uacagcaccu ggaaaaugaa cucacccacg auaucaucac caaguuccug      900
gaaaaugaag aucgccguag cgcuucucug caccugccca aguuaagcau caccggcacg      960
uacgaccuga agagcguccu gggucaacug gcaucacua aggucuucag caaugggcu     1020 gaccucuccg ggucacaga ggaggcaccc cugaagcucu ccaaggccgu gcauaaggcu      1080
gugcugacca ucgacgagaa agggacugaa gcugcugggg ccauguuuuu agaggccaua      1140
cccaugucua ucccccccga ggucaaguuc aacaaacccu uugucuucuu aaugauugaa      1200
caaaauacca agucucccccu cuucaugggga aaguggugga ucccacccca aaaa         1254

<210> SEQ ID NO 21
<211> LENGTH: 59
<212> TYPE: RNA
<213> ORGANISM: Artificial Sequence
<220> FEATURE:
<223> OTHER INFORMATION: miRNA 910

<400> SEQUENCE: 21
uaagcuggca gaccuucugu cguuuuggcc acugagugac gacagaagcu gccagcuua          59

<210> SEQ ID NO 22
<211> LENGTH: 59
<212> TYPE: RNA
<213> ORGANISM: Artificial Sequence
<220> FEATURE:
<223> OTHER INFORMATION: miRNA 914

<400> SEQUENCE: 22
aauguaagcu ggcagaccuu cguuuuggcc acugacugac gaaggucuca gcuuacauu          59

<210> SEQ ID NO 23
<211> LENGTH: 58
<212> TYPE: RNA
<213> ORGANISM: Artificial Sequence
<220> FEATURE:
<223> OTHER INFORMATION: miRNA 943

<400> SEQUENCE: 23
auagguucca guaauggaca gguuuggcca cugacugacc uguccaucug gaaccuau           58

<210> SEQ ID NO 24
<211> LENGTH: 7804
<212> TYPE: DNA
```

```
<213> ORGANISM: Artificial Sequence
<220> FEATURE:
<223> OTHER INFORMATION: Double 6xmiR-CB-GFP
<220> FEATURE:
<221> NAME/KEY: misc_feature
<222> LOCATION: (17)..(163)
<223> OTHER INFORMATION: inverted terminal repeats (ITR)
<220> FEATURE:
<221> NAME/KEY: enhancer
<222> LOCATION: (182)..(548)
<223> OTHER INFORMATION: Enhancer
<220> FEATURE:
<221> NAME/KEY: promoter
<222> LOCATION: (549)..(1482)
<223> OTHER INFORMATION: Chicken beta actin promoter
<220> FEATURE:
<221> NAME/KEY: Intron
<222> LOCATION: (826)..(1482)
<223> OTHER INFORMATION: intron
<220> FEATURE:
<221> NAME/KEY: misc_feature
<222> LOCATION: (1502)..(1529)
<223> OTHER INFORMATION: 5' miR
<220> FEATURE:
<221> NAME/KEY: misc_feature
<222> LOCATION: (1530)..(1550)
<223> OTHER INFORMATION: Antisense 901
<220> FEATURE:
<221> NAME/KEY: misc_signal
<222> LOCATION: (1570)..(1588)
<220> FEATURE:
<221> NAME/KEY: misc_feature
<222> LOCATION: (1593)..(1633)
<223> OTHER INFORMATION: 3' miR
<220> FEATURE:
<221> NAME/KEY: misc_feature
<222> LOCATION: (1646)..(1674)
<223> OTHER INFORMATION: 5' miR
<220> FEATURE:
<221> NAME/KEY: misc_feature
<222> LOCATION: (1675)..(1695)
<223> OTHER INFORMATION: Antisense 914
<220> FEATURE:
<221> NAME/KEY: misc_feature
<222> LOCATION: (1715)..(1733)
<223> OTHER INFORMATION: Sense delta 2
<220> FEATURE:
<221> NAME/KEY: misc_feature
<222> LOCATION: (1738)..(1778)
<223> OTHER INFORMATION: 3' miR
<220> FEATURE:
<221> NAME/KEY: misc_feature
<222> LOCATION: (1791)..(1819)
<223> OTHER INFORMATION: 5' miR
<220> FEATURE:
<221> NAME/KEY: misc_feature
<222> LOCATION: (1820)..(1840)
<223> OTHER INFORMATION: Antisense 943
<220> FEATURE:
<221> NAME/KEY: misc_feature
<222> LOCATION: (1860)..(1878)
<223> OTHER INFORMATION: Sense delta 2
<220> FEATURE:
<221> NAME/KEY: misc_feature
<222> LOCATION: (1883)..(1923)
<223> OTHER INFORMATION: 3' miR
<220> FEATURE:
<221> NAME/KEY: misc_feature
<222> LOCATION: (1936)..(2035)
<223> OTHER INFORMATION: Globin
<220> FEATURE:
<221> NAME/KEY: gene
<222> LOCATION: (2072)..(2788)
<223> OTHER INFORMATION: Green Fluorescent Protein (GFP)
<220> FEATURE:
<221> NAME/KEY: misc_feature
<222> LOCATION: (2818)..(2845)
<223> OTHER INFORMATION: 5' miR
<220> FEATURE:
```

```
<221> NAME/KEY: misc_feature
<222> LOCATION: (2846)..(2866)
<223> OTHER INFORMATION: Antisense 901
<220> FEATURE:
<221> NAME/KEY: misc_feature
<222> LOCATION: (2886)..(2904)
<223> OTHER INFORMATION: Sense delta 2
<220> FEATURE:
<221> NAME/KEY: misc_feature
<222> LOCATION: (2909)..(2949)
<223> OTHER INFORMATION: 3' miR
<220> FEATURE:
<221> NAME/KEY: misc_feature
<222> LOCATION: (2962)..(2990)
<223> OTHER INFORMATION: 5' miR
<220> FEATURE:
<221> NAME/KEY: misc_feature
<222> LOCATION: (2991)..(3011)
<223> OTHER INFORMATION: Antisense 914
<220> FEATURE:
<221> NAME/KEY: misc_feature
<222> LOCATION: (3031)..(3049)
<223> OTHER INFORMATION: sense delta 2
<220> FEATURE:
<221> NAME/KEY: misc_feature
<222> LOCATION: (3054)..(3094)
<223> OTHER INFORMATION: 3' miR
<220> FEATURE:
<221> NAME/KEY: misc_feature
<222> LOCATION: (3107)..(3135)
<223> OTHER INFORMATION: 5' miR
<220> FEATURE:
<221> NAME/KEY: misc_feature
<222> LOCATION: (3136)..(3156)
<223> OTHER INFORMATION: Antisense 943
<220> FEATURE:
<221> NAME/KEY: misc_feature
<222> LOCATION: (3176)..(3194)
<223> OTHER INFORMATION: Sense delta 2
<220> FEATURE:
<221> NAME/KEY: misc_feature
<222> LOCATION: (3199)..(3239)
<223> OTHER INFORMATION: 3' miR
<220> FEATURE:
<221> NAME/KEY: polyA_signal
<222> LOCATION: (3258)..(3470)
<223> OTHER INFORMATION: poly A tail
<220> FEATURE:
<221> NAME/KEY: promoter
<222> LOCATION: (3611)..(3739)
<223> OTHER INFORMATION: thymidine kinase promoter (Tkp)
<220> FEATURE:
<221> NAME/KEY: gene
<222> LOCATION: (3751)..(4554)
<223> OTHER INFORMATION: Neo resistance gene
<220> FEATURE:
<221> NAME/KEY: misc_feature
<222> LOCATION: (4807)..(4952)
<223> OTHER INFORMATION: Inverted terminal repeats (ITR)
<220> FEATURE:
<221> NAME/KEY: gene
<222> LOCATION: (5972)..(6832)
<223> OTHER INFORMATION: Ampicillin resistance gene

<400> SEQUENCE: 24
gggggggggg ggggggggtt ggccactccc tctctgcgcg ctcgctcgct cactgaggcc      60
gggcgaccaa aggtcgcccg acgcccgggc tttgcccggg cggcctcagt gagcgagcga     120
gcgcgcagag agggagtggc caactccatc actaggggtt cctagatctg aattcggtac     180
cctagttatt aatagtaatc aattacgggg tcattagttc atagcccata tatggagttc     240
cgcgttacat aacttacggt aaatggcccg cctggctgac cgcccaacga ccccgccca     300 ttgacgtcaa taatgacgta tgttcccata gtaacgccaa tagggacttt ccattgacgt     360
caatgggtgg actatttacg gtaaactgcc cacttggcag tacatcaagt gtatcatatg     420
```

| | | | | | |
|---|---|---|---|---|---|
| ccaagtacgc | ccctattga | cgtcaatgac | ggtaaatggc | ccgcctggca | ttatgcccag | 480 |
| tacatgacct | tatgggactt | tcctacttgg | cagtacatct | acgtattagt | catcgctatt | 540 |
| accatggtcg | aggtgagccc | cacgttctgc | ttcactctcc | ccatctcccc | ccctcccca | 600 |
| cccccaattt | tgtatttatt | tattttttaa | ttattttgtg | cagcgatggg | ggcggggggg | 660 |
| gggggggggc | gcgcgccagg | cggggcgggg | cggggcgagg | ggcggggcgg | ggcgaggcgg | 720 |
| agaggtgcgg | cggcagccaa | tcagagcggc | gcgctccgaa | agtttccttt | tatggcgagg | 780 |
| cggcggcggc | ggcggcccta | taaaaagcga | agcgcgcggc | gggcgggagt | cgctgcgacg | 840 |
| ctgccttcgc | cccgtgcccc | gctccgccgc | cgcctcgcgc | cgcccgcccc | ggctctgact | 900 |
| gaccgcgtta | ctcccacagg | tgagcgggcg | ggacggccct | tctcctccgg | gctgtaatta | 960 |
| gcgcttggtt | taatgacggc | ttgtttcttt | tctgtggctg | cgtgaaagcc | ttgaggggct | 1020 |
| ccgggagggc | cctttgtgcg | gggggagcg | gctcgggggg | tgcgtgcgtg | tgtgtgtgcg | 1080 |
| tggggagcgc | cgcgtgcggc | ccgcgctgcc | cggcggctgt | gagcgctgcg | ggcgcggcgc | 1140 |
| ggggctttgt | gcgctccgca | gtgtgcgcga | ggggagcgcg | gccggggggcg | gtgccccgcg | 1200 |
| gtgcgggggg | ggctgcgagg | ggaacaaagg | ctgcgtgcgg | ggtgtgtgcg | tgggggggtg | 1260 |
| agcaggggt | gtgggcgcgg | cggtcgggct | gtaaccccc | cctgcacccc | cctccccgag | 1320 |
| ttgctgagca | cggcccggct | tcgggtgcgg | ggctccgtac | ggggcgtggc | gcggggctcg | 1380 |
| ccgtgccggg | cgggggggtgg | cggcaggtgg | gggtgccggg | cggggcgggg | ccgcctcggg | 1440 |
| ccggggaggg | ctcgggggag | gggcgcggcg | gcccccggag | cgccggcgac | cggtgctagc | 1500 |
| cctggaggct | tgctgaaggc | tgtatgctgt | aagctggcag | accttctgtc | gttttggcca | 1560 |
| ctgactgacg | acagaagctg | ccagcttaca | ggacacaagg | cctgttacta | gcactcacat | 1620 |
| ggaacaaatg | gccaccggta | tgcatcctgg | aggcttgctg | aaggctgtat | gctgaatgta | 1680 |
| agctggcaga | ccttcgtttt | ggccactgac | tgacgaaggt | ctcagcttac | attcaggaca | 1740 |
| caaggcctgt | tactagcact | cacatggaac | aaatggccgc | tagctcgcga | cctggaggct | 1800 |
| tgctgaaggc | tgtatgctga | taggttccag | taatggacag | gttttggcca | ctgactgacc | 1860 |
| tgtccatctg | gaacctatca | ggacacaagg | cctgttacta | gcactcacat | ggaacaaatg | 1920 |
| gcctcgcgat | gcatctagag | cctctgctaa | ccatgttcat | gccttcttct | ttttcctaca | 1980 |
| gctcctgggc | aacgtgctgg | ttattgtgct | gtctcatcat | tttggcaaag | aattcctcga | 2040 |
| agatctaggc | ctgcaggcgg | ccgccgccac | catgagcaag | ggcgaggaac | tgttcactgg | 2100 |
| cgtggtccca | attctcgtgg | aactggatgg | cgatgtgaat | gggcacaaat | tttctgtcag | 2160 |
| cggagagggt | gaaggtgatg | ccacatacgg | aaagctcacc | ctgaaattca | tctgcaccac | 2220 |
| tggaaagctc | cctgtgccat | ggccaacact | ggtcactacc | ctgacctatg | gcgtgcagtg | 2280 |
| cttttccaga | tacccagacc | atatgaagca | gcatgacttt | ttcaagagcg | ccatgcccga | 2340 |
| gggctatgtg | caggagagaa | ccatcttttt | caaagatgac | gggaactaca | agacccgcgc | 2400 |
| tgaagtcaag | ttcgaaggtg | acaccctggt | gaatagaatc | gagctgaagg | gcattgactt | 2460 |
| taaggaggat | ggaaacattc | tcggccacaa | gctggaatac | aactataact | cccacaatgt | 2520 |
| gtacatcatg | gccgacaagc | aaaagaatgg | catcaaggtc | aacttcaaga | tcagacacaa | 2580 |
| cattgaggat | ggatccgtgc | agctggccga | ccattatcaa | cagaacactc | caatcggcga | 2640 |
| cggccctgtg | ctcctcccag | acaaccatta | cctgtccacc | cagtctgccc | tgtctaaaga | 2700 |
| tcccaacgaa | aagagagacc | acatggtcct | gctggagttt | gtgaccgctg | ctgggatcac | 2760 |

```
acatggcatg gacgagctgt acaagtgacc tgcaggcgcc ggcgaccggt gctagccctg    2820
gaggcttgct gaaggctgta tgctgtaagc tggcagacct tctgtcgttt tggccactga    2880
ctgacgacag aagctgccag cttacaggac acaaggcctg ttactagcac tcacatggaa    2940
caaatggcca ccggtatgca tcctggaggc ttgctgaagg ctgtatgctg aatgtaagct    3000
ggcagacctt cgttttggcc actgactgac gaaggtctca gcttacattc aggacacaag    3060
gcctgttact agcactcaca tggaacaaat ggccgctagc tcgcgacctg gaggcttgct    3120
gaaggctgta tgctgatagg ttccagtaat ggacaggttt tggccactga ctgacctgtc    3180
catctggaac ctatcaggac acaaggcctg ttactagcac tcacatggaa caaatggcct    3240
cgcgatgcat ctagagcggc cgcggggatc cagacatgat aagatacatt gatgagtttg    3300
gacaaaccac aactagaatg cagtgaaaaa aatgctttat ttgtgaaatt tgtgatgcta    3360
ttgctttatt tgtaaccatt ataagctgca ataaacaagt taacaacaac aattgcattc    3420
attttatgtt tcaggttcag ggggaggtgt gggaggtttt ttagtcgacc tcgagcagtg    3480
tggttttgca agaggaagca aaaagcctct ccacccaggc ctggaatgtt ccacccaag    3540 tcgaaggcag tgtggttttg caagaggaag caaaaagcct ctccacccag gcctggaatg    3600
tttccaccca atgtcgagca ccccgcccca gcgtcttgtc attggcgaat cgaacacgc    3660 agatgcagtc ggggcggcgc ggtcccaggt ccacttcgca tattaaggtg acgcgtgtgg    3720
cctcgaacac cgagcgaccc tgcagccaat atgggatcgg ccattgaaca agatggattg    3780
cacgcaggtt ctccggccgc ttgggtggag aggctattcg gctatgactg gcacaacag    3840 acaatcggct gctctgatgc cgccgtgttc cggctgtcag cgcaggggcg cccggttctt    3900
tttgtcaaga ccgacctgtc cggtgccctg aatgaactgc aggacgaggc agcgcggcta    3960
tcgtggctgg ccacgacggg cgttccttgc gcagctgtgc tcgacgttgt cactgaagcg    4020
ggaagggact ggctgctatt gggcgaagtg ccggggcagg atctcctgtc atctcacctt    4080
gctcctgccg agaaagtatc catcatggct gatgcaatgc ggcggctgca tacgcttgat    4140
ccggctacct gcccattcga ccaccaagcg aaacatcgca tcgagcgagc acgtactcgg    4200
atggaagccg gtcttgtcga tcaggatgat ctggacgaag agcatcaggg gctcgcgcca    4260
gccgaactgt tcgccaggct caaggcgcgc atgcccgacg gcgaggatct cgtcgtgacc    4320
catggcgatg cctgcttgcc gaatatcatg gtggaaaatg gccgcttttc tggattcatc    4380
gactgtggcc ggctgggtgt ggcggaccgc tatcaggaca tagcgttggc tacccgtgat    4440
attgctgaag agcttggcgg cgaatgggct gaccgcttcc tcgtgcttta cggtatcgcc    4500
gctcccgatt cgcagcgcat cgccttctat cgccttcttg acgagttctt ctgagggat    4560 ccgtcgacta gagctcgctg atcagcctcg actgtgcctt ctagttgcca gccatctgtt    4620
gtttgcccct cccccgtgcc ttccttgacc ctggaaggtg ccactcccac tgtcctttcc    4680
taataaaatg aggaaattgc atcgcattgt ctgagtaggt gtcattctat tctgggggt    4740 ggggtggggc aggacagcaa gggggaggat tgggaagaca atagcaggca tgctgggag    4800 agatctagga acccctagtg atggagttgg ccactccctc tctgcgcgct cgctcgctca    4860
ctgaggccgc ccgggcaaag cccgggcgtc gggcgacctt tggtcgcccg gcctcagtga    4920
gcgagcgagc gcgcagagag ggagtggcca accccccccc ccccccccct gcagccctgc    4980
attaatgaat cggccaacgc gcggggagag gcggtttgcg tattgggcgc tcttccgctt    5040
cctcgctcac tgactcgctg cgctcggtcg ttcggctgcg gcgagcggta tcagctcact    5100
caaaggcggt aatacggtta tccacagaat caggggataa cgcaggaaag aacatgtgag    5160
```

```
caaaaggcca gcaaaaggcc aggaaccgta aaaaggccgc gttgctggcg ttttccata    5220 ggctccgccc ccctgacgag catcacaaaa atcgacgctc aagtcagagg tggcgaaacc   5280
cgacaggact ataaagatac caggcgtttc ccctggaag ctccctcgtg cgctctcctg    5340
ttccgaccct gccgcttacc ggatacctgt ccgcctttct ccttcggga agcgtggcgc    5400 tttctcaatg ctcacgctgt aggtatctca gttcggtgta ggtcgttcgc tccaagctgg   5460
gctgtgtgca cgaaccccc gttcagcccg accgctgcgc cttatccggt aactatcgtc    5520
ttgagtccaa cccggtaaga cacgacttat cgccactggc agcagccact ggtaacagga   5580
ttagcagagc gaggtatgta ggcggtgcta cagagttctt gaagtggtgg cctaactacg   5640
gctacactag aaggacagta tttggtatct gcgctctgct gaagccagtt accttcggaa   5700
aaagagttgg tagctcttga tccggcaaac aaaccaccgc tggtagcggt ggttttttg    5760 tttgcaagca gcagattacg cgcagaaaaa aaggatctca agaagatcct tgatctttt    5820 ctacggggtc tgacgctcag tggaacgaaa actcacgtta agggattttg gtcatgagat   5880
tatcaaaaag gatcttcacc tagatccttt taaattaaaa atgaagtttt aaatcaatct   5940
aaagtatata tgagtaaact tggtctgaca gttaccaatg cttaatcagt gaggcaccta   6000
tctcagcgat ctgtctattt cgttcatcca tagttgcctg actccccgtc gtgtagataa   6060
ctacgatacg ggagggctta ccatctggcc ccagtgctgc aatgataccg cgagacccac   6120
gctcaccggc tccagattta tcagcaataa accagccagc cggaagggcc gagcgcagaa   6180
gtggtcctgc aactttatcc gcctccatcc agtctattaa ttgttgccgg gaagctagag   6240
taagtagttc gccagttaat agtttgcgca acgttgttgc cattgctaca ggcatcgtgg   6300
tgtcacgctc gtcgtttggt atggcttcat tcagctccgg ttcccaacga tcaaggcgag   6360
ttacatgatc ccccatgttg tgcaaaaaag cggttagctc cttcggtcct ccgatcgttg   6420
tcagaagtaa gttggccgca gtgttatcac tcatggttat ggcagcactg cataattctc   6480
ttactgtcat gccatccgta agatgctttt ctgtgactgg tgagtactca accaagtcat   6540
tctgagaata gtgtatgcgg cgaccgagtt gctcttgccc ggcgtcaata cgggataata   6600
ccgcgccaca tagcagaact ttaaaagtgc tcatcattgg aaaacgttct cgggggcgaa   6660
aactctcaag gatcttaccg ctgttgagat ccagttcgat gtaacccact cgtgcaccca   6720
actgatcttc agcatctttt actttcacca gcgtttctgg gtgagcaaaa acaggaaggc   6780
aaaatgccgc aaaaaaggga ataagggcga cacggaaatg ttgaatactc atactcttcc   6840
tttttcaata ttattgaagc atttatcagg gttattgtct catgagcgga tacatatttg   6900
aatgtattta gaaaaataaa caaatagggg ttccgcgcac atttccccga aaagtgccac   6960
ctgacgtcta agaaaccatt attatcatga cattaaccta taaaaatagg cgtatcacga   7020
ggccctttcg tctcgcgcgt ttcggtgatg acggtgaaaa cctctgacac atgcagctcc   7080
cggagacggt cacagcttgt ctgtaagcgg atgccgggag cagacaagcc cgtcagggcg   7140
cgtcagcggg tgttggcggg tgtcggggct ggcttaacta tgcggcatca gagcagattg   7200
tactgagagt gcaccatatg cggtgtgaaa taccgcacag atgcgtaagg agaaaatacc   7260
gcatcaggaa attgtaaacg ttaatatttt gttaaaattc gcgttaaatt tttgttaaat   7320
cagctcattt tttaaccaat aggccgaaat cggcaaaatc ccttataaat caaaagaata   7380
gaccgagata gggttgagtg ttgttccagt ttggaacaag agtccactat taagaacgt    7440 ggactccaac gtcaaagggc gaaaaaccgt ctatcagggc gatggcccac tacgtgaacc   7500
```

```
atcaccctaa tcaagtttttt tggggtcgag gtgccgtaaa gcactaaatc ggaaccctaa    7560
agggagcccc cgatttagag cttgacgggg aaagccggcg aacgtggcga gaaaggaagg    7620
gaagaaagcg aaaggagcgg gcgctagggc gctggcaagt gtagcggtca cgctgcgcgt    7680
aaccaccaca cccgccgcgc ttaatgcgcc gctacagggc gcgtcgcgcc attcgccatt    7740
caggctacgc aactgttggg aagggcgatc ggtgcgggcc tcttcgctat tacgccaggc    7800
tgca                                                                  7804
```

```
<210> SEQ ID NO 25
<211> LENGTH: 7667
<212> TYPE: DNA
<213> ORGANISM: Artificial Sequence
<220> FEATURE:
<223> OTHER INFORMATION: PolyA-3XmiR-CB-GFP
<220> FEATURE:
<221> NAME/KEY: misc_feature
<222> LOCATION: (17)..(163)
<223> OTHER INFORMATION: Inverted terminal repeats (ITR)
<220> FEATURE:
<221> NAME/KEY: enhancer
<222> LOCATION: (182)..(548)
<223> OTHER INFORMATION: Enhancer
<220> FEATURE:
<221> NAME/KEY: promoter
<222> LOCATION: (549)..(1795)
<223> OTHER INFORMATION: Chicken beta actin promoter
<220> FEATURE:
<221> NAME/KEY: Intron
<222> LOCATION: (826)..(1795)
<223> OTHER INFORMATION: Intron
<220> FEATURE:
<221> NAME/KEY: misc_feature
<222> LOCATION: (1796)..(1898)
<223> OTHER INFORMATION: Globin
<220> FEATURE:
<221> NAME/KEY: gene
<222> LOCATION: (1935)..(2651)
<223> OTHER INFORMATION: Green fluorescent protein (GFP)
<220> FEATURE:
<221> NAME/KEY: misc_feature
<222> LOCATION: (2681)..(2708)
<223> OTHER INFORMATION: 5' miR
<220> FEATURE:
<221> NAME/KEY: misc_feature
<222> LOCATION: (2709)..(2729)
<223> OTHER INFORMATION: Antisense 901
<220> FEATURE:
<221> NAME/KEY: misc_feature
<222> LOCATION: (2749)..(2767)
<223> OTHER INFORMATION: Sense delta 2
<220> FEATURE:
<221> NAME/KEY: misc_feature
<222> LOCATION: (2772)..(2812)
<223> OTHER INFORMATION: 3' miR
<220> FEATURE:
<221> NAME/KEY: misc_feature
<222> LOCATION: (2854)..(2874)
<223> OTHER INFORMATION: Antisense 914
<220> FEATURE:
<221> NAME/KEY: misc_feature
<222> LOCATION: (2894)..(2912)
<223> OTHER INFORMATION: Sense delta 2
<220> FEATURE:
<221> NAME/KEY: misc_feature
<222> LOCATION: (2917)..(2957)
<223> OTHER INFORMATION: 3' miR
<220> FEATURE:
<221> NAME/KEY: misc_feature
<222> LOCATION: (2970)..(2998)
<223> OTHER INFORMATION: 5' miR
<220> FEATURE:
<221> NAME/KEY: misc_feature
<222> LOCATION: (2999)..(3019)
<223> OTHER INFORMATION: Antisense 943
```

```
<220> FEATURE:
<221> NAME/KEY: misc_feature
<222> LOCATION: (3039)..(3057)
<223> OTHER INFORMATION: Sense delta 2
<220> FEATURE:
<221> NAME/KEY: misc_feature
<222> LOCATION: (3062)..(3102)
<223> OTHER INFORMATION: 3' miR
<220> FEATURE:
<221> NAME/KEY: polyA_signal
<222> LOCATION: (3121)..(3333)
<223> OTHER INFORMATION: polyA tail
<220> FEATURE:
<221> NAME/KEY: promoter
<222> LOCATION: (3474)..(3602)
<223> OTHER INFORMATION: thymidine kinase promoter (Tkp)
<220> FEATURE:
<221> NAME/KEY: gene
<222> LOCATION: (3614)..(4417)
<223> OTHER INFORMATION: Neomycin resistance gene
<220> FEATURE:
<221> NAME/KEY: misc_feature
<222> LOCATION: (4670)..(4815)
<223> OTHER INFORMATION: inverted terminal repeats (ITR)
<220> FEATURE:
<221> NAME/KEY: gene
<222> LOCATION: (5835)..(6695)
<223> OTHER INFORMATION: Ampicillin resistance gene

<400> SEQUENCE: 25
gggggggggg ggggggggtt ggccactccc tctctgcgcg ctcgctcgct cactgaggcc      60
gggcgaccaa aggtcgcccg acgcccgggc tttgcccggg cggcctcagt gagcgagcga     120
gcgcgcagag agggagtggc caactccatc actaggggtt cctagatctg aattcggtac     180
cctagttatt aatagtaatc aattacgggg tcattagttc atagcccata tatggagttc     240
cgcgttacat aacttacggt aaatggcccg cctggctgac cgcccaacga ccccccgccca    300
ttgacgtcaa taatgacgta tgttcccata gtaacgccaa tagggacttt ccattgacgt     360
caatgggtgg actatttacg gtaaactgcc cacttggcag tacatcaagt gtatcatatg     420
ccaagtacgc cccctattga cgtcaatgac ggtaaatggc ccgcctggca ttatgcccag     480
tacatgacct tatgggactt tcctacttgg cagtacatct acgtattagt catcgctatt     540
accatggtcg aggtgagccc cacgttctgc ttcactctcc ccatctcccc ccctccccca     600
cccccaattt tgtatttatt tattttttaa ttattttgtg cagcgatggg ggcggggggg     660
ggggggggggc gcgcgccagg cggggcgggg cgggcgagg ggcggggcgg ggcgaggcgg     720
agaggtgcgg cggcagccaa tcagagcggc gcgctccgaa agtttccttt tatggcgagg     780
cggcggcggc ggcggcccta taaaaagcga agcgcgcggc gggcgggagt cgctgcgacg     840
ctgccttcgc cccgtgcccc gctccgccgc cgcctcgcgc cgcccgcccc ggctctgact     900
gaccgcgtta ctcccacagg tgagcgggcg ggacggccct tctcctccgg gctgtaatta     960
gcgcttggtt taatgacggc ttgtttcttt tctgtggctg cgtgaaagcc ttgaggggct    1020
ccggagggc cctttgtgcg ggggagcg gctcggggg tgcgtgcgtg tgtgtgtgcg        1080
tggggagcgc cgcgtgcggc ccgcgctgcc cggcggctgt gagcgctgcg ggcgcggcgc    1140
ggggctttgt gcgctccgca gtgtgcgcga ggggagcgcg gccggggcg gtgccccgcg     1200
gtgcggggggg ggctgcgagg ggaacaaagg ctgcgtgcgg ggtgtgtgcg tggggggtg    1260
agcaggggt gtgggcgcgg cggtcgggct gtaaccccccc cctgcaccccc cctccccgag   1320
ttgctgagca cggcccggct tcgggtgcgg ggctccgtac ggggcgtggc gcggggctcg    1380
ccgtgccggg cgggggtgg cggcaggtgg gggtgccggg cggggcgggg ccgcctcggg     1440
```

```
ccggggaggg ctcggggag gggcgcggcg gccccggag cgccggcggc tgtcgaggcg    1500
cggcgagccg cagccattgc cttttatggt aatcgtgcga gagggcgcag ggacttcctt    1560
tgtcccaaat ctgtgcggag ccgaaatctg ggaggcgccg ccgcaccccc tctagcgggc    1620
gcggggcgaa gcggtgcggc gccggcagga aggaaatggg cggggagggc cttcgtgcgt    1680
cgccgcgccg ccgtccccctt ctccctctcc agcctcgggg ctgtccgcgg ggggacggct    1740
gccttcgggg gggacgggc agggcgggt tcggcttctg cgtgtgacc ggcggctcta    1800 gagcctctgc taaccatgtt catgccttct tcttttcct acagctcctg ggcaacgtgc    1860
tggttattgt gctgtctcat cattttggca aagaattcct cgaagatcta ggcctgcagg    1920
cggccgccgc caccatgagc aagggcgagg aactgttcac tggcgtggtc ccaattctcg    1980
tggaactgga tggcgatgtg aatgggcaca atttttctgt cagcggagag ggtgaaggtg    2040
atgccacata cggaaagctc accctgaaat tcatctgcac cactggaaag ctccctgtgc    2100
catggccaac actggtcact accctgacct atggcgtgca gtgcttttcc agatacccag    2160
accatatgaa gcagcatgac tttttcaaga gcgccatgcc cgagggctat gtgcaggaga    2220
gaaccatctt tttcaaagat gacgggaact acaagacccg cgctgaagtc aagttcgaag    2280
gtgacaccct ggtgaataga atcgagctga agggcattga cttttaaggag gatggaaaca    2340 ttctcggcca caagctggaa tacaactata actcccacaa tgtgtacatc atggccgaca    2400
agcaaaagaa tggcatcaag gtcaacttca agatcagaca caacattgag gatggatccg    2460
tgcagctggc cgaccattat caacagaaca ctccaatcgg cgacggccct gtgctcctcc    2520
cagacaacca ttacctgtcc acccagtctg ccctgtctaa agatcccaac gaaaagagag    2580
accacatggt cctgctggag tttgtgaccg ctgctgggat cacacatggc atggacgagc    2640
tgtacaagtg acctgcaggc gccggcgacc ggtgctagcc ctggaggctt gctgaaggct    2700
gtatgctgta agctggcaga ccttctgtcg ttttggccac tgactgacga cagaagctgc    2760
cagcttacag gacacaaggc ctgttactag cactcacatg gaacaaatgg ccaccggtat    2820
gcatcctgga ggcttgctga aggctgtatg ctgaatgtaa gctggcagac cttcgttttg    2880
gccactgact gacgaaggtc tcagcttaca ttcaggacac aaggcctgtt actagcactc    2940
acatggaaca aatggccgct agctcgcgac ctggaggctt gctgaaggct gtatgctgat    3000
aggttccagt aatggacagg ttttggccac tgactgacct gtccatctgg aacctatcag    3060
gacacaaggc ctgttactag cactcacatg gaacaaatgg cctcgcgatg catctagagc    3120
ggccgcgggg atccagacat gataagatac attgatgagt ttggacaaac cacaactaga    3180
atgcagtgaa aaaatgcttt tatttgtgaa atttgtgatg ctattgcttt atttgtaacc    3240
attataagct gcaataaaca agttaacaac aacaattgca ttcatttat gtttcaggtt    3300 cagggggagg tgtgggaggt tttttagtcg acctcgagca gtgtggtttt gcaagaggaa    3360
gcaaaaagcc tctccaccca ggcctggaat gtttccaccc aagtcgaagg cagtgtggtt    3420
ttgcaagagg aagcaaaaag cctctccacc caggcctgga atgtttccac ccaatgtcga    3480
gcaaccccgc ccagcgtctt gtcattggcg aattcgaaca cgcagatgca gtcggggcgg    3540
cgcggtccca ggtccacttc gcatattaag gtgacgcgtg tggcctcgaa caccgagcga    3600
ccctgcagcc aatatgggat cggccattga acaagatgga ttgcacgcag ttctccggc    3660 cgcttgggtg gagaggctat tcggctatga ctgggcacaa cagacaatcg gctgctctga    3720
tgccgccgtg ttccggctgt cagcgcaggg gcgcccggtt cttttgtca agaccgacct    3780 gtccggtgcc ctgaatgaac tgcaggacga ggcagcgcgg ctatcgtggc tggccacgac    3840
```

```
gggcgttcct tgcgcagctg tgctcgacgt tgtcactgaa gcgggaaggg actggctgct   3900
attgggcgaa gtgccggggc aggatctcct gtcatctcac cttgctcctg ccagaaaagt   3960
atccatcatg gctgatgcaa tgcggcggct gcatacgctt gatccggcta cctgcccatt   4020
cgaccaccaa gcgaaacatc gcatcgagcg agcacgtact cggatggaag ccggtcttgt   4080
cgatcaggat gatctggacg aagagcatca ggggctcgcg ccagccgaac tgttcgccag   4140
gctcaaggcg cgcatgcccg acggcgagga tctcgtcgtg acccatggcg atgcctgctt   4200
gccgaatatc atggtggaaa atggccgctt ttctggattc atcgactgtg gccggctggg   4260
tgtggcggac cgctatcagg acatagcgtt ggctacccgt gatattgctg aagagcttgg   4320
cggcgaatgg gctgaccgct tcctcgtgct ttacggtatc gccgctcccg attcgcagcg   4380
catcgccttc tatcgccttc ttgacgagtt cttctgaggg gatccgtcga ctagagctcg   4440
ctgatcagcc tcgactgtgc cttctagttg ccagccatct gttgtttgcc cctcccccgt   4500
gccttccttg accctggaag gtgccactcc cactgtcctt tcctaataaa atgaggaaat   4560
tgcatcgcat tgtctgagta ggtgtcattc tattctgggg ggtgggtgg ggcaggacag     4620
caaggggag gattggaag acaatagcag gcatgctggg gagagatcta ggaaccccta      4680
gtgatggagt tggccactcc ctctctgcgc gctcgctcgc tcactgaggc cgcccgggca   4740
aagcccgggc gtcgggcgac cttggtcgc ccggcctcag tgagcgagcg agcgcgcaga    4800
gagggagtgg ccaaccccccc cccccccccc cctgcagccc tgcattaatg aatcggccaa   4860
cgcgcgggga gaggcggttt gcgtattggg cgctcttccg cttcctcgct cactgactcg   4920
ctgcgctcgg tcgttcggct gcggcgagcg gtatcagctc actcaaaggc ggtaatacgg   4980
ttatccacag aatcagggga taacgcagga aagaacatgt gagcaaaagg ccagcaaaag   5040
gccaggaacc gtaaaaaggc cgcgttgctg gcgttttcc ataggctccg ccccctgac     5100
gagcatcaca aaaatcgacg ctcaagtcag aggtggcgaa acccgacagg actataaaga   5160
taccaggcgt ttccccctgg aagctccctc gtgcgctctc ctgttccgac cctgccgctt   5220
accggatacc tgtccgcctt tctcccttcg ggaagcgtgg cgctttctca atgctcacgc   5280
tgtaggtatc tcagttcggt gtaggtcgtt cgctccaagc tgggctgtgt gcacgaaccc   5340
cccgttcagc ccgaccgctg cgccttatcc ggtaactatc gtcttgagtc aacccggta    5400
agacacgact tatcgccact ggcagcagcc actggtaaca ggattagcag agcgaggtat   5460
gtaggcggtg ctacagagtt cttgaagtgg tggcctaact acggctacac tagaaggaca   5520
gtatttggta tctgcgctct gctgaagcca gttaccttcg gaaaaagagt ggtagctct    5580
tgatccggca aacaaaccac cgctggtagc ggtggttttt tgtttgcaa gcagcagatt    5640
acgcgcagaa aaaaggatc tcaagaagat cctttgatct tttctacggg gtctgacgct   5700
cagtggaacg aaaactcacg ttaagggatt ttggtcatga gattatcaaa aaggatcttc   5760
acctagatcc ttttaaatta aaaatgaagt tttaaatcaa tctaaagtat atatgagtaa   5820
acttggtctg acagttacca atgcttaatc agtgaggcac ctatctcagc gatctgtcta   5880
tttcgttcat ccatagttgc ctgactcccc gtcgtgtaga taactacgat acgggagggc   5940
ttaccatctg gccccagtgc tgcaatgata ccgcgagacc cacgctcacc ggctccagat   6000
ttatcagcaa taaaccagcc agccggaagg gccgagcgca gaagtggtcc tgcaacttta   6060
tccgcctcca tccagtctat taattgttgc cgggaagcta gagtaagtag ttcgccagtt   6120
aatagtttgc gcaacgttgt tgccattgct acaggcatcg tggtgtcacg ctcgtcgttt   6180
```

```
ggtatggctt cattcagctc cggttcccaa cgatcaaggc gagttacatg atcccccatg    6240
ttgtgcaaaa aagcggttag ctccttcggt cctccgatcg ttgtcagaag taagttggcc    6300
gcagtgttat cactcatggt tatggcagca ctgcataatt ctcttactgt catgccatcc    6360
gtaagatgct tttctgtgac tggtgagtac tcaaccaagt cattctgaga atagtgtatg    6420
cggcgaccga gttgctcttg cccggcgtca atacgggata ataccgcgcc acatagcaga    6480
actttaaaag tgctcatcat tggaaaacgt tcttcgggc gaaaactctc aaggatctta    6540
ccgctgttga gatccagttc gatgtaaccc actcgtgcac ccaactgatc ttcagcatct    6600
tttactttca ccagcgtttc tgggtgagca aaaacaggaa ggcaaaatgc cgcaaaaaag    6660
ggaataaggg cgacacggaa atgttgaata ctcatactct tcctttttca atattattga    6720
agcatttatc agggttattg tctcatgagc ggatacatat ttgaatgtat ttagaaaaat    6780
aaacaaatag gggttccgcg cacatttccc cgaaaagtgc cacctgacgt ctaagaaacc    6840
attattatca tgacattaac ctataaaaat aggcgtatca cgaggccctt tcgtctcgcg    6900
cgtttcggtg atgacggtga aaacctctga cacatgcagc tcccggagac ggtcacagct    6960
tgtctgtaag cggatgccgg gagcagacaa gcccgtcagg gcgcgtcagc gggtgttggc    7020
gggtgtcggg gctggcttaa ctatgcggca tcagagcaga ttgtactgag agtgcaccat    7080
atgcggtgtg aaataccgca cagatgcgta aggagaaaat accgcatcag gaaattgtaa    7140
acgttaatat tttgttaaaa ttcgcgttaa attttttgtta aatcagctca ttttttaacc    7200
aataggccga atcggcaaa atcccttata aatcaaaaga atagaccgag atagggttga    7260
gtgttgttcc agtttggaac aagagtccac tattaaagaa cgtggactcc aacgtcaaag    7320
ggcgaaaaac cgtctatcag ggcgatggcc cactacgtga accatcaccc taatcaagtt    7380
ttttggggtc gaggtgccgt aaagcactaa atcggaaccc taagggagc ccccgattta    7440 gagcttgacg gggaaagccg gcgaacgtgg cgagaaagga agggaagaaa gcgaaggag    7500 cgggcgctag ggcgctggca agtgtagcgg tcacgctgcg cgtaaccacc acccgccg    7560 cgcttaatgc gccgctacag ggcgcgtcgc gccattcgcc attcaggcta cgcaactgtt    7620
gggaagggcg atcggtgcgg gcctcttcgc tattacgcca ggctgca               7667
```

```
<210> SEQ ID NO 26
<211> LENGTH: 7337
<212> TYPE: DNA
<213> ORGANISM: Artificial Sequence
<220> FEATURE:
<223> OTHER INFORMATION: Intronic-3XmiR-CB-GFP
<220> FEATURE:
<221> NAME/KEY: misc_feature
<222> LOCATION: (17)..(163)
<223> OTHER INFORMATION: Inverted terminal repeats (ITR)
<220> FEATURE:
<221> NAME/KEY: enhancer
<222> LOCATION: (182)..(548)
<223> OTHER INFORMATION: enhancer
<220> FEATURE:
<221> NAME/KEY: promoter
<222> LOCATION: (549)..(1482)
<223> OTHER INFORMATION: Chicken beta actin promoter
<220> FEATURE:
<221> NAME/KEY: Intron
<222> LOCATION: (826)..(1482)
<223> OTHER INFORMATION: Chicken beta actin intron
<220> FEATURE:
<221> NAME/KEY: misc_feature
<222> LOCATION: (1502)..(1529)
<223> OTHER INFORMATION: 5' miR
<220> FEATURE:
<221> NAME/KEY: misc_feature
```

```
<222> LOCATION: (1530)..(1550)
<223> OTHER INFORMATION: Antisense 901
<220> FEATURE:
<221> NAME/KEY: misc_feature
<222> LOCATION: (1570)..(1588)
<223> OTHER INFORMATION: Sense delta 2
<220> FEATURE:
<221> NAME/KEY: misc_feature
<222> LOCATION: (1593)..(1633)
<223> OTHER INFORMATION: 3' miR
<220> FEATURE:
<221> NAME/KEY: misc_feature
<222> LOCATION: (1646)..(1674)
<223> OTHER INFORMATION: 5' miR
<220> FEATURE:
<221> NAME/KEY: misc_feature
<222> LOCATION: (1675)..(1695)
<223> OTHER INFORMATION: Antisense 914
<220> FEATURE:
<221> NAME/KEY: misc_feature
<222> LOCATION: (1715)..(1733)
<223> OTHER INFORMATION: Sense delta 2
<220> FEATURE:
<221> NAME/KEY: misc_feature
<222> LOCATION: (1738)..(1778)
<223> OTHER INFORMATION: 3' miR
<220> FEATURE:
<221> NAME/KEY: misc_feature
<222> LOCATION: (1791)..(1819)
<223> OTHER INFORMATION: 5' miR
<220> FEATURE:
<221> NAME/KEY: misc_feature
<222> LOCATION: (1820)..(1840)
<223> OTHER INFORMATION: Antisense 943
<220> FEATURE:
<221> NAME/KEY: misc_feature
<222> LOCATION: (1860)..(1878)
<223> OTHER INFORMATION: Sense delta 2
<220> FEATURE:
<221> NAME/KEY: misc_feature
<222> LOCATION: (1883)..(1923)
<223> OTHER INFORMATION: 3' miR
<220> FEATURE:
<221> NAME/KEY: gene
<222> LOCATION: (2072)..(2788)
<223> OTHER INFORMATION: GFP
<220> FEATURE:
<221> NAME/KEY: polyA_signal
<222> LOCATION: (2789)..(3003)
<223> OTHER INFORMATION: polyA tail
<220> FEATURE:
<221> NAME/KEY: promoter
<222> LOCATION: (3144)..(3272)
<223> OTHER INFORMATION: thymidine kinase promoter (Tkp)
<220> FEATURE:
<221> NAME/KEY: gene
<222> LOCATION: (3284)..(4087)
<223> OTHER INFORMATION: Neomycin resistance gene
<220> FEATURE:
<221> NAME/KEY: misc_feature
<222> LOCATION: (4340)..(4485)
<223> OTHER INFORMATION: Inverted terminal repeats (ITR)
<220> FEATURE:
<221> NAME/KEY: gene
<222> LOCATION: (5505)..(6365)
<223> OTHER INFORMATION: Ampicillin (complement)

<400> SEQUENCE: 26
gggggggggg ggggggggtt ggccactccc tctctgcgcg ctcgctcgct cactgaggcc      60
gggcgaccaa aggtcgcccg acgcccgggc tttgcccggg cggcctcagt gagcgagcga     120
gcgcgcagag agggagtggc caactccatc actagggggtt cctagatctg aattcggtac   180
cctagttatt aatagtaatc aattacgggg tcattagttc atagcccata tatggagttc   240
cgcgttacat aacttacggt aaatggcccg cctggctgac cgcccaacga ccccccgccca  300
```

```
ttgacgtcaa taatgacgta tgttcccata gtaacgccaa tagggacttt ccattgacgt    360
caatgggtgg actatttacg gtaaactgcc cacttggcag tacatcaagt gtatcatatg    420
ccaagtacgc cccctattga cgtcaatgac ggtaaatggc ccgcctggca ttatgcccag    480
tacatgacct tatgggactt tcctacttgg cagtacatct acgtattagt catcgctatt    540
accatggtcg aggtgagccc cacgttctgc ttcactctcc ccatctcccc ccctcccca    600
cccccaattt tgtatttatt tattttttaa ttattttgtg cagcgatggg ggcggggggg    660
ggggggggc gcgcgccagg cggggcgggg cggggcgagg ggcggggcgg ggcgaggcgg    720
agaggtgcgg cggcagccaa tcagagcggc gcgctccgaa agtttccttt tatggcgagg    780
cggcggcggc ggcggcccta taaaaagcga agcgcgcggc gggcgggagt cgctgcgacg    840
ctgccttcgc cccgtgcccc gctccgccgc cgcctcgcgc cgcccgcccc ggctctgact    900
gaccgcgtta ctcccacagg tgagcgggcg ggacggccct tctcctccgg gctgtaatta    960
gcgcttggtt taatgacggc ttgtttcttt tctgtggctg cgtgaaagcc ttgagggggct   1020
ccgggaggggc cctttgtgcg ggggagcg gctcgggggg tgcgtgcgtg tgtgtgtgcg    1080
tgggagcgc cgcgtgcggc ccgcgctgcc cggcggctgt gagcgctgcg ggcgcggcgc    1140
ggggctttgt gcgctccgca gtgtgcgcga ggggagcgcg gccggggcg gtgccccgcg    1200
gtgcggggg ggctgcgagg ggaacaaagg ctgcgtgcgg ggtgtgtgcg tgggggggtg    1260
agcagggggt gtgggcgcgg cggtcgggct gtaaccccc cctgcacccc cctcccgag    1320
ttgctgagca cggcccggct tcgggtgcgg ggctccgtac ggggcgtggc gcggggctcg    1380
ccgtgccggg cggggggtgg cggcaggtgg gggtgccggg cggggcgggg ccgcctcggg    1440
ccggggaggg ctcggggag gggcgcggcg gccccggag cgccggcgac cggtgctagc    1500
cctggaggct tgctgaaggc tgtatgctgt aagctggcag accttctgtc gttttggcca    1560
ctgactgacg acagaagctg ccagcttaca ggacacaagg cctgttacta gcactcacat    1620
ggaacaaatg gccaccggta tgcatcctgg aggcttgctg aaggctgtat gctgaatgta    1680
agctggcaga ccttcgtttt ggccactgac tgacgaaggt ctcagcttac attcaggaca    1740
caaggcctgt tactagcact cacatggaac aaatggccgc tagctcgcga cctggaggct    1800
tgctgaaggc tgtatgctga taggttccag taatggacag gttttggcca ctgactgacc    1860
tgtccatctg gaacctatca ggacacaagg cctgttacta gcactcacat ggaacaaatg    1920
gcctcgcgat gcatctagag cctctgctaa ccatgttcat gccttcttct ttttcctaca    1980
gctcctgggc aacgtgctgg ttattgtgct gtctcatcat tttggcaaag aattcctcga    2040
agatctaggc ctgcaggcgg ccgccgccac catgagcaag ggcgaggaac tgttcactgg    2100
cgtggtccca attctcgtgg aactggatgg cgatgtgaat gggcacaaat tttctgtcag    2160
cggagagggt gaaggtgatg ccacatacgg aaagctcacc ctgaaattca tctgcaccac    2220
tggaaagctc cctgtgccat ggccaacact ggtcactacc ctgacctatg gcgtgcagtg    2280
cttttccaga tacccagacc atatgaagca gcatgacttt ttcaagagcg ccatgcccga    2340
gggctatgtg caggagagaa ccatcttttt caaagatgac gggaactaca agacccgcgc    2400
tgaagtcaag ttcgaaggtg acaccctggt gaatagaatc gagctgaagg gcattgactt    2460
taaggaggat ggaaacattc tcggccacaa gctggaatac aactataact cccacaatgt    2520
gtacatcatg gccgacaagc aaaagaatgg catcaaggtc aacttcaaga tcagacacaa    2580
cattgaggat ggatccgtgc agctggccga ccattatcaa cagaacactc caatcggcga    2640
cggccctgtg ctcctcccag acaaccatta cctgtccacc cagtctgccc tgtctaaaga    2700
```

```
tcccaacgaa aagagagacc acatggtcct gctggagttt gtgaccgctg ctgggatcac    2760
acatggcatg gacgagctgt acaagtgagc ggccgcgggg atccagacat gataagatac    2820
attgatgagt ttggacaaac cacaactaga atgcagtgaa aaaaatgctt tatttgtgaa    2880
atttgtgatg ctattgcttt atttgtaacc attataagct gcaataaaca agttaacaac    2940
aacaattgca ttcattttat gtttcaggtt caggggagg tgtgggaggt tttttagtcg     3000
acctcgagca gtgtggtttt gcaagaggaa gcaaaaagcc tctccaccca ggcctggaat    3060
gtttccaccc aagtcgaagg cagtgtggtt ttgcaagagg aagcaaaaag cctctccacc    3120
caggcctgga atgtttccac ccaatgtcga gcaaccccgc ccagcgtctt gtcattggcg    3180
aattcgaaca cgcagatgca gtcggggcgg cgcggtccca ggtccacttc gcatattaag    3240
gtgacgcgtg tggcctcgaa caccgagcga ccctgcagcc aatatgggat cggccattga    3300
acaagatgga ttgcacgcag gttctccggc cgcttgggtg gagaggctat tcggctatga    3360
ctgggcacaa cagacaatcg gctgctctga tgccgccgtg ttccggctgt cagcgcaggg    3420
gcgcccggtt cttttgtca agaccgacct gtccggtgcc ctgaatgaac tgcaggacga    3480
ggcagcgcgg ctatcgtggc tggccacgac gggcgttcct tgcgcagctg tgctcgacgt    3540
tgtcactgaa gcgggaaggg actggctgct attgggcgaa gtgccggggc aggatctcct    3600
gtcatctcac cttgctcctg ccgagaaagt atccatcatg gctgatgcaa tgcggcggct    3660
gcatacgctt gatccggcta cctgcccatt cgaccaccaa gcgaaacatc gcatcgagcg    3720
agcacgtact cggatggaag ccggtcttgt cgatcaggat gatctggacg aagagcatca    3780
ggggctcgcg ccagccgaac tgttcgccag gctcaaggcg cgcatgcccg acggcgagga    3840
tctcgtcgtg acccatggcg atgcctgctt gccgaatatc atggtggaaa atggccgctt    3900
ttctggattc atcgactgtg gccggctggg tgtggcggac cgctatcagg acatagcgtt    3960
ggctacccgt gatattgctg aagagcttgg cggcgaatgg gctgaccgct tcctcgtgct    4020
ttacggtatc gccgctcccg attcgcagcg catcgccttc tatcgccttc ttgacgagtt    4080
cttctgaggg gatccgtcga ctagagctcg ctgatcagcc tcgactgtgc cttctagttg    4140
ccagccatct gttgtttgcc cctcccccgt gccttccttg accctggaag gtgccactcc    4200
cactgtcctt tcctaataaa atgaggaaat tgcatcgcat tgtctgagta ggtgtcattc    4260
tattctgggg ggtggggtgg ggcaggacag caagggggag gattgggaag acaatagcag    4320
gcatgctggg gagagatcta ggaaccccta gtgatggagt tggccactcc ctctctgcgc    4380
gctcgctcgc tcactgaggc cgcccgggca aagcccgggc gtcgggcgac ctttggtcgc    4440
ccggcctcag tgagcgagcg agcgcgcaga gagggagtgg ccaaccccc ccccccccc     4500 cctgcagccc tgcattaatg aatcggccaa cgcgcgggga gaggcggttt gcgtattggg    4560
cgctcttccg cttcctcgct cactgactcg ctgcgctcgg tcgttcggct gcggcgagcg    4620
gtatcagctc actcaaaggc ggtaatacgg ttatccacag aatcagggga taacgcagga    4680
aagaacatgt gagcaaaagg ccagcaaaag gccaggaacc gtaaaaaggc cgcgttgctg    4740
gcgtttttcc ataggctccg cccccctgac gagcatcaca aaaatcgacg ctcaagtcag    4800
aggtggcgaa acccgacagg actataaaga taccaggcgt ttccccctgg aagctccctc    4860
gtgcgctctc ctgttccgac cctgccgctt accggatacc tgtccgcctt tctcccttcg    4920
ggaagcgtgg cgctttctca atgctcacgc tgtaggtatc tcagttcggt gtaggtcgtt    4980
cgctccaagc tgggctgtgt gcacgaaccc cccgttcagc ccgaccgctg cgccttatcc    5040
```

```
ggtaactatc gtcttgagtc caacccggta agacacgact tatcgccact ggcagcagcc    5100
actggtaaca ggattagcag agcgaggtat gtaggcggtg ctacagagtt cttgaagtgg    5160
tggcctaact acggctacac tagaaggaca gtatttggta tctgcgctct gctgaagcca    5220
gttaccttcg gaaaaagagt tggtagctct tgatccggca acaaaccac cgctggtagc     5280
ggtggttttt ttgtttgcaa gcagcagatt acgcgcagaa aaaaggatc tcaagaagat    5340
cctttgatct tttctacggg gtctgacgct cagtggaacg aaaactcacg ttaagggatt    5400
ttggtcatga gattatcaaa aaggatcttc acctagatcc ttttaaatta aaaatgaagt    5460
tttaaatcaa tctaaagtat atatgagtaa acttggtctg acagttacca atgcttaatc    5520
agtgaggcac ctatctcagc gatctgtcta tttcgttcat ccatagttgc ctgactcccc    5580
gtcgtgtaga taactacgat acgggagggc ttaccatctg gccccagtgc tgcaatgata    5640
ccgcgagacc cacgctcacc ggctccagat ttatcagcaa taaaccagcc agccggaagg    5700
gccgagcgca gaagtggtcc tgcaacttta tccgcctcca tccagtctat taattgttgc    5760
cgggaagcta gagtaagtag ttcgccagtt aatagtttgc gcaacgttgt tgccattgct    5820
acaggcatcg tggtgtcacg ctcgtcgttt ggtatggctt cattcagctc cggttcccaa    5880
cgatcaaggc gagttacatg atcccccatg ttgtgcaaaa aagcggttag ctccttcggt    5940
cctccgatcg ttgtcagaag taagttggcc gcagtgttat cactcatggt tatggcagca    6000
ctgcataatt ctcttactgt catgccatcc gtaagatgct tttctgtgac tggtgagtac    6060
tcaaccaagt cattctgaga atagtgtatg cggcgaccga gttgctcttg cccggcgtca    6120
atacgggata ataccgcgcc acatagcaga actttaaaag tgctcatcat tggaaaacgt    6180
tcttcgggggc gaaaactctc aaggatctta ccgctgttga gatccagttc gatgtaaccc    6240
actcgtgcac ccaactgatc ttcagcatct tttactttca ccagcgtttc tgggtgagca    6300
aaaacaggaa ggcaaaatgc cgcaaaaaag ggaataaggg cgacacggaa atgttgaata    6360
ctcatactct tccttttca atattattga agcatttatc agggttattg tctcatgagc    6420
ggatacatat ttgaatgtat ttagaaaaat aaacaaatag gggttccgcg cacatttccc    6480
cgaaaagtgc cacctgacgt ctaagaaacc attattatca tgacattaac ctataaaaat    6540
aggcgtatca cgaggccctt tcgtctcgcg cgtttcggtg atgacggtga aaacctctga    6600
cacatgcagc tcccggagac ggtcacagct tgtctgtaag cggatgccgg gagcagacaa    6660
gcccgtcagg gcgcgtcagc gggtgttggc gggtgtcggg gctggcttaa ctatgcggca    6720
tcagagcaga ttgtactgag agtgcaccat atgcggtgtg aaataccgca cagatgcgta    6780
aggagaaaat accgcatcag gaaattgtaa acgttaatat tttgttaaaa ttcgcgttaa    6840
attttttgtta aatcagctca ttttttaacc aataggccga atcggcaaa atcccttata    6900
aatcaaaaga atagaccgag atagggttga gtgttgttcc agtttggaac aagagtccac    6960
tattaaagaa cgtggactcc aacgtcaaag ggcgaaaaac cgtctatcag ggcgatggcc    7020
cactacgtga accatcaccc taatcaagtt ttttggggtc gaggtgccgt aaagcactaa    7080
atcggaaccc taaagggagc ccccgattta gagcttgacg ggggaaagccg gcgaacgtgg    7140
cgagaaagga agggaagaaa gcgaaaggag cgggcgctag ggcgctggca agtgtagcgg    7200
tcacgctgcg cgtaaccacc acacccgccg cgcttaatgc gccgctacag ggcgcgtcgc    7260
gccattcgcc attcaggcta cgcaactgtt gggaagggcg atcggtgcgg gcctcttcgc    7320
tattacgcca ggctgca                                                    7337
```

```
<210> SEQ ID NO 27
<211> LENGTH: 8223
<212> TYPE: DNA
<213> ORGANISM: Artificial Sequence
<220> FEATURE:
<223> OTHER INFORMATION: PolyA-3XmiR-CB-AAT
<220> FEATURE:
<221> NAME/KEY: misc_feature
<222> LOCATION: (17)..(163)
<223> OTHER INFORMATION: Inverted terminal repeats (ITR)
<220> FEATURE:
<221> NAME/KEY: enhancer
<222> LOCATION: (182)..(548)
<223> OTHER INFORMATION: enhancer
<220> FEATURE:
<221> NAME/KEY: promoter
<222> LOCATION: (549)..(1795)
<223> OTHER INFORMATION: Chicken beta actin promoter
<220> FEATURE:
<221> NAME/KEY: Intron
<222> LOCATION: (826)..(1795)
<223> OTHER INFORMATION: Intron
<220> FEATURE:
<221> NAME/KEY: misc_feature
<222> LOCATION: (1796)..(1898)
<223> OTHER INFORMATION: Globin
<220> FEATURE:
<221> NAME/KEY: gene
<222> LOCATION: (1921)..(3174)
<223> OTHER INFORMATION: Hardened alpha-1 antitrypsin (AAT)
<220> FEATURE:
<221> NAME/KEY: misc_signal
<222> LOCATION: (3175)..(3204)
<223> OTHER INFORMATION: Cmyc-tag
<220> FEATURE:
<221> NAME/KEY: misc_feature
<222> LOCATION: (3237)..(3264)
<223> OTHER INFORMATION: 5' miR
<220> FEATURE:
<221> NAME/KEY: misc_feature
<222> LOCATION: (3265)..(3285)
<223> OTHER INFORMATION: Antisense 901
<220> FEATURE:
<221> NAME/KEY: misc_feature
<222> LOCATION: (3305)..(3323)
<223> OTHER INFORMATION: Sense delta 2
<220> FEATURE:
<221> NAME/KEY: misc_feature
<222> LOCATION: (3328)..(3368)
<223> OTHER INFORMATION: 3' miR
<220> FEATURE:
<221> NAME/KEY: misc_feature
<222> LOCATION: (3381)..(3409)
<223> OTHER INFORMATION: 5' miR
<220> FEATURE:
<221> NAME/KEY: misc_feature
<222> LOCATION: (3410)..(3430)
<223> OTHER INFORMATION: Antisense 914
<220> FEATURE:
<221> NAME/KEY: misc_feature
<222> LOCATION: (3450)..(3468)
<223> OTHER INFORMATION: Sense delta 2
<220> FEATURE:
<221> NAME/KEY: misc_feature
<222> LOCATION: (3473)..(3513)
<223> OTHER INFORMATION: 3' miR
<220> FEATURE:
<221> NAME/KEY: misc_feature
<222> LOCATION: (3526)..(3554)
<223> OTHER INFORMATION: 5' miR
<220> FEATURE:
<221> NAME/KEY: misc_feature
<222> LOCATION: (3555)..(3575)
<223> OTHER INFORMATION: Antisense 943
<220> FEATURE:
<221> NAME/KEY: misc_feature
<222> LOCATION: (3595)..(3613)
<223> OTHER INFORMATION: Sense delta 2
<220> FEATURE:
```

```
<221> NAME/KEY: misc_feature
<222> LOCATION: (3618)..(3658)
<223> OTHER INFORMATION: 3' miR
<220> FEATURE:
<221> NAME/KEY: polyA_signal
<222> LOCATION: (3677)..(3889)
<223> OTHER INFORMATION: polyA tail
<220> FEATURE:
<221> NAME/KEY: promoter
<222> LOCATION: (4030)..(4158)
<223> OTHER INFORMATION: thymidine kinase promoter (Tkp)
<220> FEATURE:
<221> NAME/KEY: gene
<222> LOCATION: (4170)..(4973)
<223> OTHER INFORMATION: Neomycin resistance gene
<220> FEATURE:
<221> NAME/KEY: misc_feature
<222> LOCATION: (5226)..(5371)
<223> OTHER INFORMATION: Inverted terminal repeats (ITR)
<220> FEATURE:
<221> NAME/KEY: gene
<222> LOCATION: (6391)..(7251)
<223> OTHER INFORMATION: Ampicillin resistance gene (complement)

<400> SEQUENCE: 27
gggggggggg ggggggggtt ggccactccc tctctgcgcg ctcgctcgct cactgaggcc      60
gggcgaccaa aggtcgcccg acgcccgggc tttgccccggg cggcctcagt gagcgagcga    120
gcgcgcagag agggagtggc caactccatc actaggggtt cctagatctg aattcggtac    180
cctagttatt aatagtaatc aattacgggg tcattagttc atagcccata tatggagttc    240
cgcgttacat aacttacggt aaatggcccg cctggctgac cgcccaacga ccccccgccca    300 ttgacgtcaa taatgacgta tgttcccata gtaacgccaa tagggacttt ccattgacgt    360
caatgggtgg actatttacg gtaaactgcc cacttggcag tacatcaagt gtatcatatg    420
ccaagtacgc ccctattga cgtcaatgac ggtaaatggc ccgcctggca ttatgcccag    480
tacatgacct tatgggactt tcctacttgg cagtacatct acgtattagt catcgctatt    540
accatggtcg aggtgagccc cacgttctgc ttcactctcc ccatctcccc cccctcccca    600
cccccaattt tgtatttatt tattttttaa ttattttgtg cagcgatggg ggcggggggg    660
gggggggggc gcgcgccagg cggggcgggg cggggcgagg ggcggggcgg ggcgaggcgg    720
agaggtgcgg cggcagccaa tcagagcggc gcgctccgaa agtttccttt tatggcgagg    780
cggcggcggc ggcggcccta taaaaagcga agcgcgcggc gggcgggagt cgctgcgacg    840
ctgccttcgc cccgtgcccc gctccgccgc cgcctcgcgc cgcccgcccc ggctctgact    900
gaccgcgtta ctcccacagg tgagcggggcg ggacggccct tctcctccgg gctgtaatta    960
gcgcttggtt taatgacggc ttgtttcttt tctgtggctg cgtgaaagcc ttgaggggct   1020 ccggagggc cctttgtgcg ggggggagcg gctcggggg tgcgtgcgtg tgtgtgtgcg   1080
tggggagcgc cgcgtgcggc ccgcgctgcc cggcggctgt gagcgctgcg ggcgcggcgc   1140
ggggctttgt gcgctccgca gtgtgcgcga gggagcgcg gccggggcg gtgccccgcg   1200 gtgcgggggg ggctgcgagg ggaacaaagg ctgcgtgcgg ggtgtgtgcg tgggggggtg   1260
agcagggggt gtgggcgcgg cggtcgggct gtaaccccc cctgcacccc cctccccgag   1320
ttgctgagca cggcccggct tcgggtgcgg ggctccgtac ggggcgtggc gcggggctcg   1380
ccgtgccggg cggggggtgg cggcaggtgg gggtgccggg cggggcgggg ccgcctcggg   1440 cggggagg ctcggggag gggcgcggcg gccccggag cgccggcggc tgtcgaggcg   1500
cggcgagccg cagccattgc cttttatggt aatcgtgcga gagggcgcag ggacttcctt   1560
tgtcccaaat ctgtgcggag ccgaaatctg ggaggcgccg ccgcaccccc tctagcgggc   1620
```

```
gcggggcgaa gcggtgcggc gccggcagga aggaaatggg cggggagggc cttcgtgcgt    1680
cgccgcgccg ccgtccccTT ctccctctcc agcctcgggg ctgtccgcgg ggggacggct    1740
gccttcgggg gggacggggc agggcggggt tcggcttctg gcgtgtgacc ggcggctcta    1800
gagcctctgc taaccatgtt catgccttct tcttttTcct acagctcctg gcaacgtgc     1860 tggttattgt gctgtctcat cattttggca agaattcct cgaagatcta ggcctgcagg     1920
atgccgtctt ctgtctcgtg gggcatcctc ctgctggcag gctgtgctg cctggtccct     1980 gtctccctgg ctgaggatcc cagggagat gctgcccaga agacagatac atcccaccat     2040
gatcaggatc acccaacctt caacaagatc accccaacc tggctgagtt cgccttcagc     2100
ctataccgcc agctggcaca ccagtccaac agcaccaata tcttcttctc cccagtgagc    2160
atcgctacag cctttgcaat gctctccctg ggaccaagg ctgacactca cgatgaaatc     2220
ctggagggcc tgaatttcaa cctcacggag attccggagg ctcagatcca tgaaggcttc    2280
caggaactcc tccgtaccct caaccagcca gacagccagc tccagctgac caccggcaat    2340
ggcctgttcc tcagcgaggg cctgaagcta gtggataagt ttttggagga tgttaaaaag    2400
ttgtaccact cagaagcctt cactgtcaac ttcggggaca ccgaagaggc caagaaacag    2460
atcaacgatt acgtggagaa gggtactcaa gggaaaattg tggatttggt caaggagctt    2520
gacagagaca cagttttgc tctggtgaat tacatcttct ttaaaggcaa atgggagaga     2580
ccctttgaag tcaaggacac cgaggaagag gacttccacg tggaccaggt gaccaccgtg    2640
aaggtgccta tgatgaagcg tttaggcatg tttaacatcc agcactgtaa gaagctgtcc    2700
agctgggtgc tgctgatgaa atacctgggc aatgccaccg ccatcttctt cctgcctgat    2760
gaggggaaac tacagcacct ggaaaatgaa ctcacccacg atatcatcac caagttcctg    2820
gaaaatgaag atcgccgtag cgcttctctg cacctgccca gttaagcat caccggcacg    2880 tacgacctga gagcgtcct gggtcaactg ggcatcacta aggtcttcag caatggggct     2940
gacctctccg gggtcacaga ggaggcaccc ctgaagctct ccaaggccgt gcataaggct    3000
gtgctgacca tcgacgagaa agggactgaa gctgctgggg ccatgttTTt agaggccata    3060
cccatgtcta tccccccga ggtcaagttc aacaaaccct tgtcttctt aatgattgaa     3120 caaaatacca agtctcccct cttcatggga aagtggtga atcccaccca aaaagagcag    3180
aagctgatca gcgaggagga cctgtagcct gcaggcgccg gcgaccggtg ctagccctgg    3240
aggcttgctg aaggctgtat gctgtaagct ggcagacctt ctgtcgtttt ggccactgac    3300
tgacgacaga agctgccagc ttacaggaca caaggcctgt tactagcact cacatggaac    3360
aaatggccac cggtatgcat cctggaggct tgctgaaggc tgtatgctga atgtaagctg    3420
gcagaccttc gttttggcca ctgactgacg aaggtctcag cttacattca ggacacaagg    3480
cctgttacta gcactcacat ggaacaaatg gccgctagct cgcgacctgg aggcttgctg    3540
aaggctgtat gctgataggt tccagtaatg acaggtttt ggccactgac tgacctgtcc     3600
atctggaacc tatcaggaca caaggcctgt tactagcact cacatggaac aaatggcctc    3660
gcgatgcatc tagagcggcc gcggggatcc agacatgata agatacattg atgagtttgg    3720
acaaaccaca actagaatgc agtgaaaaaa atgctttatt tgtgaaattt gtgatgctat    3780
tgctttattt gtaaccatta taagctgcaa taaacaagtt aacaacaaca attgcattca    3840
ttttatgttt caggttcagg gggaggtgtg ggaggttTTT tagtcgacct cgagcagtgt    3900
ggttttgcaa gaggaagcaa aaagcctctc cacccaggcc tggaatgttt ccacccaagt    3960
```

| | |
|---|---|
| cgaaggcagt gtggttttgc aagaggaagc aaaaagcctc tccacccagg cctggaatgt | 4020 |
| ttccacccaa tgtcgagcaa ccccgcccag cgtcttgtca ttggcgaatt cgaacacgca | 4080 |
| gatgcagtcg gggcggcgcg gtcccaggtc cacttcgcat attaaggtga cgcgtgtggc | 4140 |
| ctcgaacacc gagcgaccct gcagccaata tgggatcggc cattgaacaa gatggattgc | 4200 |
| acgcaggttc tccggccgct tgggtggaga ggctattcgg ctatgactgg gcacaacaga | 4260 |
| caatcggctg ctctgatgcc gccgtgttcc ggctgtcagc gcaggggcgc ccggttcttt | 4320 |
| ttgtcaagac cgacctgtcc ggtgccctga atgaactgca ggacgaggca gcgcggctat | 4380 |
| cgtggctggc cacgacgggc gttccttgcg cagctgtgct cgacgttgtc actgaagcgg | 4440 |
| gaagggactg gctgctattg ggcgaagtgc cggggcagga tctcctgtca tctcaccttg | 4500 |
| ctcctgccga aaagtatcc atcatggctg atgcaatgcg gcggctgcat acgcttgatc | 4560 |
| cggctacctg cccattcgac caccaagcga acatcgcat cgagcgagca cgtactcgga | 4620 |
| tggaagccgg tcttgtcgat caggatgatc tggacgaaga gcatcagggg ctcgcgccag | 4680 |
| ccgaactgtt cgccaggctc aaggcgcgca tgcccgacgg cgaggatctc gtcgtgaccc | 4740 |
| atggcgatgc ctgcttgccg aatatcatgg tggaaaatgg ccgcttttct ggattcatcg | 4800 |
| actgtggccg gctgggtgtg gcggaccgct atcaggacat agcgttggct acccgtgata | 4860 |
| ttgctgaaga gcttggcggc gaatgggctg accgcttcct cgtgctttac ggtatcgccg | 4920 |
| ctcccgattc gcagcgcatc gccttctatc gccttcttga cgagttcttc tgagggggatc | 4980 |
| cgtcgactag agctcgctga tcagcctcga ctgtgccttc tagttgccag ccatctgttg | 5040 |
| tttgcccctc cccgtgcct tccttgaccc tggaaggtgc cactcccact gtcctttcct | 5100 |
| aataaaatga ggaaattgca tcgcattgtc tgagtaggtg tcattctatt ctggggggtg | 5160 |
| gggtggggca ggacagcaag ggggaggatt gggaagacaa tagcaggcat gctgggaga | 5220 |
| gatctaggaa cccctagtga tggagttggc cactccctct ctgcgcgctc gctcgctcac | 5280 |
| tgaggccgcc cggcaaagc ccgggcgtcg ggcgaccttt ggtcgcccgg cctcagtgag | 5340 |
| cgagcgagcg cgcagagagg gagtggccaa ccccccccc ccccccctg cagccctgca | 5400 |
| ttaatgaatc ggccaacgcg cggggagagg cggtttgcgt attgggcgct cttccgcttc | 5460 |
| ctcgctcact gactcgctgc gctcggtcgt tcggctgcgg cgagcggtat cagctcactc | 5520 |
| aaaggcggta atacggttat ccacagaatc aggggataac gcaggaaaga acatgtgagc | 5580 |
| aaaaggccag caaaaggcca ggaaccgtaa aaaggccgcg ttgctggcgt ttttccatag | 5640 |
| gctccgcccc cctgacgagc atcacaaaaa tcgacgctca agtcagaggt ggcgaaaccc | 5700 |
| gacaggacta taaagatacc aggcgtttcc ccctggaagc tccctcgtgc gctctcctgt | 5760 |
| tccgaccctg ccgcttaccg gatacctgtc cgcctttctc ccttcgggaa gcgtggcgct | 5820 |
| ttctcaatgc tcacgctgta ggtatctcag ttcggtgtag tcgttcgct ccaagctggg | 5880 |
| ctgtgtgcac gaaccccccg ttcagcccga ccgctgcgcc ttatccggta actatcgtct | 5940 |
| tgagtccaac ccggtaagac acgacttatc gccactggca gcagccactg gtaacaggat | 6000 |
| tagcagagcg aggtatgtag gcggtgctac agagttcttg aagtggtggc ctaactacgg | 6060 |
| ctacactaga aggacagtat ttggtatctg cgctctgctg aagccagtta ccttcggaaa | 6120 |
| aagagttggt agctcttgat ccggcaaaca aaccaccgct ggtagcggtg ttttttttgt | 6180 |
| ttgcaagcag cagattacgc gcagaaaaaa aggatctcaa gaagatcctt tgatcttttc | 6240 |
| tacgggtct gacgctcagt ggaacgaaaa ctcacgttaa gggattttgg tcatgagatt | 6300 |
| atcaaaaagg atcttcacct agatcctttt aaattaaaaa tgaagtttta aatcaatcta | 6360 |

```
aagtatatat gagtaaactt ggtctgacag ttaccaatgc ttaatcagtg aggcacctat    6420
ctcagcgatc tgtctatttc gttcatccat agttgcctga ctccccgtcg tgtagataac    6480
tacgatacgg gagggcttac catctggccc cagtgctgca atgataccgc gagacccacg    6540
ctcaccggct ccagatttat cagcaataaa ccagccagcc ggaagggccg agcgcagaag    6600
tggtcctgca actttatccg cctccatcca gtctattaat tgttgccggg aagctagagt    6660
aagtagttcg ccagttaata gtttgcgcaa cgttgttgcc attgctacag gcatcgtggt    6720
gtcacgctcg tcgtttggta tggcttcatt cagctccggt tcccaacgat caaggcgagt    6780
tacatgatcc cccatgttgt gcaaaaaagc ggttagctcc ttcggtcctc cgatcgttgt    6840
cagaagtaag ttggccgcag tgttatcact catggttatg gcagcactgc ataattctct    6900
tactgtcatg ccatccgtaa gatgcttttc tgtgactggt gagtactcaa ccaagtcatt    6960
ctgagaatag tgtatgcggc gaccgagttg ctcttgcccg gcgtcaatac gggataatac    7020
cgcgccacat agcagaactt taaaagtgct catcattgga aaacgttctt cggggcgaaa    7080
actctcaagg atcttaccgc tgttgagatc cagttcgatg taacccactc gtgcacccaa    7140
ctgatcttca gcatctttta ctttcaccag cgtttctggg tgagcaaaaa caggaaggca    7200
aaatgccgca aaaaagggaa taagggcgac acggaaatgt tgaatactca tactcttcct    7260
ttttcaatat tattgaagca tttatcaggg ttattgtctc atgagcggat acatatttga    7320
atgtatttag aaaaataaac aatagggggt tccgcgcaca tttccccgaa aagtgccacc    7380
tgacgtctaa gaaaccatta ttatcatgac attaacctat aaaaataggc gtatcacgag    7440
gccctttcgt ctcgcgcgtt tcggtgatga cggtgaaaac ctctgacaca tgcagctccc    7500
ggagacggtc acagcttgtc tgtaagcgga tgccgggagc agacaagccc gtcagggcgc    7560
gtcagcgggt gttggcgggt gtcggggctg gcttaactat gcggcatcag agcagattgt    7620
actgagagtg caccatatgc ggtgtgaaat accgcacaga tgcgtaagga gaaaataccg    7680
catcaggaaa ttgtaaacgt taatattttg ttaaaattcg cgttaaattt ttgttaaatc    7740
agctcatttt ttaaccaata ggccgaaatc ggcaaaatcc cttataaatc aaaagaatag    7800
accgagatag ggttgagtgt tgttccagtt tggaacaaga gtccactatt aaagaacgtg    7860
gactccaacg tcaaagggcg aaaaaccgtc tatcagggcg atggcccact acgtgaacca    7920
tcaccctaat caagttttt ggggtcgagg tgccgtaaag cactaaatcg aaccctaaa     7980 gggagccccc gatttagagc ttgacgggga agccggcga acgtggcgag aaaggaaggg    8040
aagaaagcga aaggagcggg cgctagggcg ctggcaagtg tagcggtcac gctgcgcgta    8100
accaccacac ccgccgcgct taatgcgccg ctacagggcg cgtcgcgcca ttcgccattc    8160
aggctacgca actgttggga agggcgatcg gtgcgggcct cttcgctatt acgccaggct    8220
gca                                                                 8223
```

<210> SEQ ID NO 28  
<211> LENGTH: 8360  
<212> TYPE: DNA  
<213> ORGANISM: Artificial Sequence  
<220> FEATURE:  
<223> OTHER INFORMATION: Double-6XmiR-CB-AAT  
<220> FEATURE:  
<221> NAME/KEY: misc_feature  
<222> LOCATION: (17)..(163)  
<223> OTHER INFORMATION: Inverted terminal repeats (ITR)  
<220> FEATURE:  
<221> NAME/KEY: enhancer  
<222> LOCATION: (182)..(548)

```
<223> OTHER INFORMATION: Enhancer
<220> FEATURE:
<221> NAME/KEY: promoter
<222> LOCATION: (549)..(1482)
<223> OTHER INFORMATION: Chicken beta actin promoter
<220> FEATURE:
<221> NAME/KEY: Intron
<222> LOCATION: (826)..(1482)
<223> OTHER INFORMATION: Intron
<220> FEATURE:
<221> NAME/KEY: misc_feature
<222> LOCATION: (1503)..(1529)
<223> OTHER INFORMATION: 5' miR
<220> FEATURE:
<221> NAME/KEY: misc_feature
<222> LOCATION: (1530)..(1550)
<223> OTHER INFORMATION: Antisense 901
<220> FEATURE:
<221> NAME/KEY: misc_feature
<222> LOCATION: (1570)..(1588)
<223> OTHER INFORMATION: Sense delta 2
<220> FEATURE:
<221> NAME/KEY: misc_feature
<222> LOCATION: (1593)..(1633)
<223> OTHER INFORMATION: 3' miR
<220> FEATURE:
<221> NAME/KEY: misc_feature
<222> LOCATION: (1646)..(1674)
<223> OTHER INFORMATION: 5' miR
<220> FEATURE:
<221> NAME/KEY: misc_feature
<222> LOCATION: (1675)..(1695)
<223> OTHER INFORMATION: Antisense 914
<220> FEATURE:
<221> NAME/KEY: misc_feature
<222> LOCATION: (1715)..(1733)
<223> OTHER INFORMATION: Sense delta 2
<220> FEATURE:
<221> NAME/KEY: misc_feature
<222> LOCATION: (1738)..(1778)
<223> OTHER INFORMATION: 3' miR
<220> FEATURE:
<221> NAME/KEY: misc_feature
<222> LOCATION: (1791)..(1819)
<223> OTHER INFORMATION: 5' miR
<220> FEATURE:
<221> NAME/KEY: misc_feature
<222> LOCATION: (1820)..(1840)
<223> OTHER INFORMATION: Antisense 943
<220> FEATURE:
<221> NAME/KEY: misc_feature
<222> LOCATION: (1860)..(1878)
<223> OTHER INFORMATION: Sense delta 2
<220> FEATURE:
<221> NAME/KEY: misc_feature
<222> LOCATION: (1883)..(1923)
<223> OTHER INFORMATION: 3' miR
<220> FEATURE:
<221> NAME/KEY: misc_feature
<222> LOCATION: (1936)..(2035)
<223> OTHER INFORMATION: Globin
<220> FEATURE:
<221> NAME/KEY: gene
<222> LOCATION: (2058)..(3311)
<223> OTHER INFORMATION: Hardened alpha-1 antitrypsin (AAT)
<220> FEATURE:
<221> NAME/KEY: misc_signal
<222> LOCATION: (3312)..(3341)
<223> OTHER INFORMATION: Cmyc-tag
<220> FEATURE:
<221> NAME/KEY: misc_feature
<222> LOCATION: (3374)..(3401)
<223> OTHER INFORMATION: 5' miR
<220> FEATURE:
<221> NAME/KEY: misc_feature
<222> LOCATION: (3402)..(3422)
<223> OTHER INFORMATION: Antisense 901
<220> FEATURE:
<221> NAME/KEY: misc_feature
```

```
<222> LOCATION: (3442)..(3460)
<223> OTHER INFORMATION: Sense delta 2
<220> FEATURE:
<221> NAME/KEY: misc_feature
<222> LOCATION: (3465)..(3505)
<223> OTHER INFORMATION: 3' miR
<220> FEATURE:
<221> NAME/KEY: misc_feature
<222> LOCATION: (3518)..(3546)
<223> OTHER INFORMATION: 5' miR
<220> FEATURE:
<221> NAME/KEY: misc_feature
<222> LOCATION: (3547)..(3567)
<223> OTHER INFORMATION: Antisense 914
<220> FEATURE:
<221> NAME/KEY: misc_feature
<222> LOCATION: (3587)..(3605)
<223> OTHER INFORMATION: Sense delta 2
<220> FEATURE:
<221> NAME/KEY: misc_feature
<222> LOCATION: (3610)..(3650)
<223> OTHER INFORMATION: 3' miR
<220> FEATURE:
<221> NAME/KEY: misc_feature
<222> LOCATION: (3663)..(3691)
<223> OTHER INFORMATION: 5' miR
<220> FEATURE:
<221> NAME/KEY: misc_feature
<222> LOCATION: (3692)..(3712)
<223> OTHER INFORMATION: Antisense 943
<220> FEATURE:
<221> NAME/KEY: misc_feature
<222> LOCATION: (3732)..(3750)
<223> OTHER INFORMATION: Sense delta 2
<220> FEATURE:
<221> NAME/KEY: misc_feature
<222> LOCATION: (3755)..(3795)
<223> OTHER INFORMATION: 3' miR
<220> FEATURE:
<221> NAME/KEY: polyA_signal
<222> LOCATION: (3814)..(4026)
<223> OTHER INFORMATION: polyA tail
<220> FEATURE:
<221> NAME/KEY: promoter
<222> LOCATION: (4167)..(4295)
<223> OTHER INFORMATION: thymidine kinase promoter (Tkp)
<220> FEATURE:
<221> NAME/KEY: gene
<222> LOCATION: (4307)..(5110)
<223> OTHER INFORMATION: Neomycin resistance gene
<220> FEATURE:
<221> NAME/KEY: misc_feature
<222> LOCATION: (5363)..(5508)
<223> OTHER INFORMATION: Inverted terminal repeats (ITR)
<220> FEATURE:
<221> NAME/KEY: gene
<222> LOCATION: (6528)..(7388)
<223> OTHER INFORMATION: Ampicillin resistance gene (complement)

<400> SEQUENCE: 28
```

| | | | | | |
|---|---|---|---|---|---|
| gggggggggg | gggggggggtt | ggccactccc | tctctgcgcg | ctcgctcgct | cactgaggcc | 60 |
| gggcgaccaa | aggtcgcccg | acgcccgggc | tttgcccggg | cggcctcagt | gagcgagcga | 120 |
| gcgcgcagag | agggagtggc | caactccatc | actaggggtt | cctagatctg | aattcggtac | 180 |
| cctagttatt | aatagtaatc | aattacgggg | tcattagttc | atagcccata | tatggagttc | 240 |
| cgcgttacat | aacttacggt | aaatggcccg | cctggctgac | cgcccaacga | cccccgccca | 300 |
| ttgacgtcaa | taatgacgta | tgttcccata | gtaacgccaa | tagggacttt | ccattgacgt | 360 |
| caatgggtgg | actatttacg | gtaaactgcc | cacttggcag | tacatcaagt | gtatcatatg | 420 |
| ccaagtacgc | cccctattga | cgtcaatgac | ggtaaatggc | ccgcctggca | ttatgcccag | 480 |
| tacatgacct | tatgggactt | tcctacttgg | cagtacatct | acgtattagt | catcgctatt | 540 |

```
accatggtcg aggtgagccc cacgttctgc ttcactctcc ccatctcccc cccctcccca    600
ccccaattt  tgtatttatt tatttttaa  ttattttgtg cagcgatggg ggcggggggg    660
ggggggggc  gcgcgccagg cggggcgggg cggggcgagg ggcggggcgg ggcgaggcgg    720
agaggtgcgg cggcagccaa tcagagcggc gcgctccgaa agtttccttt tatggcgagg    780
cggcggcggc ggcggcccta taaaaagcga agcgcgcggc gggcgggagt cgctgcgacg    840
ctgccttcgc cccgtgcccc gctccgccgc cgcctcgcgc cgcccgcccc ggctctgact    900
gaccgcgtta ctcccacagg tgagcgggcg ggacggccct tctcctccgg gctgtaatta    960
gcgcttggtt taatgacggc ttgtttcttt tctgtggctg cgtgaaagcc ttgaggggct   1020
ccgggagggc cctttgtgcg ggggggagcg gctcggggg  tgcgtgcgtg tgtgtgtgcg   1080
tggggagcgc cgccgtgcggc ccgcgctgcc cggcggctgt gagcgctgcg ggcgcggcgc   1140
ggggctttgt gcgctccgca gtgtgcgcga ggggagcgcg gccgggggcg gtgccccgcg   1200
gtgcggggg  ggctgcgagg ggaacaaagg ctgcgtgcgg ggtgtgtgcg tggggggtg    1260
agcagggggt gtgggcgcgg cggtcgggct gtaaccccc  cctgcacccc cctccccgag   1320
ttgctgagca cggcccggct tcgggtgcgg ggctccgtac ggggcgtggc gcgggctcg    1380
ccgtgccggg cgggggtgg  cggcaggtgg gggtgccggg cggggcgggg ccgcctcggg   1440
ccggggaggg ctcggggag  gggcgcggcg gcccccggag cgccggcgac cggtgctagc   1500
cctggaggct tgctgaaggc tgtatgctgt aagctggcag accttctgtc gttttggcca   1560
ctgactgacg acagaagctg ccagcttaca ggacacaagg cctgttacta gcactcacat   1620
ggaacaaatg gccaccggta tgcatcctgg aggcttgctg aaggctgtat gctgaatgta   1680
agctggcaga ccttcgtttt ggccactgac tgacgaaggt ctcagcttac attcaggaca   1740
caaggcctgt tactagcact cacatggaac aaatggccgc tagctcgcga cctggaggct   1800
tgctgaaggc tgtatgctga taggttccag taatggacag gttttggcca ctgactgacc   1860
tgtccatctg gaacctatca ggacacaagg cctgttacta gcactcacat ggaacaaatg   1920
gcctcgcgat gcatctagag cctctgctaa ccatgttcat gccttcttct ttttcctaca   1980
gctcctggga acgtgctgg  ttattgtgct gtctcatcat tttggcaaag aattcctcga   2040
agatctaggc ctgcaggatg ccgtcttctg tctcgtgggg catcctcctg ctggcaggcc   2100
tgtgctgcct ggtccctgtc tccctggctg aggatcccca gggagatgct gcccagaaga   2160
cagatacatc ccaccatgat caggatcacc caaccttcaa caagatcacc cccaacctgg   2220
ctgagttcgc cttcagccta taccgccagc tggcacacca gtccaacagc accaatatct   2280
tcttctcccc agtgagcatc gctacagcct ttgcaatgct ctccctgggg accaaggctg   2340
acactcacga tgaaatcctg gagggcctga atttcaacct cacggagatt ccggaggctc   2400
agatccatga aggcttccag gaactcctcc gtaccctcaa ccagccagac agccagctcc   2460
agctgaccac cggcaatggc ctgttcctca gcgagggcct gaagctagtg gataagtttt   2520
tggaggatgt taaaaagttg taccactcag aagccttcac tgtcaacttc ggggacaccg   2580
aagaggccaa gaaacagatc aacgattacg tggagaaggg tactcaaggg aaaattgtgg   2640
atttggtcaa ggagcttgac agagacacag tttttgctct ggtgaattac atcttcttta   2700
aaggcaaatg ggagagaccc tttgaagtca aggacaccga ggaagaggac ttccacgtgg   2760
accaggtgac caccgtgaag gtgcctatga tgaagcgttt aggcatgttt aacatccagc   2820
actgtaagaa gctgtccagc tgggtgctgc tgatgaaata cctgggcaat gccaccgcca   2880
tcttcttcct gcctgatgag gggaaactac agcacctgga aaatgaactc acccacgata   2940
```

```
tcatcaccaa gttcctggaa aatgaagatc gccgtagcgc ttctctgcac ctgcccaagt    3000
taagcatcac cggcacgtac gacctgaaga gcgtcctggg tcaactgggc atcactaagg    3060
tcttcagcaa tggggctgac ctctccgggg tcacagagga ggcacccctg aagctctcca    3120
aggccgtgca taaggctgtg ctgaccatcg acgagaaagg gactgaagct gctggggcca    3180 tgttttaga ggccataccc atgtctatcc ccccgaggt caagttcaac aaacccttg     3240 tcttcttaat gattgaacaa ataccaagt ctcccctctt catgggaaaa gtggtgaatc     3300
ccacccaaaa agagcagaag ctgatcagcg aggaggacct gtagcctgca ggcgccggcg    3360
accggtgcta gccctggagg cttgctgaag gctgtatgct gtaagctggc agaccttctg    3420
tcgttttggc cactgactga cgacagaagc tgccagctta caggacacaa ggcctgttac    3480
tagcactcac atggaacaaa tggccaccgg tatgcatcct ggaggcttgc tgaaggctgt    3540
atgctgaatg taagctggca gaccttcgtt ttggccactg actgacgaag gtctcagctt    3600
acattcagga cacaaggcct gttactagca ctcacatgga caaatggcc gctagctcgc     3660 gacctggagg cttgctgaag gctgtatgct gataggttcc agtaatggac aggttttggc    3720
cactgactga cctgtccatc tggaacctat caggacacaa ggcctgttac tagcactcac    3780
atggaacaaa tggcctcgcg atgcatctag agcggccgcg gggatccaga catgataaga    3840
tacattgatg agtttggaca aaccacaact agaatgcagt gaaaaaaatg ctttatttgt    3900
gaaatttgtg atgctattgc tttatttgta accattataa gctgcaataa acaagttaac    3960
aacaacaatt gcattcattt tatgtttcag gttcaggggg aggtgtggga ggttttttag    4020
tcgacctcga gcagtgtggt tttgcaagag gaagcaaaaa gcctctccac ccaggcctgg    4080
aatgttccca cccaagtcga aggcagtgtg gttttgcaag aggaagcaaa agcctctcc     4140 acccaggcct ggaatgtttc cacccaatgt cgagcaaccc cgcccagcgt cttgtcattg    4200
gcgaattcga acacgcagat gcagtcgggg cggcgcggtc ccaggtccac ttcgcatatt    4260
aaggtgacgc gtgtggcctc gaacaccgag cgaccctgca gccaatatgg gatcggccat    4320
tgaacaagat ggattgcacg caggttctcc ggccgcttgg gtggagaggc tattcggcta    4380
tgactgggca caacagacaa tcggctgctc tgatgccgcc gtgttccggc tgtcagcgca    4440
ggggcgcccg gttctttttg tcaagaccga cctgtccggt gccctgaatg aactgcagga    4500
cgaggcagcg cggctatcgt ggctggccac gacgggcgtt ccttgcgcag ctgtgctcga    4560
cgttgtcact gaagcgggaa gggactggct gctattgggc gaagtgccgg ggcaggatct    4620
cctgtcatct caccttgctc ctgccgagaa agtatccatc atggctgatg caatgcggcg    4680
gctgcatacg cttgatccgg ctacctgccc attcgaccac caagcgaaac atcgcatcga    4740
gcgagcacgt actcggatgg aagccggtct tgtcgatcag gatgatctgg acgaagagca    4800
tcaggggctc gcgccagccg aactgttcgc caggctcaag gcgcgcatgc ccgacggcga    4860
ggatctcgtc gtgacccatg gcgatgcctg cttgccgaat atcatggtgg aaaatggccg    4920
cttttctgga ttcatcgact gtggccggct gggtgtggcg gaccgctatc aggacatagc    4980
gttggctacc cgtgatattg ctgaagagct tggcggcgaa tgggctgacc gcttcctcgt    5040
gctttacggt atcgccgctc ccgattcgca gcgcatcgcc ttctatcgcc ttcttgacga    5100
gttcttctga ggggatccgt cgactagagc tcgctgatca gcctcgactg tgccttctag    5160
ttgccagcca tctgttgttt gccctccc cgtgccttcc ttgaccctgg aagtgccac      5220 tcccactgtc ctttcctaat aaaatgagga aattgcatcg cattgtctga gtaggtgtca    5280
```

```
ttctattctg gggggtgggg tggggcagga cagcaagggg gaggattggg aagacaatag    5340
caggcatgct ggggagagat ctaggaaccc ctagtgatgg agttggccac tccctctctg    5400
cgcgctcgct cgctcactga ggccgcccgg gcaaagcccg ggcgtcgggc gacctttggt    5460
cgcccggcct cagtgagcga gcgagcgcgc agagagggga tggccaaccc ccccccccc    5520 ccccctgcag ccctgcatta atgaatcggc caacgcgcgg ggagaggcgg tttgcgtatt    5580
gggcgctctt ccgcttcctc gctcactgac tcgctgcgct cggtcgttcg gctgcggcga    5640
gcggtatcag ctcactcaaa ggcggtaata cggttatcca cagaatcagg ggataacgca    5700
ggaaagaaca tgtgagcaaa aggccagcaa aaggccagga accgtaaaaa ggccgcgttg    5760
ctggcgtttt tccataggct ccgcccccct gacgagcatc acaaaaatcg acgctcaagt    5820
cagaggtggc gaaacccgac aggactataa agataccagg cgtttccccc tggaagctcc    5880
ctcgtgcgct ctcctgttcc gaccctgccg cttaccggat acctgtccgc ctttctccct    5940 tcggaagcg tggcgctttc tcaatgctca cgctgtaggt atctcagttc ggtgtaggtc    6000
gttcgctcca agctgggctg tgtgcacgaa ccccccgttc agcccgaccg ctgcgcctta    6060
tccggtaact atcgtcttga gtccaacccg gtaagacacg acttatcgcc actggcagca    6120
gccactggta acaggattag cagagcgagg tatgtaggcg gtgctacaga gttcttgaag    6180
tggtggccta actacggcta cactagaagg acagtatttg gtatctgcgc tctgctgaag    6240
ccagttacct tcggaaaaag agttggtagc tcttgatccg gcaaacaaac caccgctggt    6300
agcggtggtt tttttgtttg caagcagcag attacgcgca gaaaaaaagg atctcaagaa    6360
gatcctttga tcttttctac ggggtctgac gctcagtgga acgaaaactc acgttaaggg    6420
attttggtca tgagattatc aaaaaggatc ttcacctaga tccttttaaa ttaaaaatga    6480
agttttaaat caatctaaag tatatatgag taaacttggt ctgacagtta ccaatgctta    6540
atcagtgagg cacctatctc agcgatctgt ctatttcgtt catccatagt tgcctgactc    6600
cccgtcgtgt agataactac gatacgggag ggcttaccat ctggccccag tgctgcaatg    6660
ataccgcgag acccacgctc accggctcca gatttatcag caataaacca gccagccgga    6720
agggccgagc gcagaagtgg tcctgcaact ttatccgcct ccatccagtc tattaattgt    6780
tgccgggaag ctagagtaag tagttcgcca gttaatagtt tgcgcaacgt tgttgccatt    6840
gctacaggca tcgtggtgtc acgctcgtcg tttggtatgg cttcattcag ctccggttcc    6900
caacgatcaa ggcgagttac atgatccccc atgttgtgca aaaaagcggt tagctccttc    6960
ggtcctccga tcgttgtcag aagtaagttg gccgcagtgt tatcactcat ggttatggca    7020
gcactgcata attctcttac tgtcatgcca tccgtaagat gcttttctgt gactggtgag    7080
tactcaacca agtcattctg agaatagtgt atgcggcgac cgagttgctc ttgcccggcg    7140
tcaatacggg ataataccgc gccacatagc agaactttaa aagtgctcat cattggaaaa    7200
cgttcttcgg ggcgaaaact ctcaaggatc ttaccgctgt tgagatccag ttcgatgtaa    7260
cccactcgtg cacccaactg atcttcagca tcttttactt tcaccagcgt ttctgggtga    7320
gcaaaaacag gaaggcaaaa tgccgcaaaa aagggaataa gggcgacacg gaaatgttga    7380
atactcatac tcttcctttt tcaatattat tgaagcattt atcagggtta ttgtctcatg    7440
agcggataca tatttgaatg tatttagaaa aataaacaaa taggggttcc gcgcacattt    7500
ccccgaaaag tgccacctga cgtctaagaa accattatta tcatgacatt aacctataaa    7560
aataggcgta tcacgaggcc ctttcgtctc gcgcgtttcg gtgatgacgg tgaaaacctc    7620
tgacacatgc agctcccgga gacggtcaca gcttgtctgt aagcggatgc cgggagcaga    7680
```

```
caagcccgtc agggcgcgtc agcgggtgtt ggcgggtgtc ggggctggct taactatgcg    7740
gcatcagagc agattgtact gagagtgcac catatgcggt gtgaaatacc gcacagatgc    7800
gtaaggagaa aataccgcat caggaaattg taaacgttaa tattttgtta aaattcgcgt    7860 taaattttg ttaaatcagc tcattttta accaataggc cgaaatcggc aaaatcccctt    7920 ataaatcaaa agaatagacc gagatagggt tgagtgttgt tccagtttgg aacaagagtc    7980
cactattaaa gaacgtggac tccaacgtca aagggcgaaa aaccgtctat cagggcgatg    8040
gcccactacg tgaaccatca ccctaatcaa gttttttggg gtcgaggtgc cgtaaagcac    8100
taaatcggaa ccctaaaggg agcccccgat ttagagcttg acggggaaag ccggcgaacg    8160
tggcgagaaa ggaagggaag aaagcgaaag gagcgggcgc tagggcgctg gcaagtgtag    8220
cggtcacgct gcgcgtaacc accacacccg ccgcgcttaa tgcgccgcta cagggcgcgt    8280
cgcgccattc gccattcagg ctacgcaact gttgggaagg gcgatcggtg cgggcctctt    8340
cgctattacg ccaggctgca                                                8360

<210> SEQ ID NO 29
<211> LENGTH: 18
<212> TYPE: DNA
<213> ORGANISM: Artificial Sequence
<220> FEATURE:
<223> OTHER INFORMATION: Forward primer for PIM and PIZ

<400> SEQUENCE: 29
ccaaggccgt gcataagg                                                    18

<210> SEQ ID NO 30
<211> LENGTH: 18
<212> TYPE: DNA
<213> ORGANISM: Artificial Sequence
<220> FEATURE:
<223> OTHER INFORMATION: Reverse primer for PIM and PIZ

<400> SEQUENCE: 30
ggccccagca gcttcagt                                                    18

<210> SEQ ID NO 31
<211> LENGTH: 18
<212> TYPE: DNA
<213> ORGANISM: Artificial Sequence
<220> FEATURE:
<223> OTHER INFORMATION: Probe for PIZ (mutant AAT)
<220> FEATURE:
<221> NAME/KEY: misc_signal
<222> LOCATION: (1)..(1)
<223> OTHER INFORMATION: 6FAM probe molecule
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_signal
<222> LOCATION: (18)..(18)
<223> OTHER INFORMATION: MGBNFQ probe molecule
<220> FEATURE:
<221> NAME/KEY: misc_feature
<222> LOCATION: (18)..(18)
<223> OTHER INFORMATION: n is a, c, g, or t

<400> SEQUENCE: 31
nctgaccatc gacaagan                                                    18

<210> SEQ ID NO 32
```

```
<211> LENGTH: 18
<212> TYPE: DNA
<213> ORGANISM: Artificial Sequence
<220> FEATURE:
<223> OTHER INFORMATION: Probe for PIM (wild-type AAT)
<220> FEATURE:
<221> NAME/KEY: misc_signal
<222> LOCATION: (1)..(1)
<223> OTHER INFORMATION: 6FAM probe molecule
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_signal
<222> LOCATION: (18)..(18)
<223> OTHER INFORMATION: MGBNFQ probe molecule
<220> FEATURE:
<221> NAME/KEY: misc_feature
<222> LOCATION: (18)..(18)
<223> OTHER INFORMATION: n is a, c, g, or t

<400> SEQUENCE: 32
nctgaccatc gacgagan                                              18
```